(12) United States Patent
Bovy et al.

(10) Patent No.: US 7,034,203 B1
(45) Date of Patent: Apr. 25, 2006

(54) METHODS AND COMPOSITION FOR MODULATING FLAVONOLS CONTENT

(75) Inventors: Arnaud G. Bovy, Bilthoven (NL); Hendrikus T. van der Hijden, Bedford (GB); Stephen G. Hughes, Exmouth (GB); Shelagh R. Muir, Bedford (GB); Adrianus J. van Tunen, Wageningen (NL); Martine E. Verhoeyen, Bedford (GB); Cornelis H. de Vos, Wageningen (NL)

(73) Assignee: Unilever Patent Holdings B.V., Atvlaardingen (NL)

( * ) Notice: Subject to any disclaimer, the term of this patent is extended or adjusted under 35 U.S.C. 154(b) by 0 days.

(21) Appl. No.: 09/626,377

(22) PCT Filed: Jan. 25, 1999

(86) PCT No.: PCT/EP99/00419

§ 371 (c)(1),
(2), (4) Date: Jan. 9, 2001

(87) PCT Pub. No.: WO99/37794

PCT Pub. Date: Jul. 29, 1999

(51) Int. Cl.
  *C12N 15/82* (2006.01)
  *A01H 5/00* (2006.01)
  *A01H 5/08* (2006.01)
  *A01H 5/10* (2006.01)

(52) U.S. Cl. ..................... 800/282; 800/317.4; 800/287
(58) Field of Classification Search ................. 800/282, 800/317.4, 287, 278, 298; 435/320.1, 419, 435/468
See application file for complete search history.

(56) References Cited

U.S. PATENT DOCUMENTS 5,603,936 A    2/1997    Monte

FOREIGN PATENT DOCUMENTS

| EP | 0 522 880 A2 | 1/1993 |
|----|----|----|
| GB | 2 317 561 | 4/1998 |
| WO | WO 90/11682 | 10/1990 |
| WO | WO 91/02059 | 2/1991 |
| WO | WO 93/14211 | 7/1993 |
| WO | WO 93/18171 | 9/1993 |
| WO | WO 94 03606 | 2/1994 |
| WO | WO 95/34634 | 12/1995 |
| WO | WO 97 32023 | 9/1997 |

OTHER PUBLICATIONS

Lloyd et al: "Arabidopsis and Nicotiana anthocyanin production activated by maize regulators R and C1", Science, vol 258, Dec. 11, 1992 pp. 1773–1775, XP002106592.
Quattrochio et al: "Iregulatory genes controlling anthocyanin pigmentation are functionally conserved among plant species and have distinct sets of target genes", Plant Cell, no 5, Nov. 1993 p. 1497 1512 XP002077025, ISSN: 1040–4651.
Moyano t al: "Apparent redundancy in myb gene function provides gearing for the control of flavonoid biosyntheses in Antirrhinum flowers", Plant Cell, , no. 8, SEP. 1996 p. 1519 1532, XP002077024, ISSN: 1040–4651.
Mooney et al: Altered regulation of tomato and tobacco pigmentation genes caused by the delila gene of Antirrhinum, Plant Journal, vol. 2, no 7, Jan. 1995 p. 333 339, XP002077023 ISSN: 0960–7412.
Goldsbrough et al: "Lc as a non–destructive visual reporter and transposition excision marker gene for tomato", Plant Journal, vol 6, no 9, Jan. 1996 p. 927 933, XP002077022, ISSN: 0960–7412.
Zornoza et al: "Flavonoids content of tomato plants for the study of nutitional status", Plant and Soil, vol 82, 1984 pp. 269–271, XP002106593.
Database WPI, Section CH, Week 9724, Derwent Publications Ltd., AN 97–266467, XP002106595 & JP 09 094077 A. , Apr. 8, 1997.
Rice–Evans et al: "Antioxidant properties of phenolic compounds", Trends in Plant Science, vol 4, no 2, Apr. 1997 p. 152 159, XP002077026, ISN: 1360–1385.
Woldecke, et al: "Flavonle und Flavone der Gemusearten. III, Flavonole und Flavone de Gemuseparprikas", Zeitschrift Fuu Lebensmittel–Untersuchung Und–Forschung, vol 15, No. 4, 1974, pp. 216–219, XP002106594.
Koes et al, BioEssays, 16(2):122–133 (1994).
Yoder et al, Euphytica, 79:163–167 (1994).
Goldsbrough et al, Plant Physiol., 105:491–496 (1994).
Rice–Evans et al, Reviews, 2(4):152–159 (1997) (XP–002077026).
Woldecke et al, Zeitschrift fuu Lebensmittel–Untersuchung und–Forschung, 15(4):216–219 (1974) (XP–002106594).
Zornoza et al, Plant and Soil, 82:269–271 (1984) (XP–002106593).
Lloyd et al, Science, 258:1773–1775 (1992) (XP–002106592.
Quattrocchio et al, The Plant Cell, 5:1497–1512 (1993 (XP–002077025).
Moyano et al, The Plant Cell, 8:1519–1532 (1996) (XP–002077024).
Mooney et al, The Plant Journal, 7(2):333–339 (1995) (XP–002077023).
Goldsbrough et al, The Plant Journal, 9(6):927–933 (1996) (XP–002077022).
Derwent, AN 97–266467, JP 09 094077 Abstract (XP–002106595.

*Primary Examiner*—David T. Fox
*Assistant Examiner*—Cynthia Collins
(74) *Attorney, Agent, or Firm*—Morgan Lewis & Bockius LLP

(57) ABSTRACT

A method for manipulating the production of flavonoids other than anthocyanins in plants by manipulating gene activity in the flavonoid biosynthetic pathway by expressing two or more genes encoding transcription factors for flavonoid biosynthesis, compositions for use in such a method and tomato plants having altered flavonoid levels are disclosed.

3 Claims, 31 Drawing Sheets

Fig. 1.
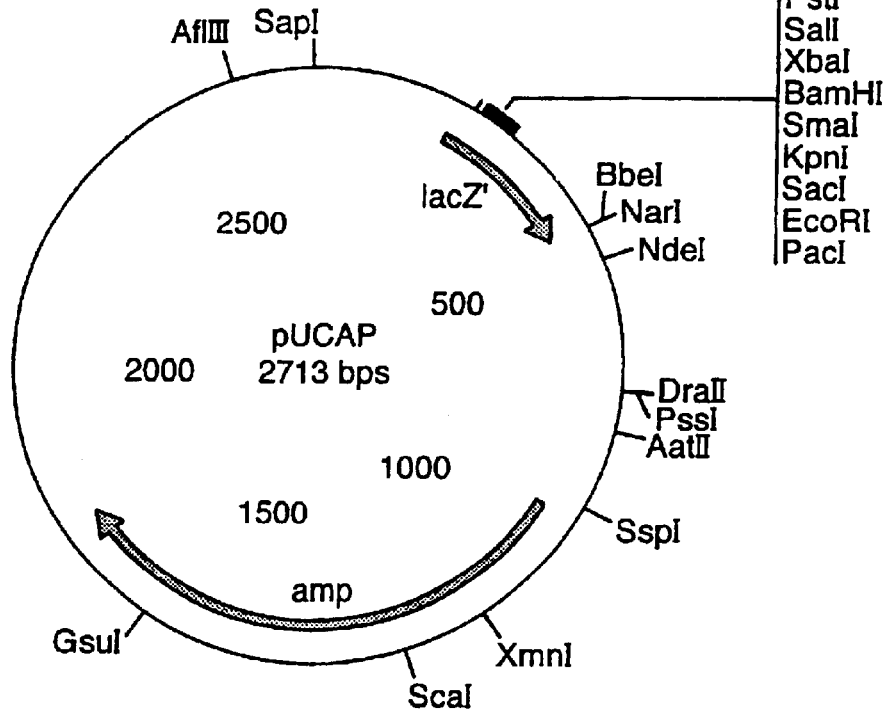
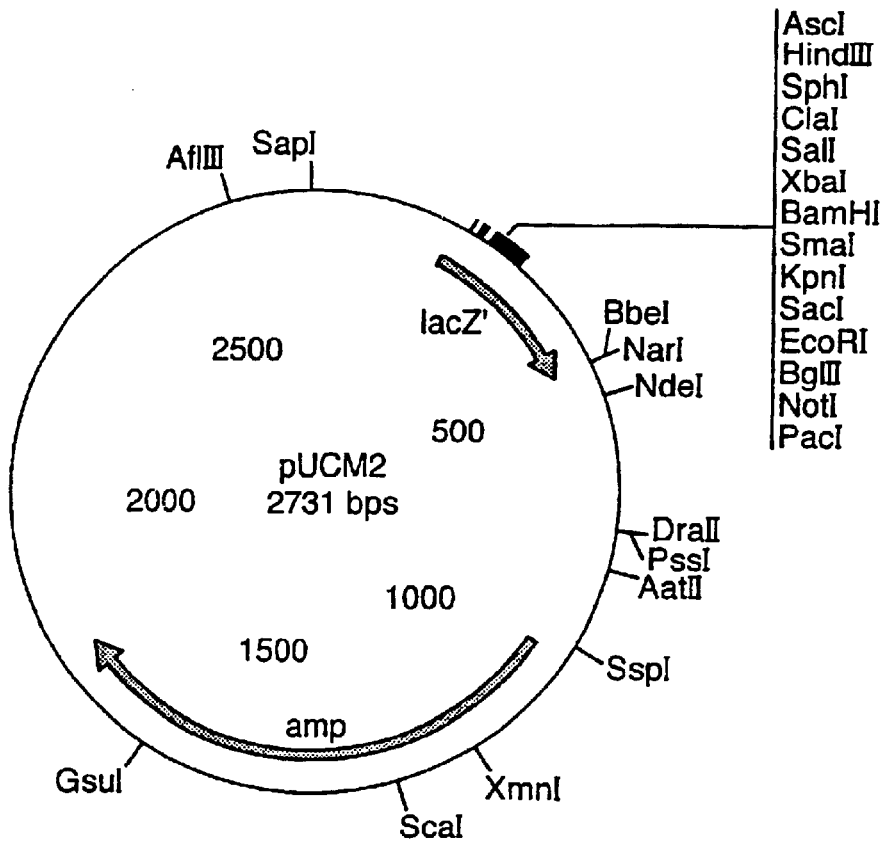

Fig. 2.
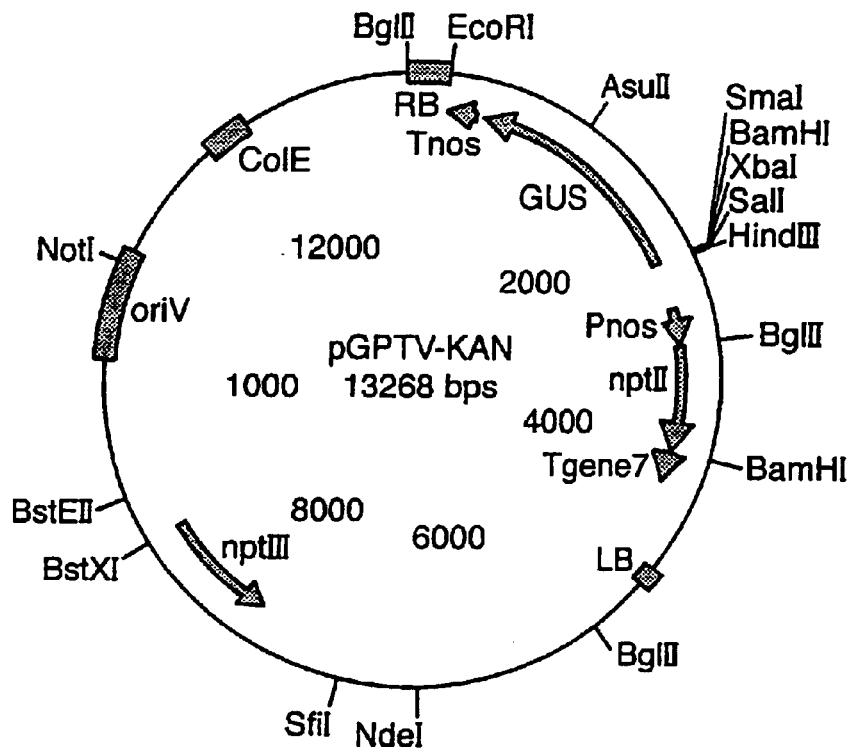
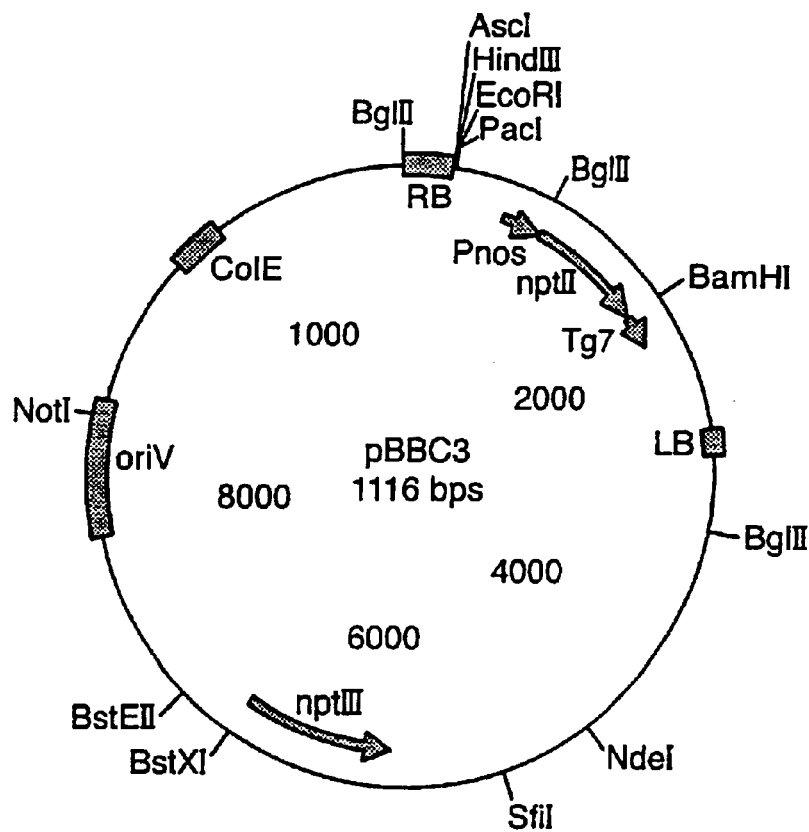

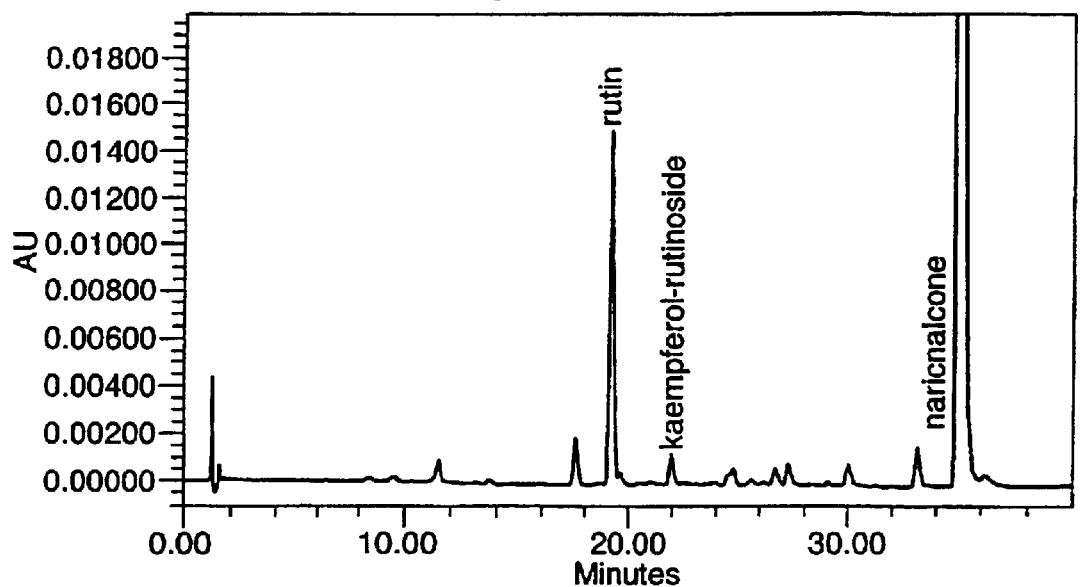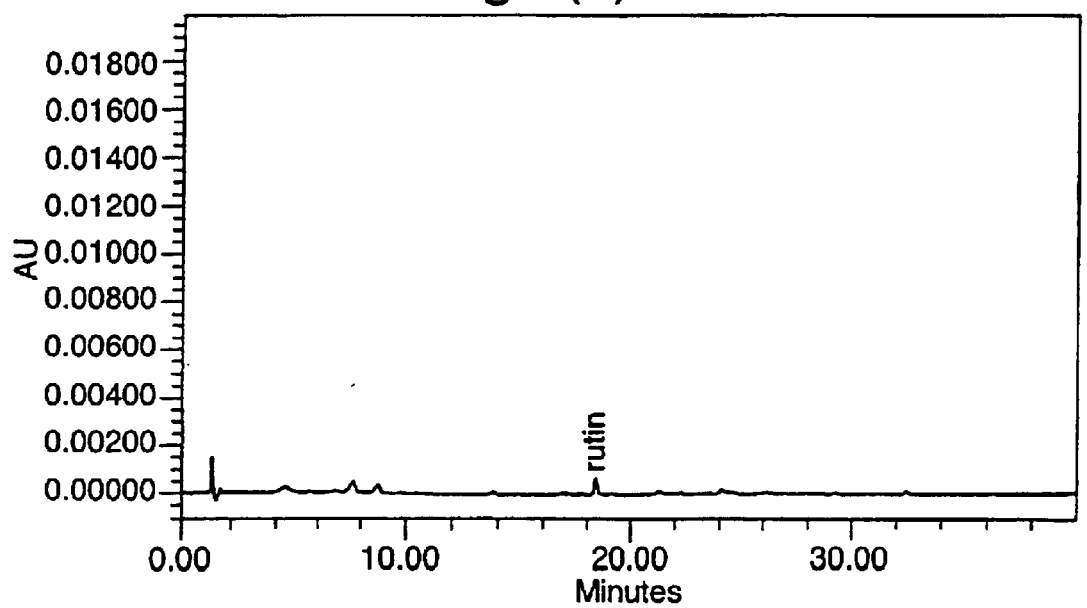

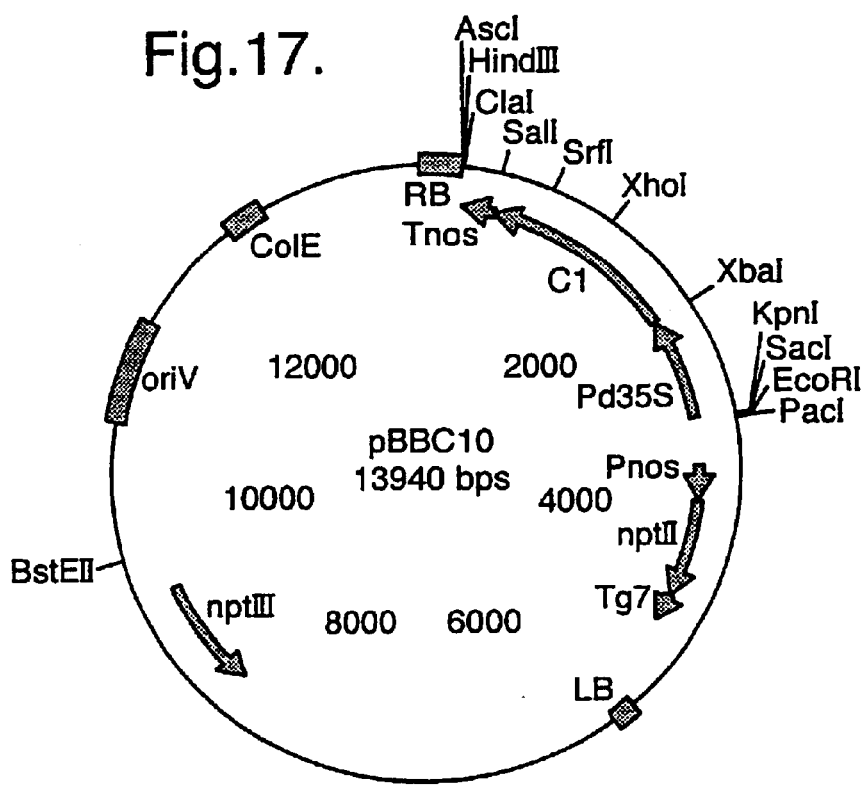
Fig. 17.
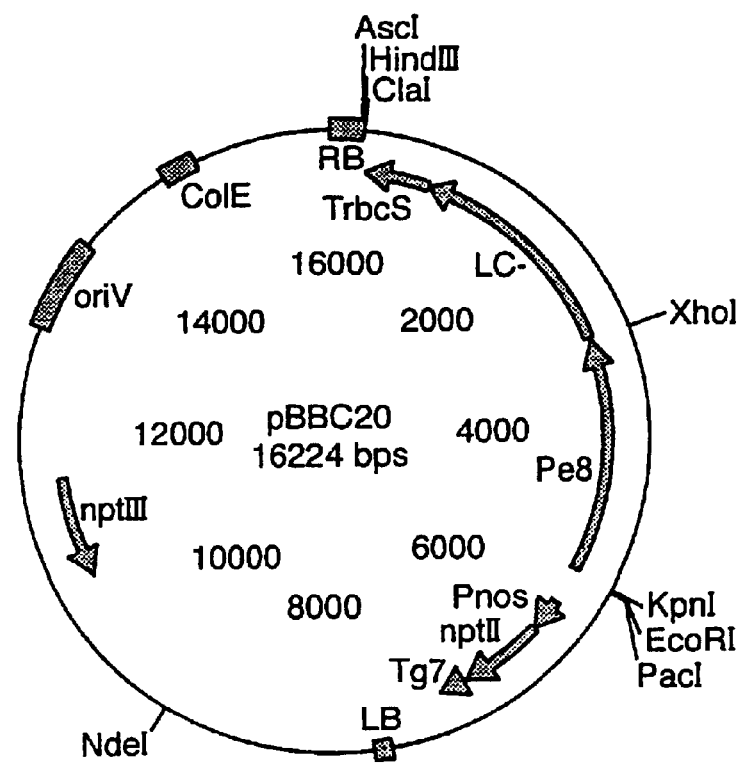

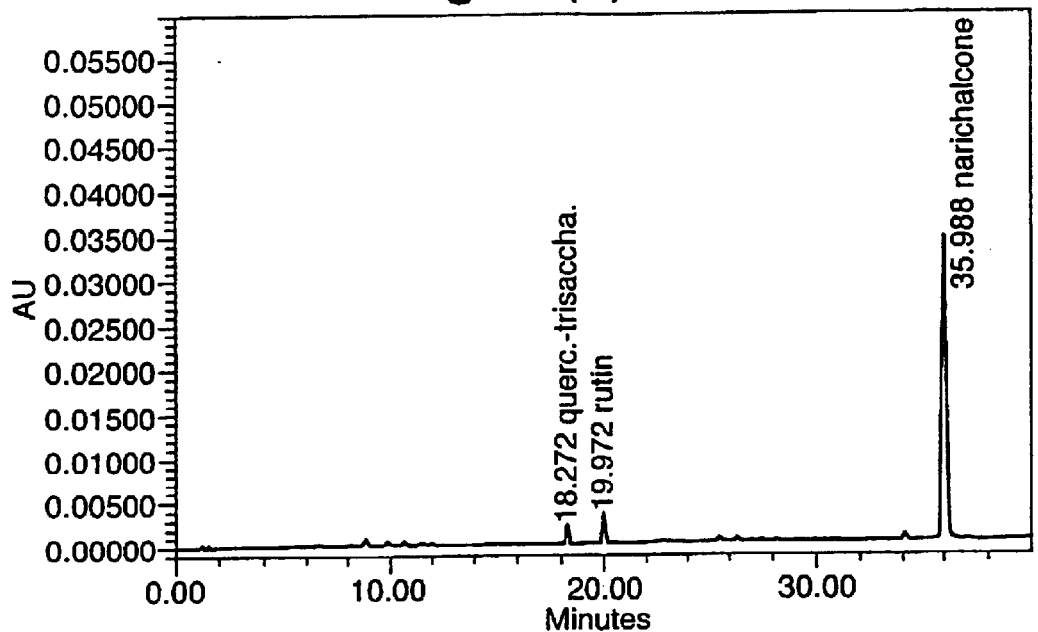
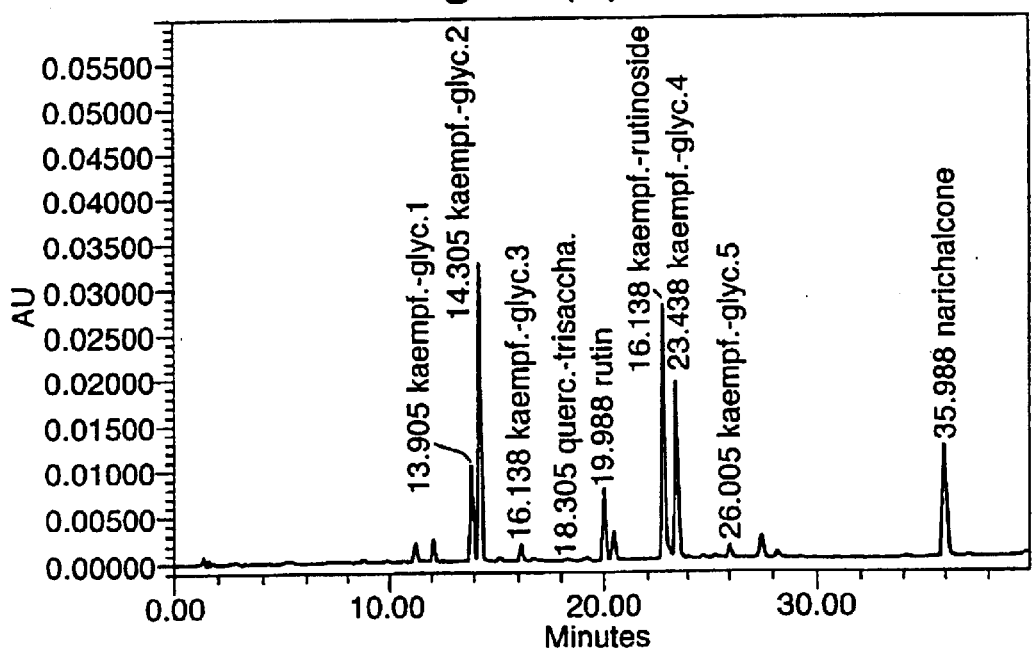

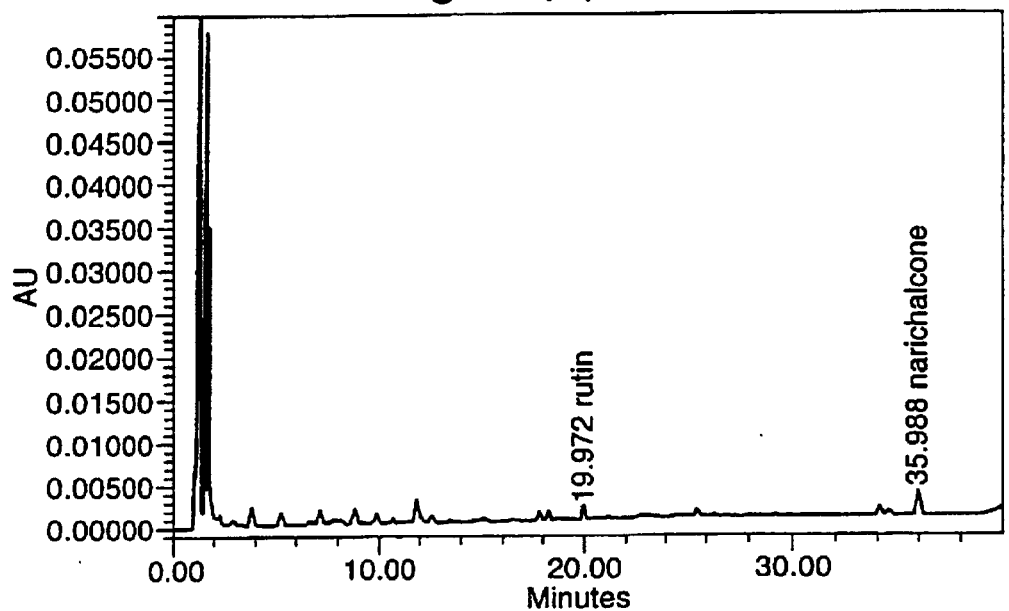
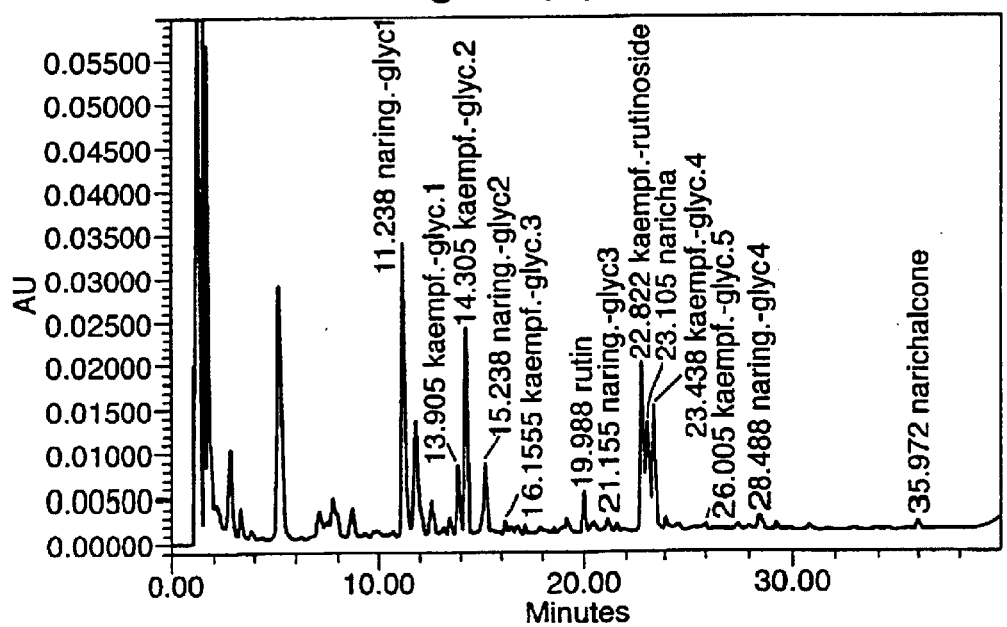

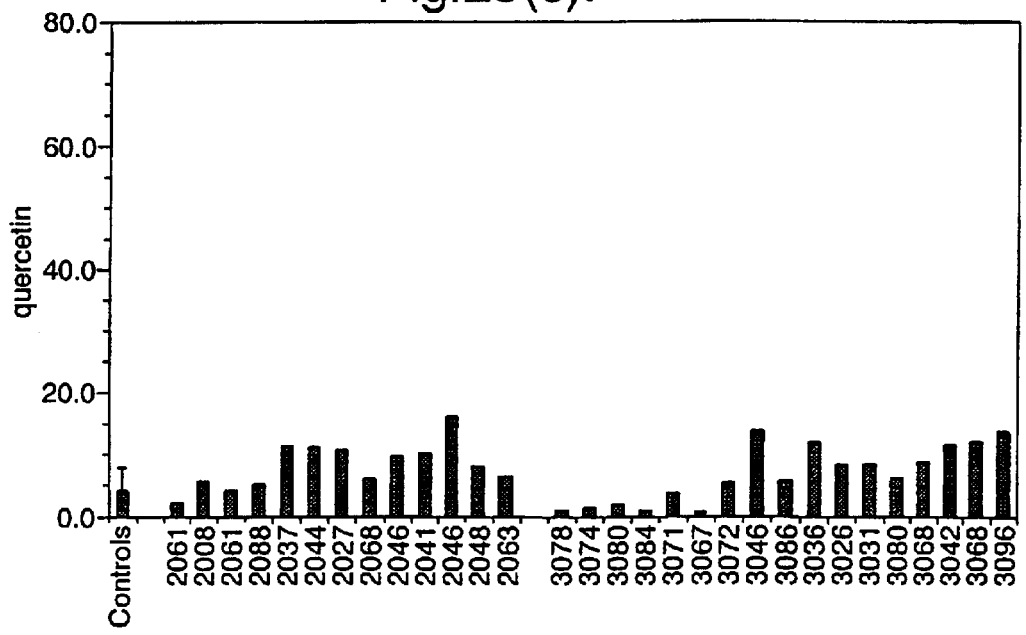
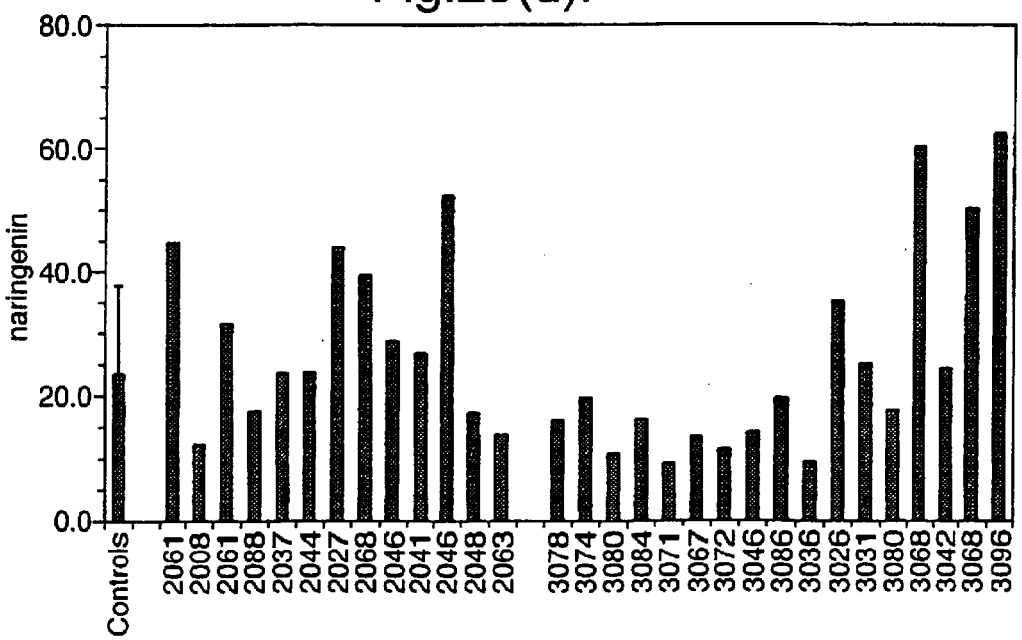

METHODS AND COMPOSITION FOR MODULATING FLAVONOLS CONTENT

CROSS-REFERENCE TO RELATED APPLICATIONS

This application is a 371 of PCT/EP99/00419 filed 25 Jan. 1999.

FIELD OF THE INVENTION

The present invention relates generally to methods for manipulating the production of flavonoids in plants by manipulating gene activity in the flavonoid biosynthetic pathway and compositions for use in such methods. In particular, it relates to methods for increasing levels of flavonoids other than anthocyanins by expressing genes encoding transcription factors involved in controlling expression of genes encoding enzymes of the flavonoid biosynthetic pathway.

BACKGROUND OF THE INVENTION

Flavonoids form a large group of polyphenolic compounds, based on a common diphenylpropane skeleton, which occur naturally in plants. Included within this class of compounds are flavonols, flavones, flavanones, catechins, anthocyanins, isoflavonoids, dihydroflavonols and stilbenes. The flavonoids are mostly present as glycosides.

In tomato fruits, the main flavonoid found is narichalcone (naringenin chalcone) (Hunt et al, Phytochemistry, 19, (1980), 1415–1419). It is known to accumulate almost exclusively in the peel and is simultaneously formed with colouring of the fruit. In addition to naringenin chalcone, glycosides of quercetin and, to a lesser extent, kaempferol are also found in tomato peel.

Reports in the literature suggest that there is increasing evidence that flavonoids, especially flavonols are potentially health-protecting components in the human diet. Epidemiological studies suggest a direct relationship between cardio-protection and increased consumption of flavonoids, in particular flavonols of the quercetin and kaempferol type, from dietary sources such as onion, apples and tea (see, for example, Hertog et al, Lancet, 342 (1993), 1007–1011).

Flavonoids have been reported to exhibit a wide range of biological activities in vitro including anti-inflammatory, anti-allergic and vasodilatory activity (Cook et al, Nutritional Biochemistry, 7, (1996), 66–76). Such activity has been attributed in part to their ability to act as antioxidants, capable of scavenging free radicals and preventing free radical production. Within this group of compounds, those having the most potent antioxidant activity are the flavonols (Rice-Evans et al, Free Radical Research, 22, (1995), 375–383). In addition, flavonoids can also inhibit the activity of key processes such as lipid peroxidation, platelet aggregation and capillary permeability (see Rice-Evans et al, Trends in Plant Science, 2, (1997), 152–159).

Based on studies of this type, there is presently considerable interest in the development of food products from plants rich in such protective flavonoids.

It would be desirable to produce plants which intrinsically possess elevated levels of health protecting compounds such as flavonoids in order to develop food products with enhanced protective properties. Traditionally, the approach to improving plant varieties has been based on conventional cross-breeding techniques, but these are slow as they require time for breeding and growing successive plant generations. More recently, recombinant DNA technology has been applied to the general problem of modifying plant, genomes to produce plants with desired phenotypic traits. Whilst reference has been made in the literature to the use of genetic manipulation techniques in modifying the flavonoid biosynthetic pathway, as discussed beneath, it is notable that these attempts have been directed in general towards modifying pigmentary anthocyanin production. For example, several studies have attempted to modify the flavonoid pathway by the introduction of genes encoding for enzymes in the flavonoid pathway. Examples of these are EP522880, WO 90/11682, Goldsbrough et al in Plant Physiology (1994) 105:191–194 and Yoder et al, in Euphytica (1994) 79: 163–167.

Other studies have attempted to modify the anthocyanin biosynthesis pathway by altering the expression of a single transcription factor. Examples of these are WO 91/2059, Goldsbrough et al, (1996), Plant Journal, 9(6), 927–933, Mooney et al (1995), Plant Journal (1995), 7(2), 333–339, W093/14211, W093/18171 and Moyano et al, in Plant Cell, Vol 8, 1519–1532, 1996.

The flavonoid biosynthetic pathway is well established and has been widely studied in a number of different plant species (see, for example, Koes et al, BioEssays, 16, (1994), 123–132). Briefly, three molecules of malonyl-CoA are condensed with one molecule of coumaroyl-CoA, catalysed by the enzyme chalcone synthase, to give naringenin chalcone which rapidly isomerises, catalysed by chalcone isomerase, to naringenin. Subsequent hydroxylation of naringenin catalysed by flavanone 3-hydroxylase leads to dihydrokaempferol. Dihydrokaempferol itself can be hydroxylated to produce either dihydroquercetin or dihydromyricetin. All three dihydroflavonols subsequently can be converted to anthocyanins (by the action of dihydroflavonol reductase and flavonoid glucosyltransferase) or alternatively converted to flavonols such as kaempferol, quercetin and myricetin by the action of flavonol synthase.

Hitherto, studies in maize have identified two regulatory genes, C1 and R which are required for the production of anthocyanin (see Lloyd et al, Science, (1992), 258, 1773–1775). The C1 gene encodes a protein which has a myb DNA binding domain (Paz-Ares, et al, (1987) EMBO Journal, 6, 3553–3558) whilst the R gene encodes a protein with a basic helix-loop-helix domain characteristic of the myc family of transcriptional regulators (Ludwig et al, Proc. Natl. Acad. Sci., USA, 86 (1989) 7092–7096).

In Lloyd et al, referred to above, the expression of these anthocyanin pathway-specific transcriptional factors from the monocot maize in the dicots *Arabidopsis thaliana* and *Nicotiana tabacum* is disclosed. It is reported that anthocyanin production in both plant species is activated by R (Lc allele) in those tissues that normally produce anthocyanins but that C1 alone has no effect. Hybrid transgenic *Arabidopsis* expressing both transcription factors, placed under transcriptional control of the cauliflower mosaic virus 35S promoter, was reported to produce anthocyanins in tissues which would not normally express anthocyanins such as root, petal and stamen.

Crosses were performed using one R(Lc)-expressing line to pollinate three plants expressing C1. As all four parents were heterozygous, it would be expected that one in four of the progeny would contain both R and C1. In one cross, thirty six progeny were produced, of which four plants displayed anthocyanin accumulation in the roots and gave a small amount of anthocyanin in the petal and stamen tissue, the exact magnitude of the fold increase over wild type being unrecorded. Of the thirty eight progeny resulting from another cross, three plants gave anthocyanin in the petal tissue whereas in a third cross, no progeny with pigmentation in root or petal tissue were produced. Plants producing anthocyanins in the root and petals are assumed to contain both C1 and R, although this is not confirmed experimentally, nor is there any explanation as to why none of the progeny resulting from the third cross displayed anthocyanin accumulation in roots and petals. The authors of the study do not report whether the presence of both R and C1 in *Arabidopsis* leads to the constitutive production of anthocyanin in the whole plant or if anthocyanin production is restricted to certain areas of the plant.

Reports in the literature suggest that the introduction of a transcription factor from another species into *Arabidopsis* may cause it to behave atypically with respect to upregulation of anthocyanin production, (see for example, Mooney et al, Plant Journal, (1995), 7, 333–339). Here, overexpression of the gene encoding the *Antirrhinum DELILA* transcription factor under the control of the cauliflower mosaic virus 35S promoter gave rise to enhanced anthocyanin levels in both tomato and tobacco but in *Arabidopsis*, no obvious phenotype occurred. In tomato, increased pigmentation was produced in hypocotyl, cotyledon, leaves, stem and roots but no detectable enhancement of normal pigmentation in tomato fruits and testa of the seed was found. Enhanced pigmentation was seen in the flowers in tobacco but no vegetative parts were pigmented.

As reported by Goldsbrough et al, (1996) Plant Journal, 9(6), 927–933, expression of the Lc gene in tomato under the control of the cauliflower mosaic virus 35S promoter led to accumulation of anthocyanin only in those tissues which would normally be expected to produce anthocyanins such as leaves, stems, sepals, and the main vein of petals. In leaves, all the anthocyanin production occurred in the epidermal layer only. It is further reported that overexpression of homozygous Lc is lethal to the plant.

Quattrocchio et al, in Plant Cell, Vol 5, 1497–1512 (1993) describes the introduction of genes into parts of *petunia* leaves by particle bombardment. In these experiments the combination of the Lc and C1 transcription factors leads to anthocyanin accumulation in the leaves. No teaching is provided as to what the effects of this methodology are on the production of flavonoids other than anthocyanin such as flavonols. Furthermore it is well known in the art that experiments carried out by particle bombardment techniques cannot be used as reliable predictors for the effects which could be obtained by transgene incorporation of genes.

There are no reports in the literature which confirm that levels of anthocyanins are directly correlated to the levels of flavonols or other flavonoids. Also there is no disclosure in the literature of the manipulation of, flavonoids other than anthocyanins in plants by means of expression of transcriptional regulatory factors.

Accordingly, there remains a continuing need for the development of methods for enhancing the levels of flavonoids other than anthocyanins; in particular flavonols, in plants.

Furthermore there is a need to enhance the levels of flavonoids other than anthocyanins in plants or specific parts thereof, while avoiding a substantial increase in anthocyanin production, such that on the one hand the amount of desirable ingredients is increased, but the colour of the plant remains substantially the same.

SUMMARY OF THE INVENTION

In a first aspect, the invention provides a method for producing a plant capable of exhibiting altered levels of flavonoids other than anthocyanins comprising incorporating into said plant two or more genes each encoding a different transcription factor for flavonoid biosynthesis, or a sequence functionally equivalent thereto, each gene being operably linked to a promoter.

Surprisingly it has been found that a combination of two or more genes encoding for transcription factors provides altered levels of flavonoids other than anthocyanins. Preferably the plants according to the invention are stably transformed with these genes.

The invention also provides a plant having two or more transgenes each encoding a different transcription factor for flavonoid biosynthesis, or a sequence functionally equivalent thereto, preferably stably incorporated into its genome such that its ability to produce flavonoids other than anthocyanins is altered.

The invention further provides a tomato plant having a combination of two or more additional genes encoding transcription factors for flavonoid biosynthesis incorporated, preferably stably, into its genome such that its ability to produce flavonoids other than anthocyanins is altered.

Also provided is a transformed plant having enhanced levels of flavonoids other than anthocyanin, particularly flavonol levels, compared to similar untransformed plants.

Further provided is a fruit-bearing plant, particularly a tomato plant, having flavonoids, particularly flavonols, in the, flesh of the fruit.

Seeds, fruits and progeny of such plants and hybrids are also included within the invention.

The invention further provides a DNA construct comprising sequences coding for a combination of two or more genes, each gene encoding a different transcription factor for flavonoid biosynthesis, or a functionally equivalent sequence thereof, each gene being operably linked to a promoter. When transformed into a plant cell, these constructs are useful in overexpressing genes encoding enzymes of the flavonoid biosynthetic pathway, thereby altering the ability of the plant to produce flavonoids other than anthocyanins. The invention also provides for plants comprising these constructs together with seeds, fruits and progeny thereof.

Food products such as sauces, dressings, ketchups and soups, comprising a plant prepared according to the invention are also provided.

Also provided are skin and hair protective products comprising a plant according to the invention.

BRIEF DESCRIPTION OF THE DRAWINGS

The present invention may be more fully understood by reference to the following description, when read together with the accompanying drawings in which:

FIG. 2 shows restriction maps of plasmids pGPTV-KAN and pBBC3.

Abbreviations: Pnos: nopaline synthase promoter; Pd35s: Cauliflower Mosaic Virus (CAMV) double enhanced 35s promoter; Tnos: nopaline synthase terminator; Trbc: pea ribulose bisphosphate carboxylase small-subunit gene terminator; C1: maize C1 gene; Lc$^-$: maize Lc gene without leader sequence; Lc$^+$: maize Lc gene plus leader sequence.

Figure 4:
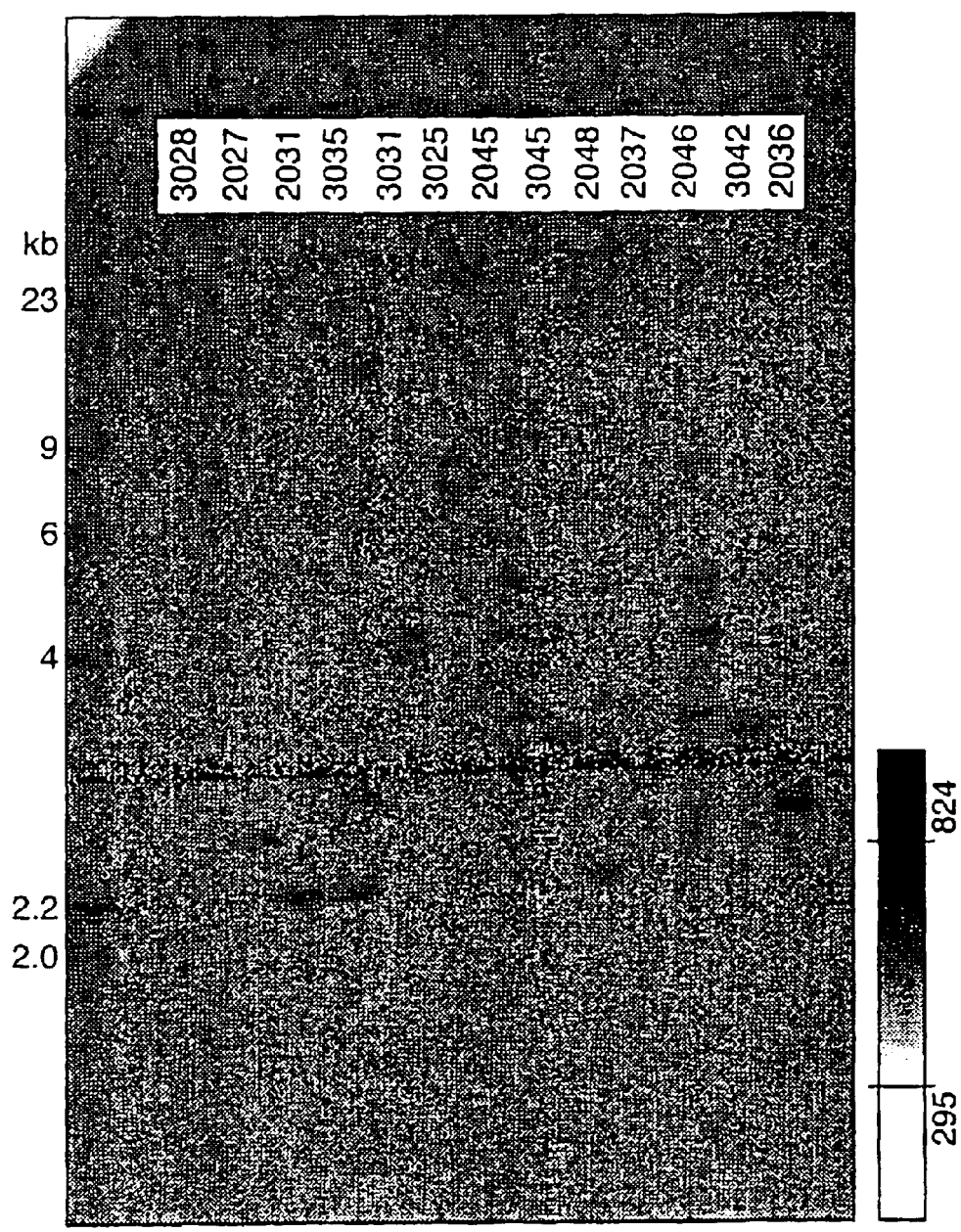

FIG. 4 shows a Southern blot of chromosomal DNA from tomato. Chromosomal DNA was isolated from leaves of transgenic and non-transgenic tomato plants. 5 μg DNA was digested with BglII, separated on an agarose gel and blotted to a nylon filter. The DNA was hybridised with a radiolabeled nptII specific probe and autoradiographed, using a bio-imager.

Figure 5A:
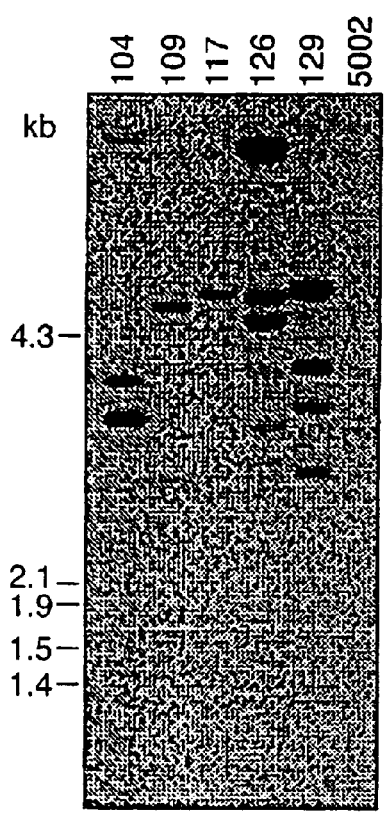
Figure 5B:
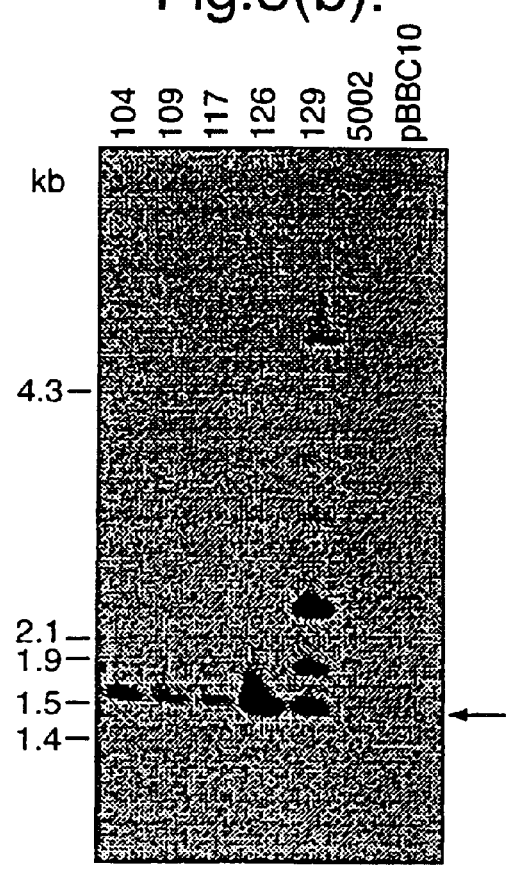

FIG. 5 shows a Southern blot of chromosomal DNA from tomato. Chromosomal. DNA was isolated from leaves of transgenic and non-transgenic tomato plants. 5 μg DNA was digested with EcoRI (panel A) and NcoI (panel B), separated on an agarose gel and blotted to a nylon filter. The DNA was hybridised with a radiolabeled C1 specific probe and autoradiographed. The arrow points to the hybridising 1.5 kb NcoI-band from pBBC10.

Figure 6:
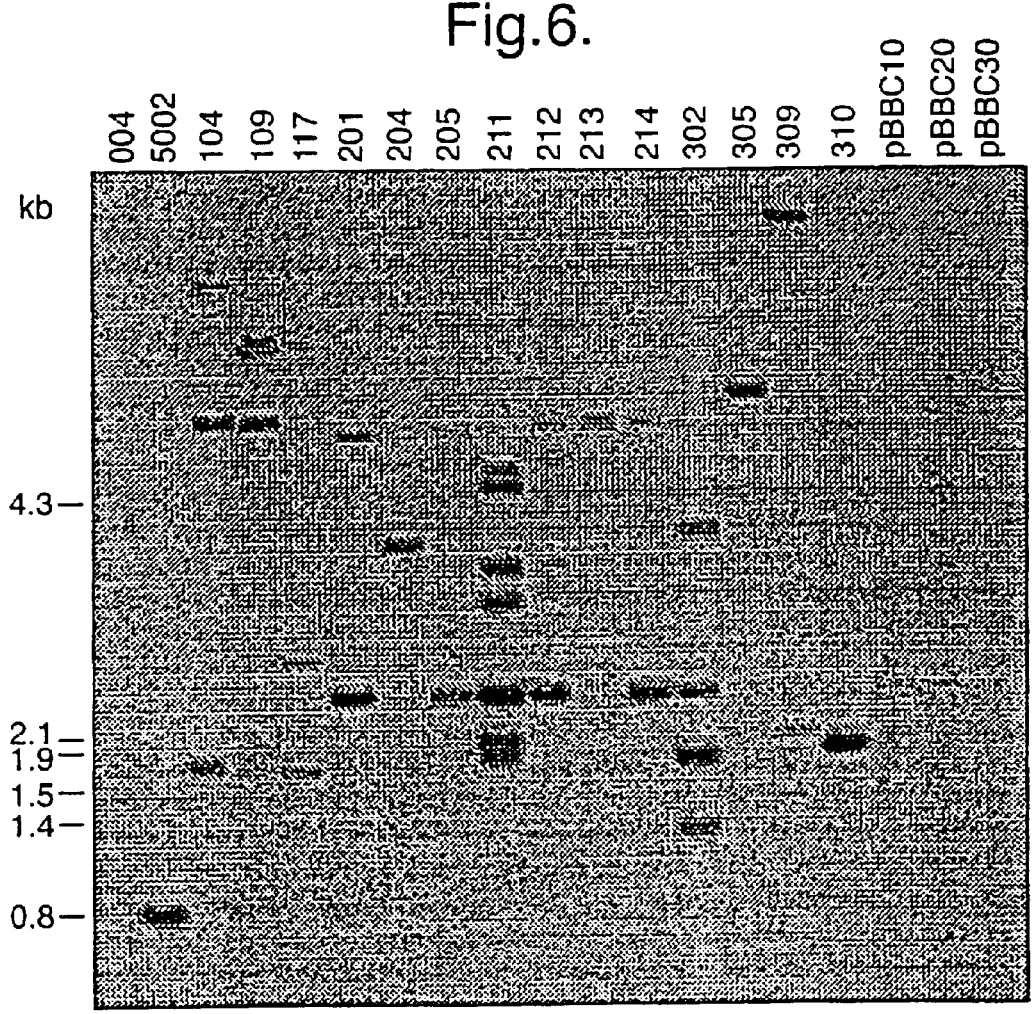

FIG. 6 shows a Southern blot of chromosomal DNA from tomato. Chromosomal DNA was isolated from leaves of transgenic and non-transgenic tomato plants. 5 μg DNA was digested with BglII/ClaI, separated on an agarose gel and blotted to a nylon filter. The DNA was hybridised with a radiolabeled nptli specific probe and autoradiographed.

Figure 7:
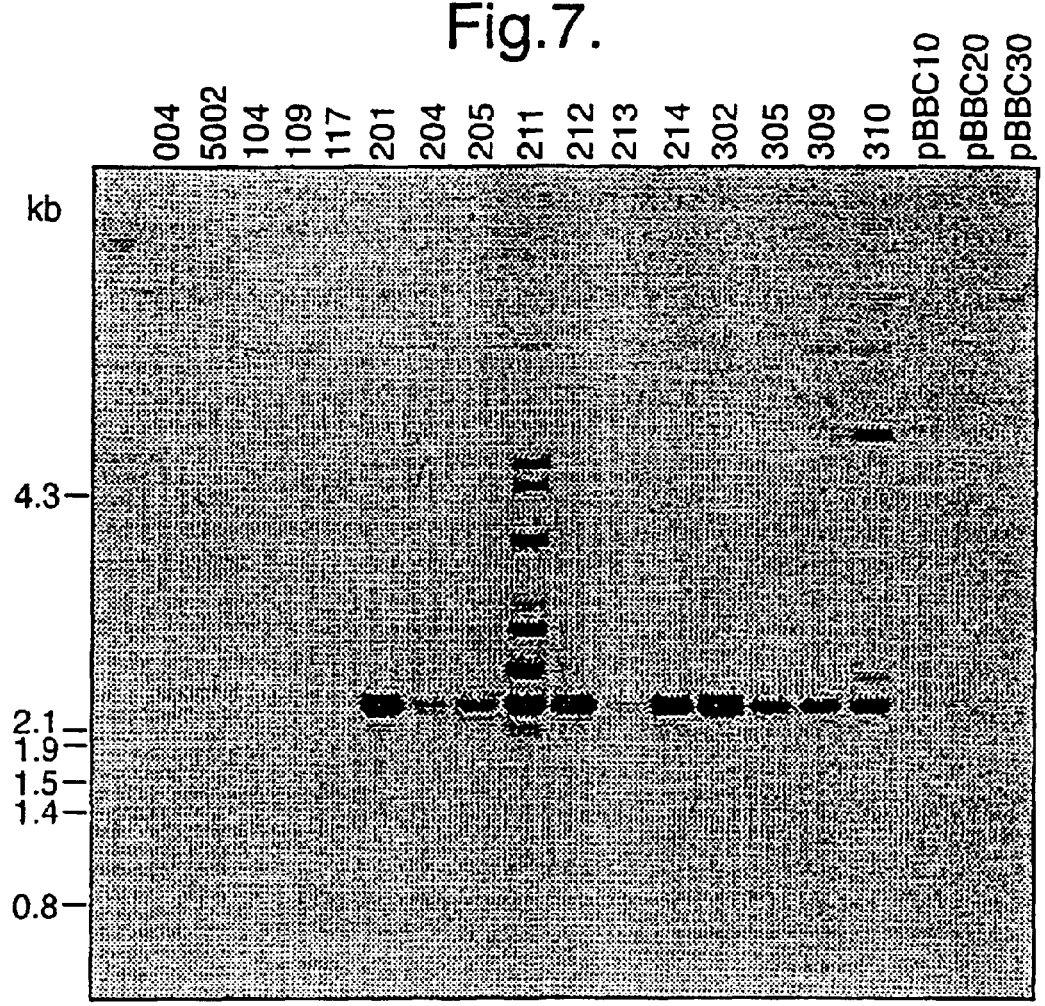

FIG. 7 shows a Southern blot of chromosomal DNA from tomato. Chromosomal DNA was isolated from leaves of transgenic and non-transgenic tomato plants. 5 μg DNA was digested with BglII/ClaI, separated on an agarose gel and blotted to a nylon filter. The DNA was hybridised with a radiolabeled Lc specific probe and autoradiographed.

FIG. 8 shows typical HPLC chromatograms, recorded at 370 nm, of hydrolysed extracts of (A) peel and (B) flesh tissue from red fruits of untransformed tomato plants. Peaks of quercetin and kaempferol aglycons are indicated.

FIG. 9 shows typical HPLC chromatograms, recorded at 360 nm, of non-hydrolysed extracts of (A) peel and (B) flesh tissue from red fruits of untransformed tomato plants. Peaks of different flavonol-glycosides and of naringenin-chalcone are indicated by compound name.

Figure 10A:
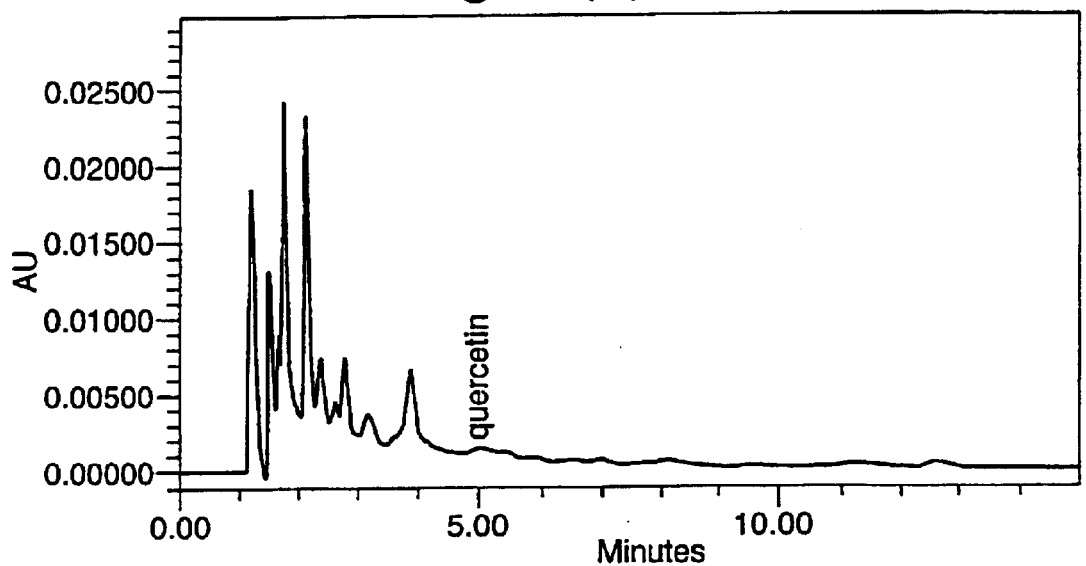
Figure 10B:
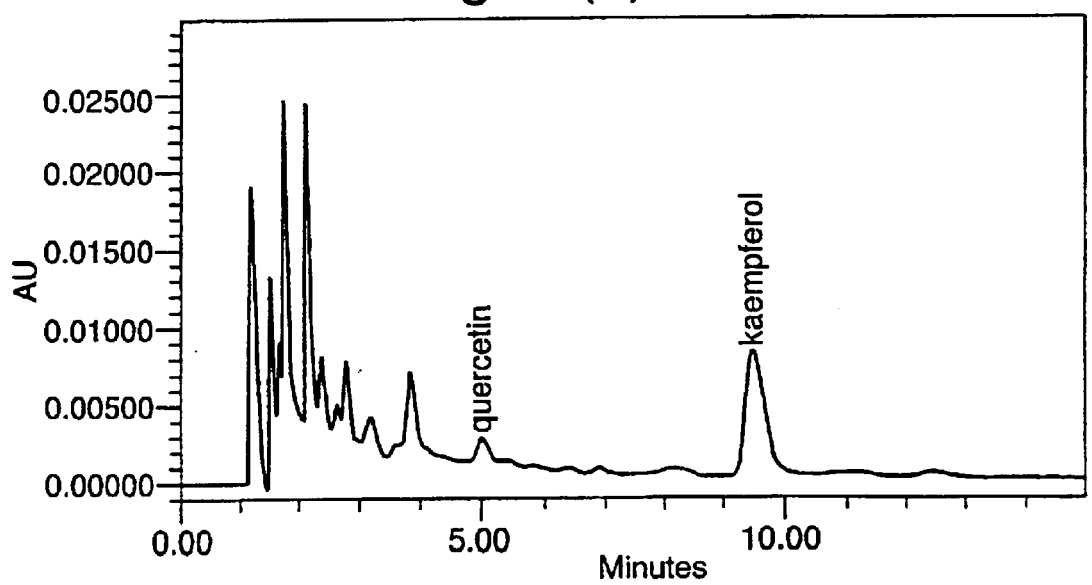

FIG. 10 shows HPLC-chromatograms, recorded at 370 nm, of hydrolysed extracts of flesh tissue from red fruits of (A) an untransformed plant and (B) a plant transformed with the pBBC300 gene construct.

Figure 11:
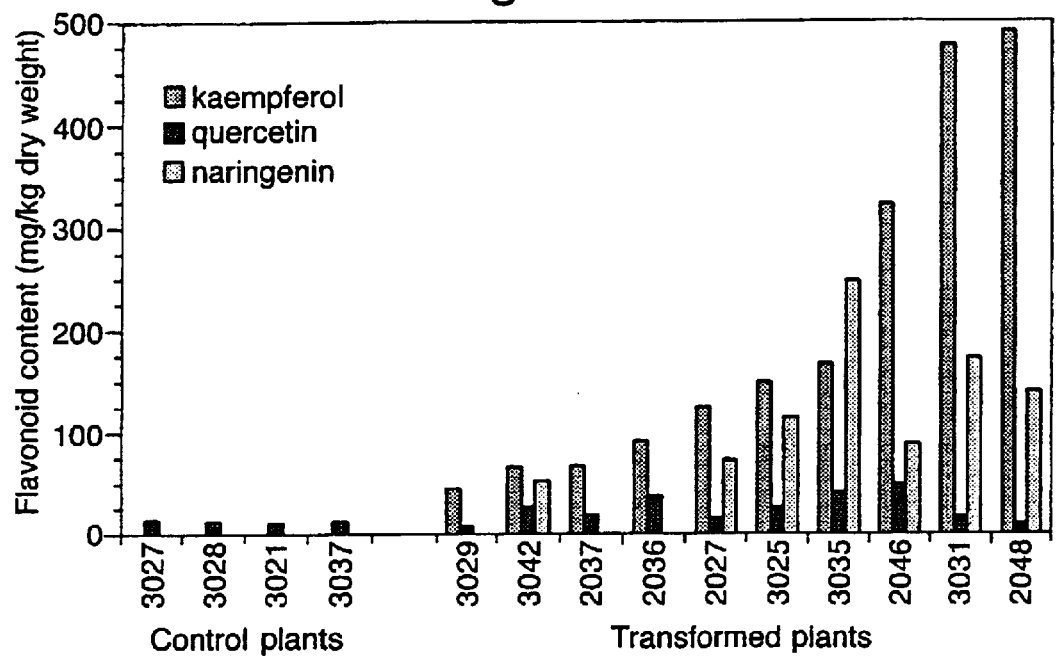

FIG. 11 shows levels of quercetin, kaempferol and naringenin (in mg/kg dry weight (DW)) in extracts from flesh of red fruits from some control plants and plants successfully transformed with either the pBBC200 (2000–2499) series of transformed plants) or the pBBC300 (3000 series of transformed plants) gene construct. Data were calculated from hydrolysed extracts, i.e. naringenin is derived from isomerization of narichalcone and quercetin and kaempferol aglycons are derived from their respective glycosides.

Figure 12:
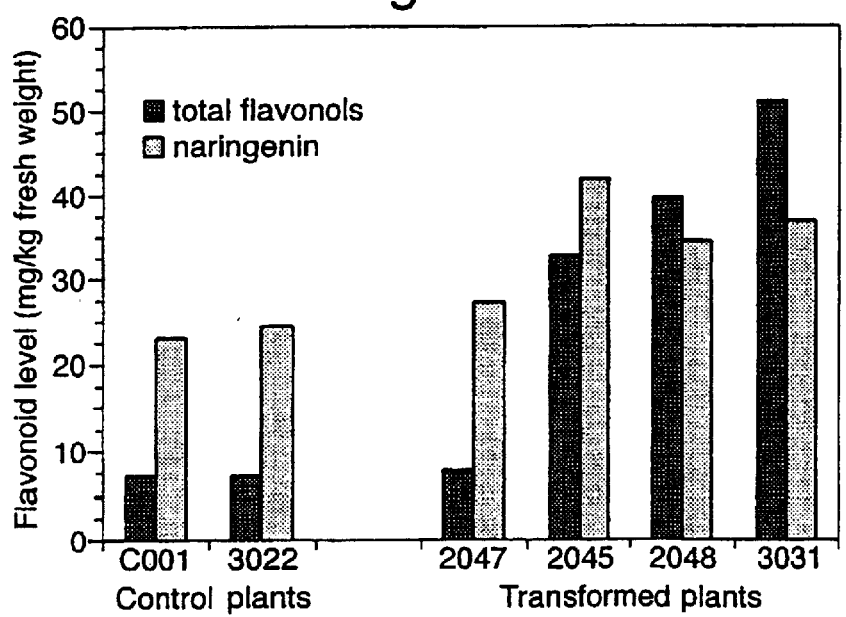

FIG. 12 shows levels of total flavonols (quercetin plus kaempferol) and naringenin in extracts from whole fruits of some control and transformed tomato plants. Data were calculated from hydrolysed extracts, i.e. naringenin is derived from isomerization of narichalcone, and quercetin and kaempferol aglycons are derived from their respective glycosides.

Figure 13A:
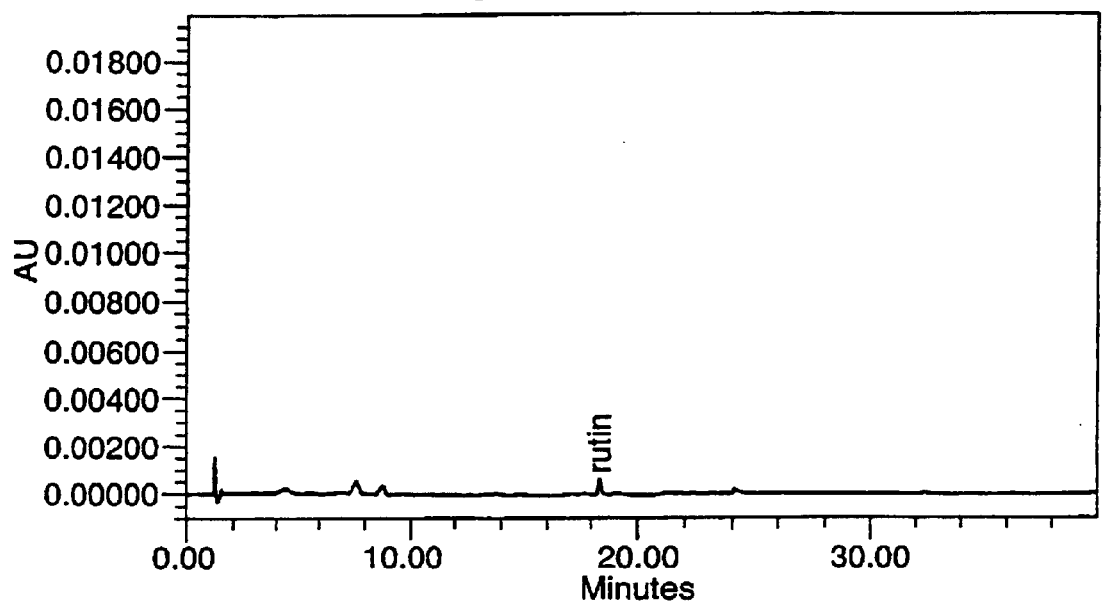
Figure 13B:
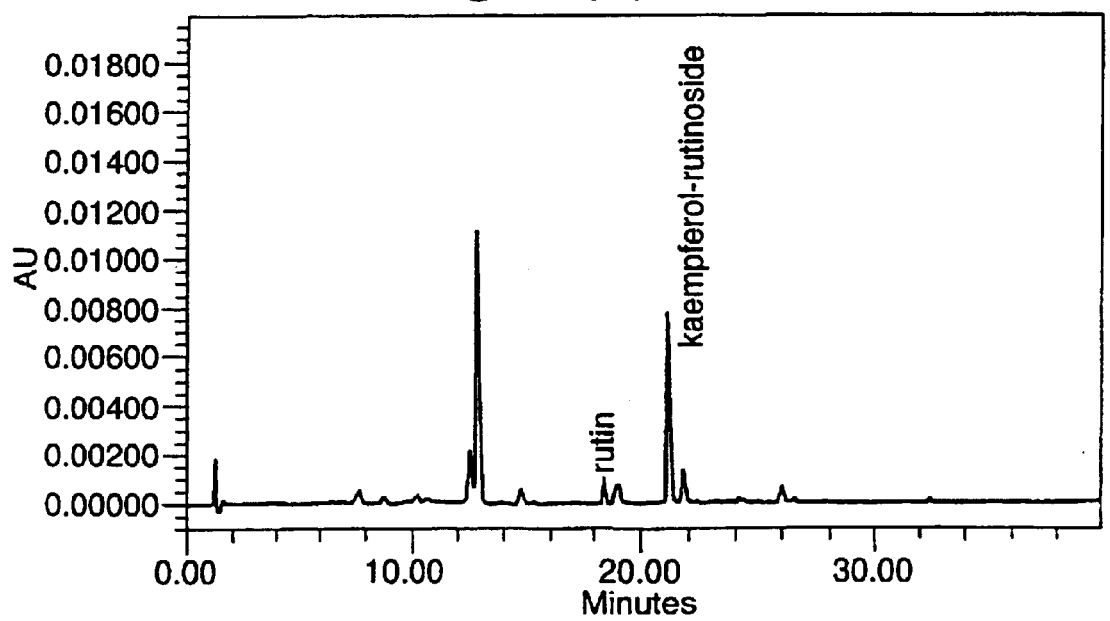

FIG. 13 shows typical HPLC chromatograms, recorded at 360 nm, of non-hydrolysed extracts of flesh tissue from red fruits of (A) an untransformed plant and (B) a plant transformed with pBBC300.

Figure 14A:
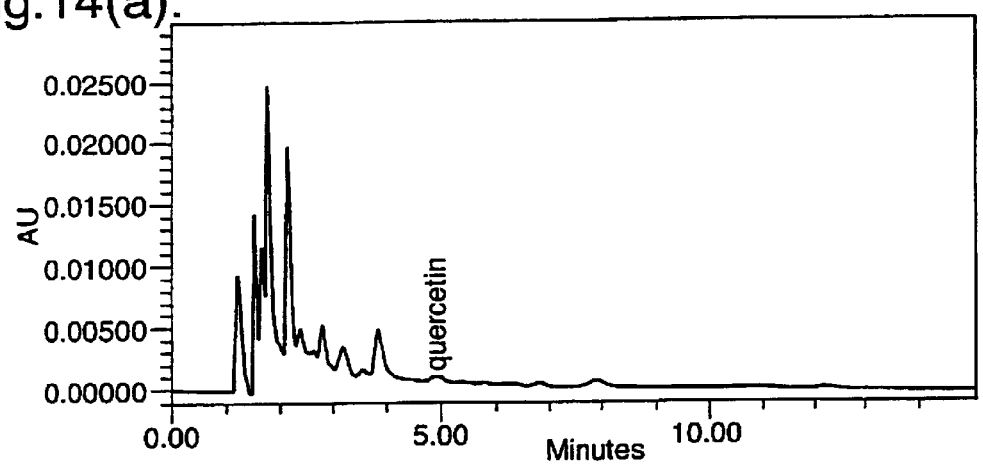
Figure 14B:
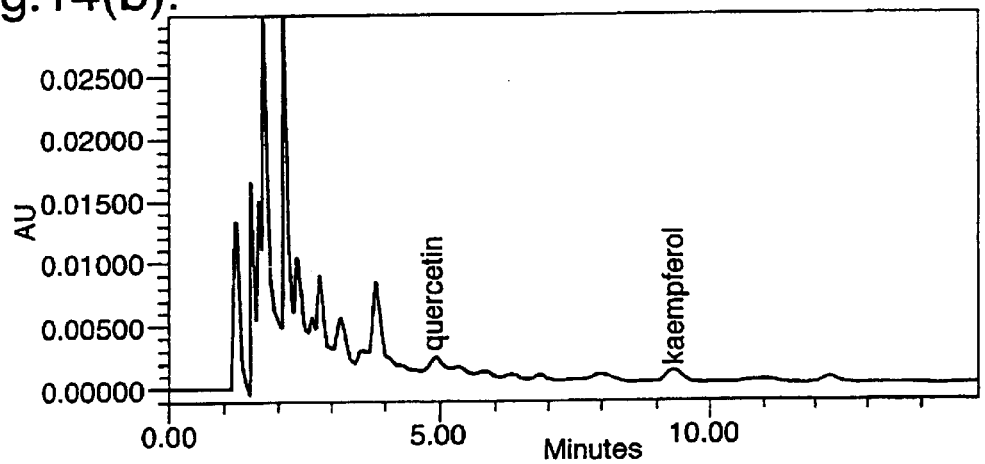
Figure 14C:
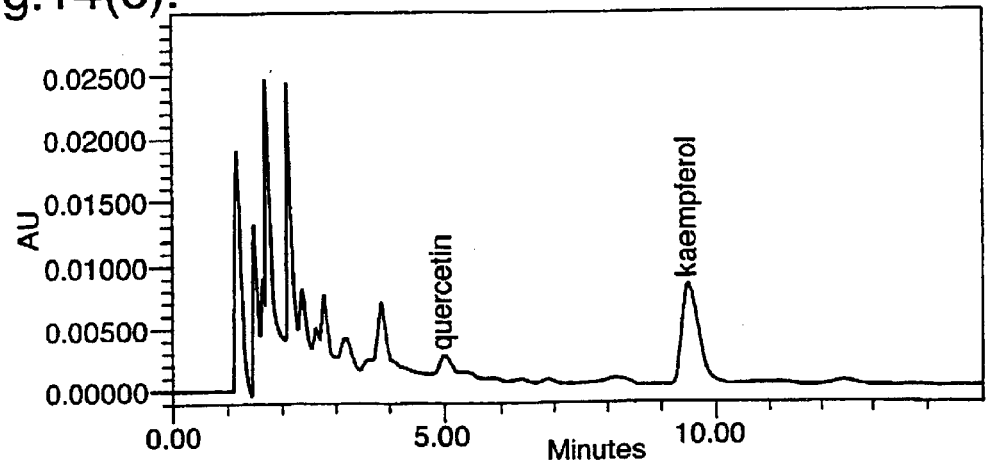

FIG. 14 shows the ripening-dependent accumulation of kaempferol-type flavonols in flesh of fruits from a plant transformed with pBBC300. HPLC Chromatograms recorded at 370 nm of hydrolysed extracts from fruits at (A) green, (B) turning and (C) red stage are shown.

Figure 15:
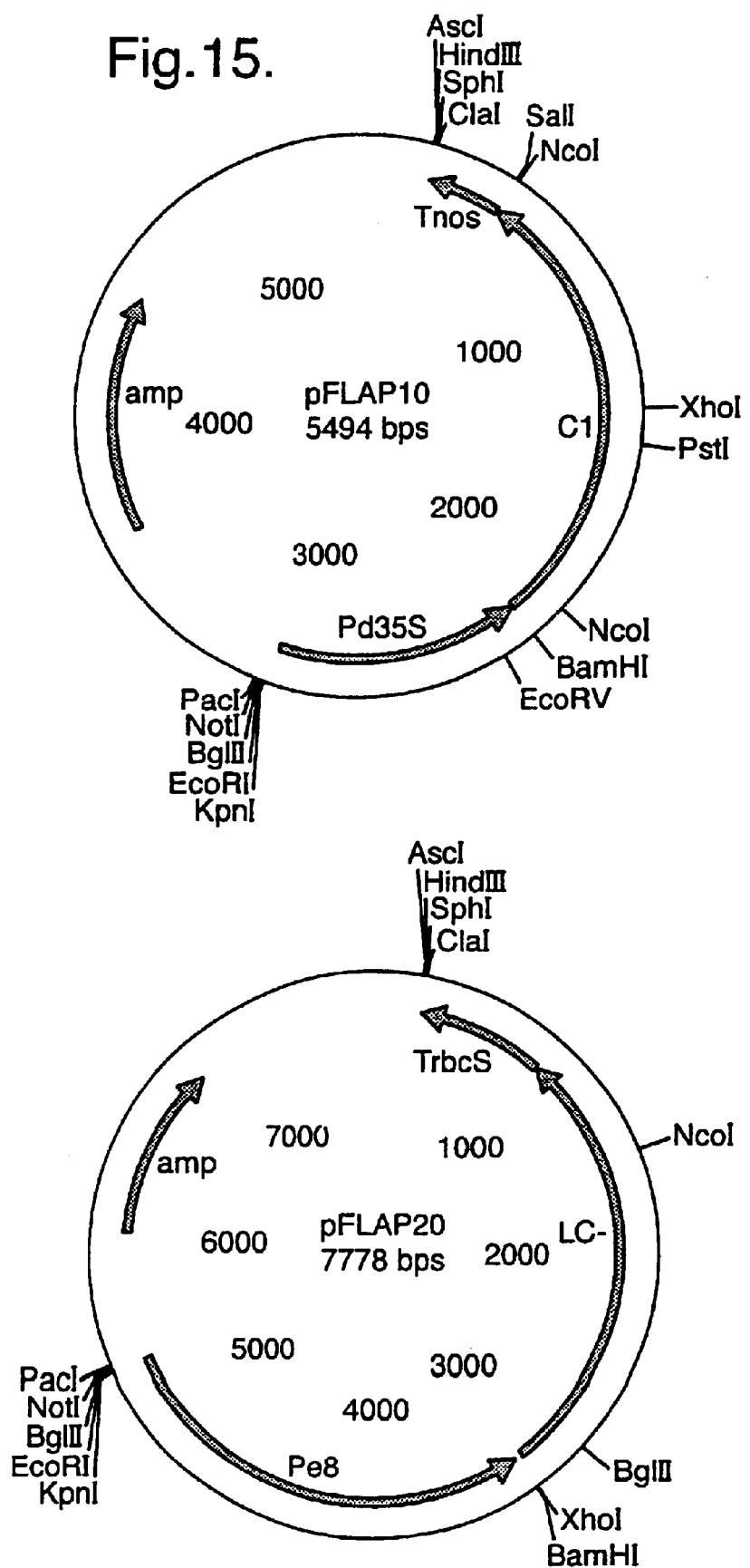
Figure 15:
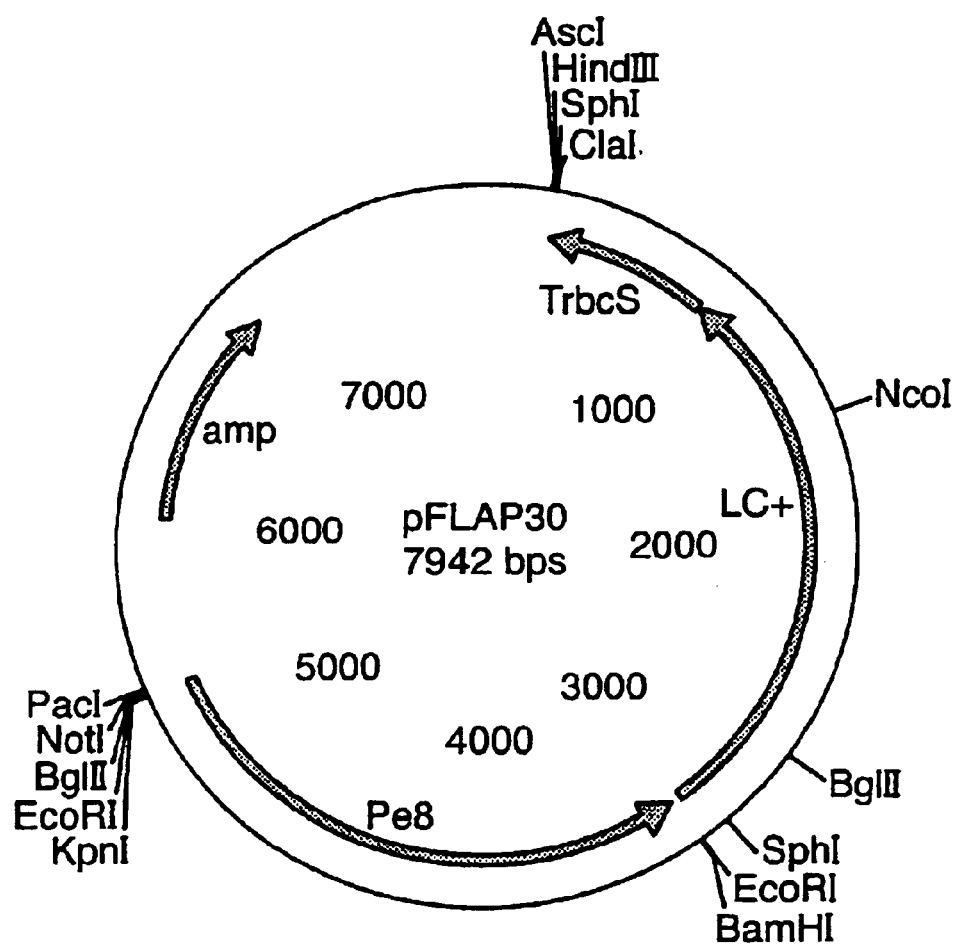

FIG. 15 shows restriction maps of plasmids pFLAP10, pFLAP20 and pFLAP30.

Figure 16:
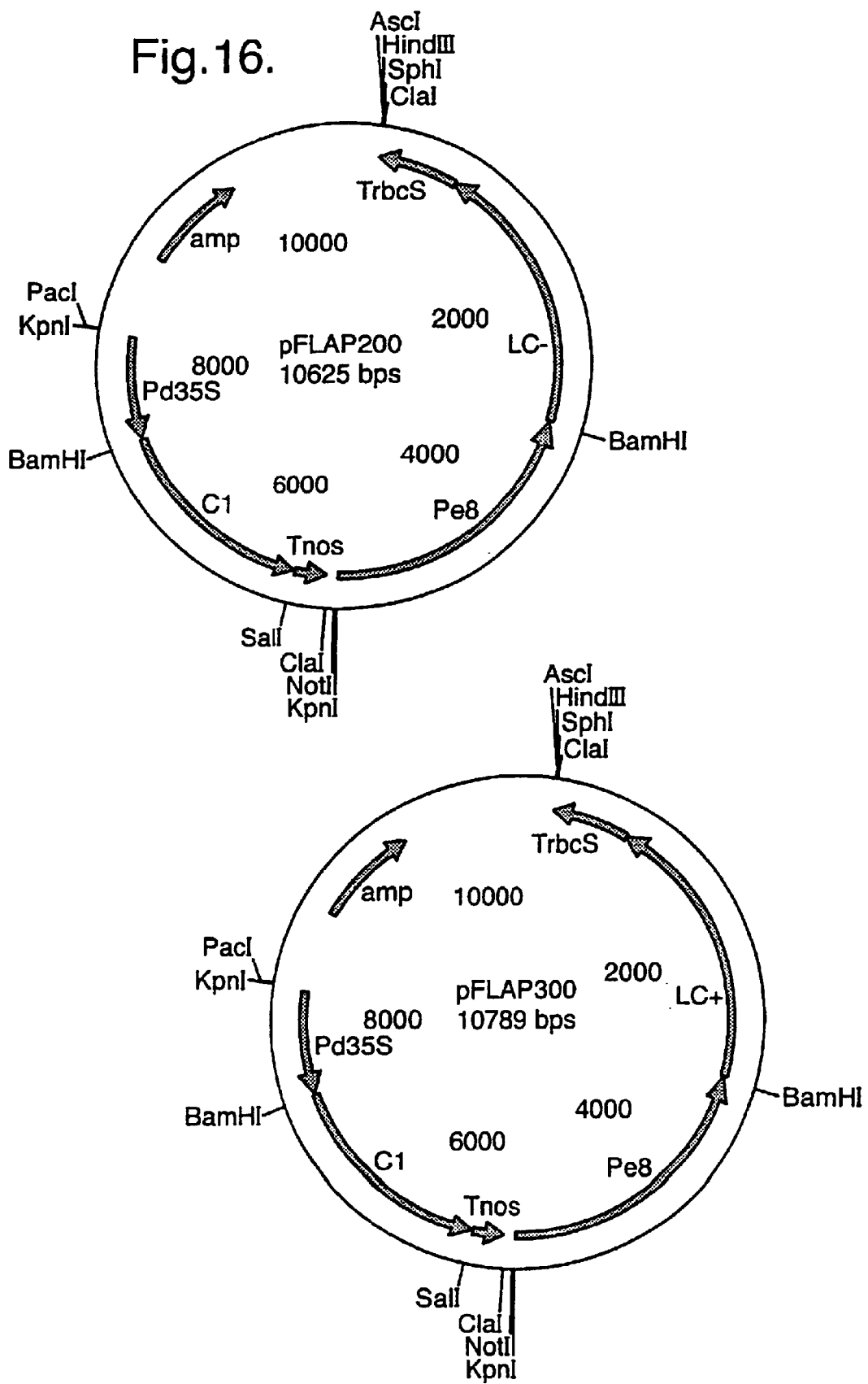

FIG. 16 shows restriction maps of plasmids pFLAP200 and pit pFLAP300.

Figure 17:
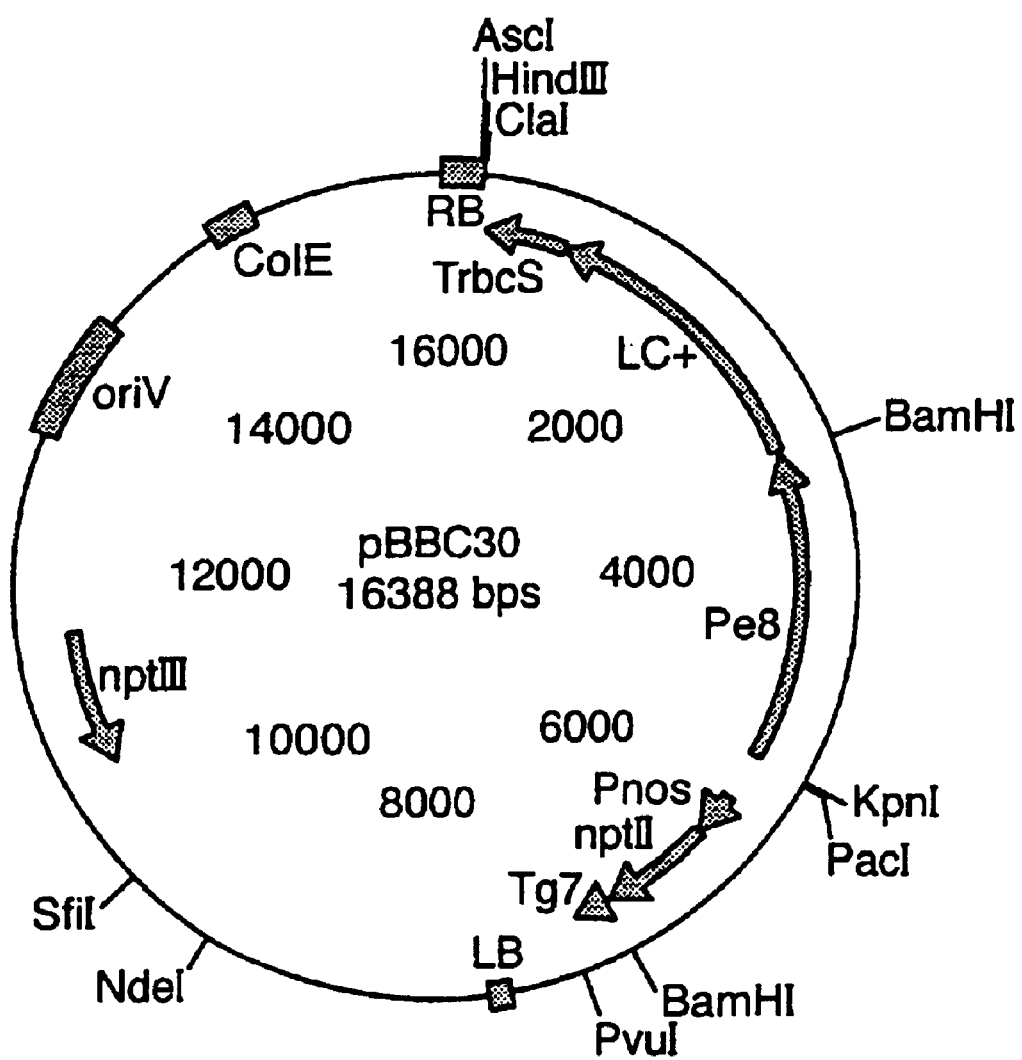

FIG. 17 shows restriction maps of plasmids pBBC10, pBBC20 and pBBC30.

Figure 18:
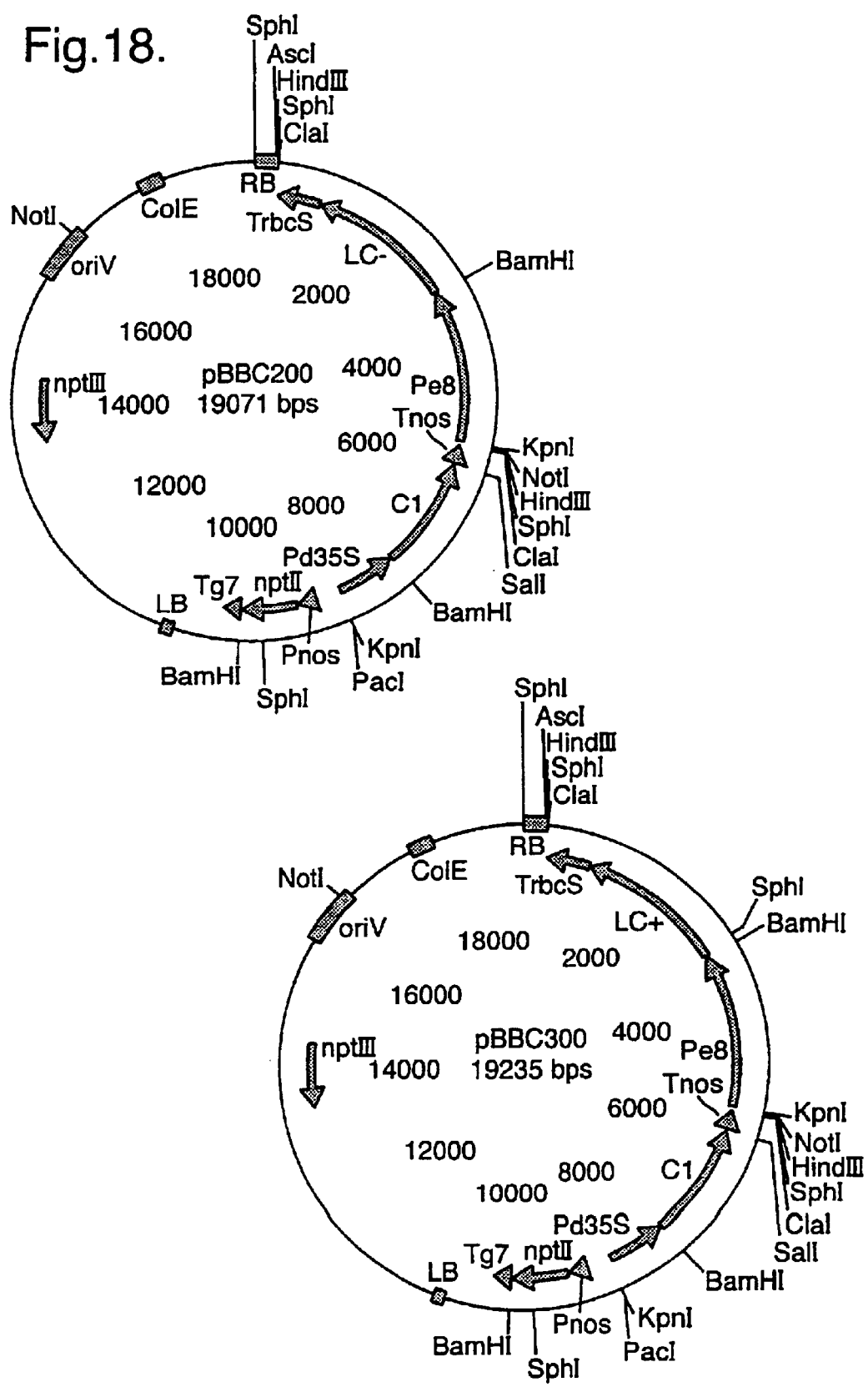

FIG. 18 shows restriction maps of plasmids pBBC200 and pBBC300.

Figure 19:
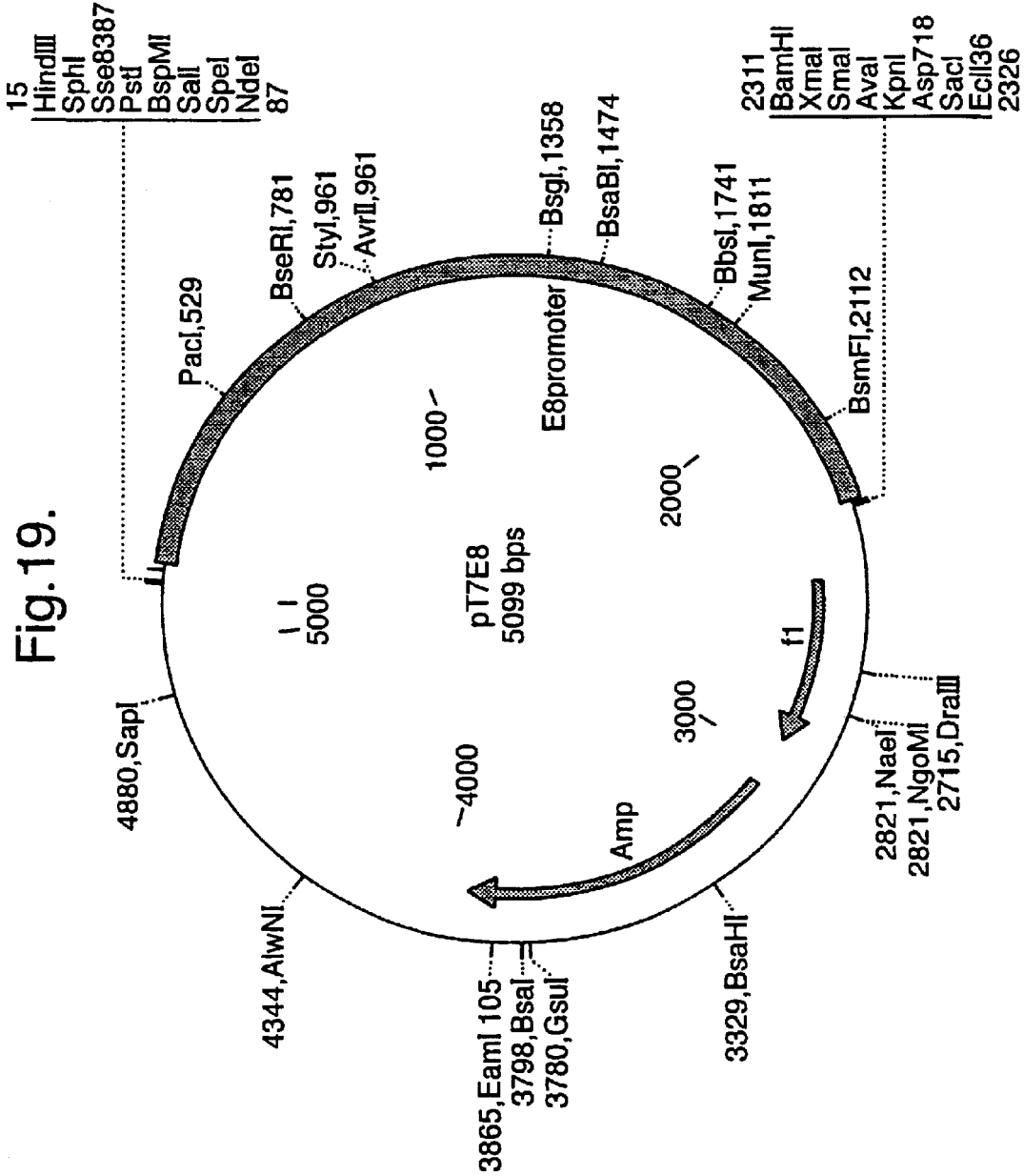

FIG. 19 shows a restriction map of plasmid pT7E8.

Figure 20:
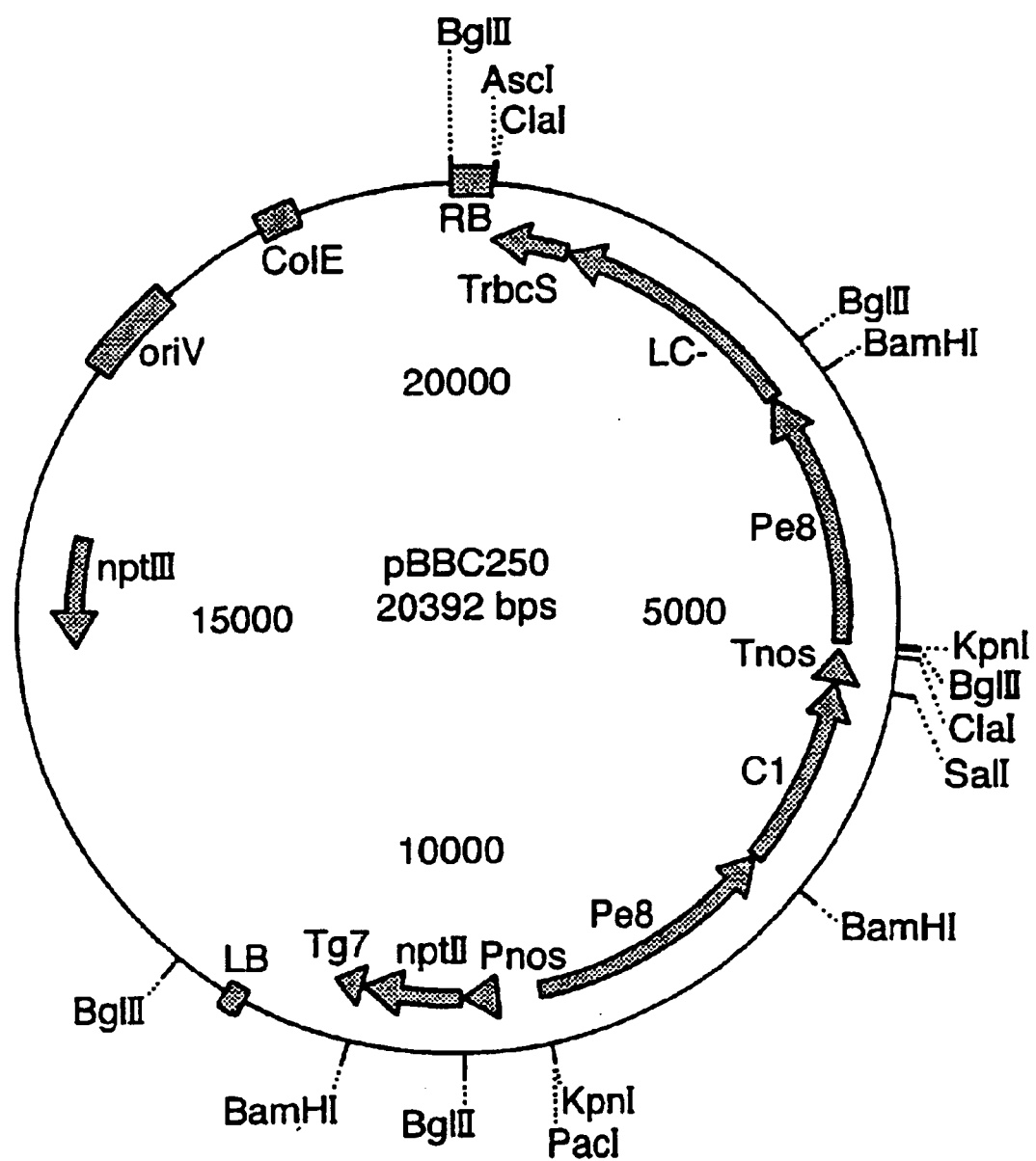

FIG. 20 shows a restriction map of plasmid pBBC250.

Figure 21:
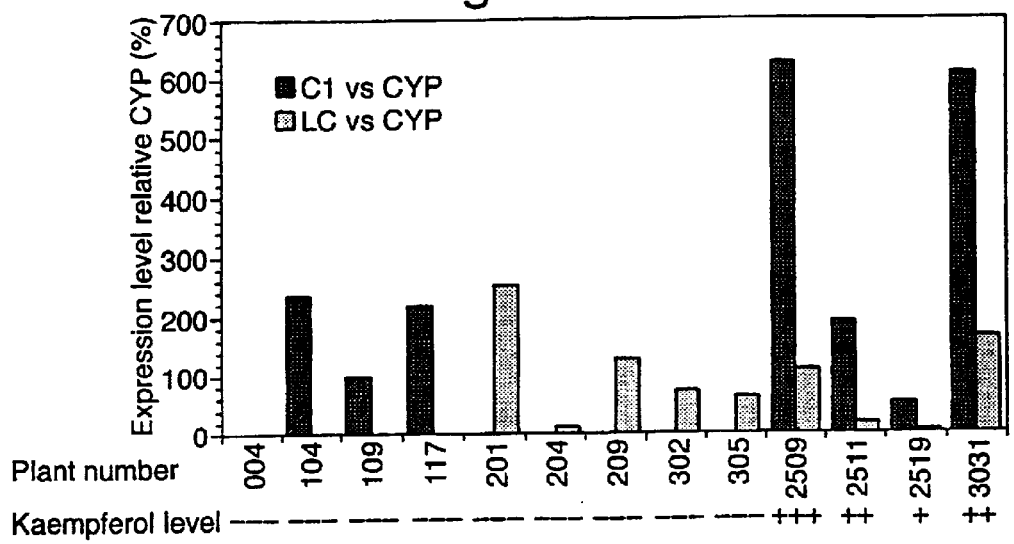

FIG. 21 shows the expression of the regulatory genes Lc and C1, relative to the constitutive gene cyp, in red fruits of a control plant (number 004), of plants transformed with the single gene constructs pBBC10 (numbered 100 onwards), pBBC20 (numbered 200 onwards) or pBBC30 (numbered 300 onwards), and of plants transformed with the double gene constructs pBBC250 (numbered 2500 onwards) or pBBC300 (number 3031). For each plant, the level of kaempferol measured in the fruits is given as well. ---: <2 mg/kg fresh weight; +: 2–10 mg/kg fresh weight: ++: 11–40 mg/kg fresh weight; +++: >40 mg/kg fresh weight.

Figure 22:
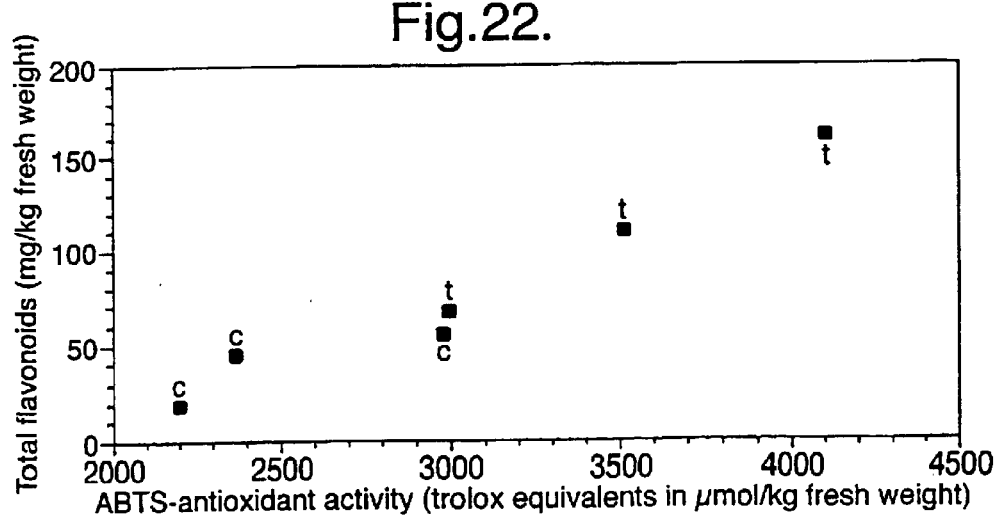

FIG. 22 shows the relation between total flavonoid level (quercetin, kaempferol and naringenin) and antioxidant activity (TEAC values) of red fruits of some control (c) and pBBC300-transformed (t) tomato plants.

Figure 23:
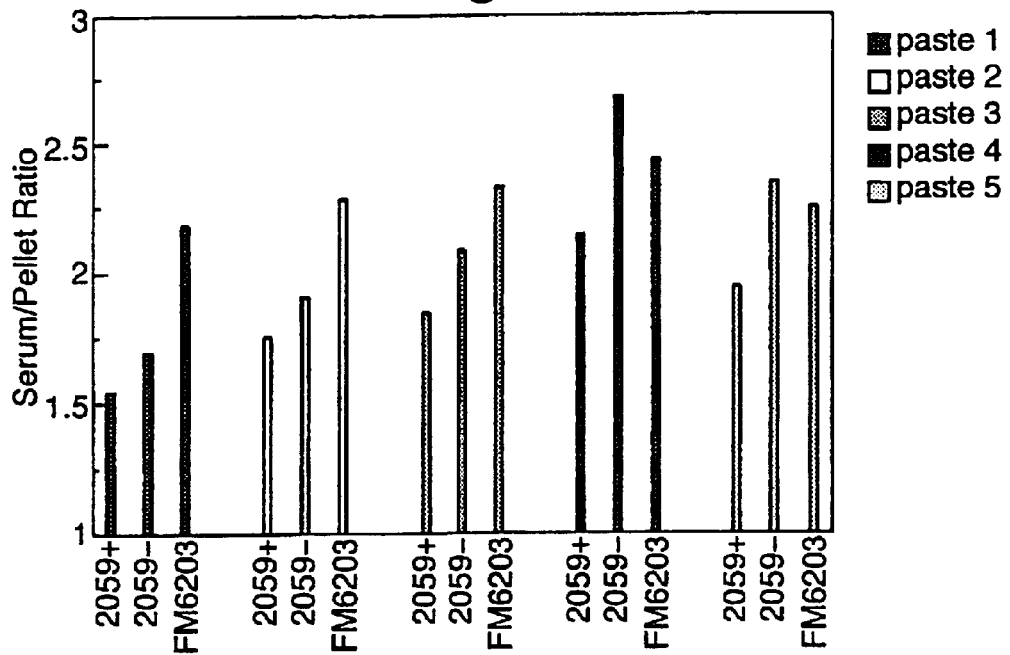

FIG. 23 shows serum pellet ratios for tomato pastes prepared from transformed tomatoes as compared to pastes prepared from control tomatoes.

Figure 24:
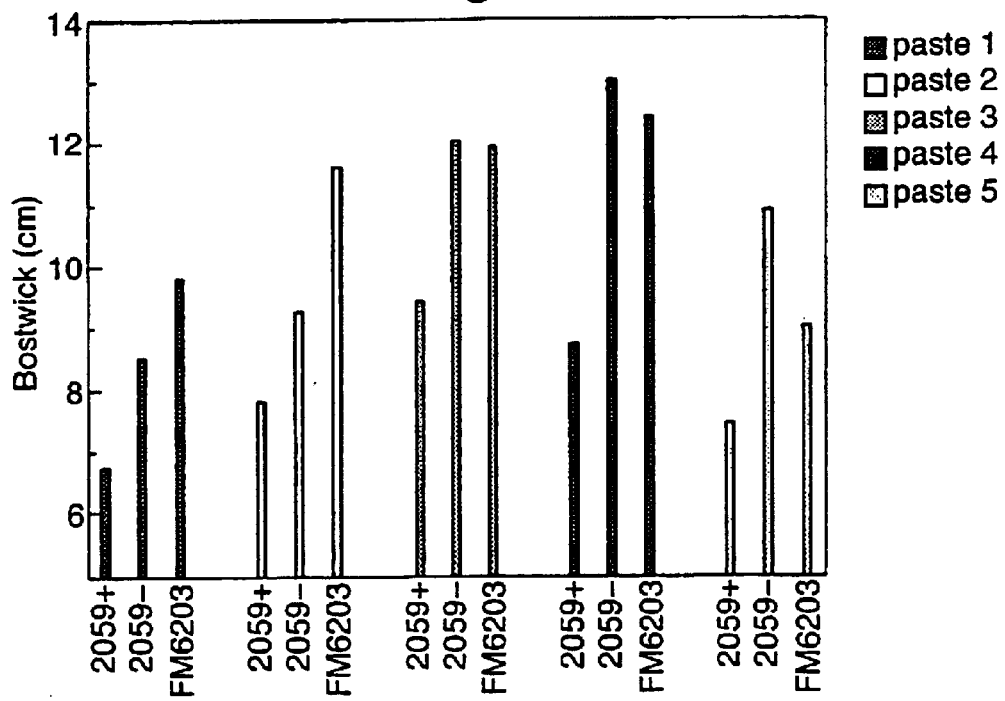

FIG. 24 shows a comparison of Bostwick values of tomato pastes prepared from transformed tomatoes as compared to pastes prepared from control tomatoes.

Figure 25:
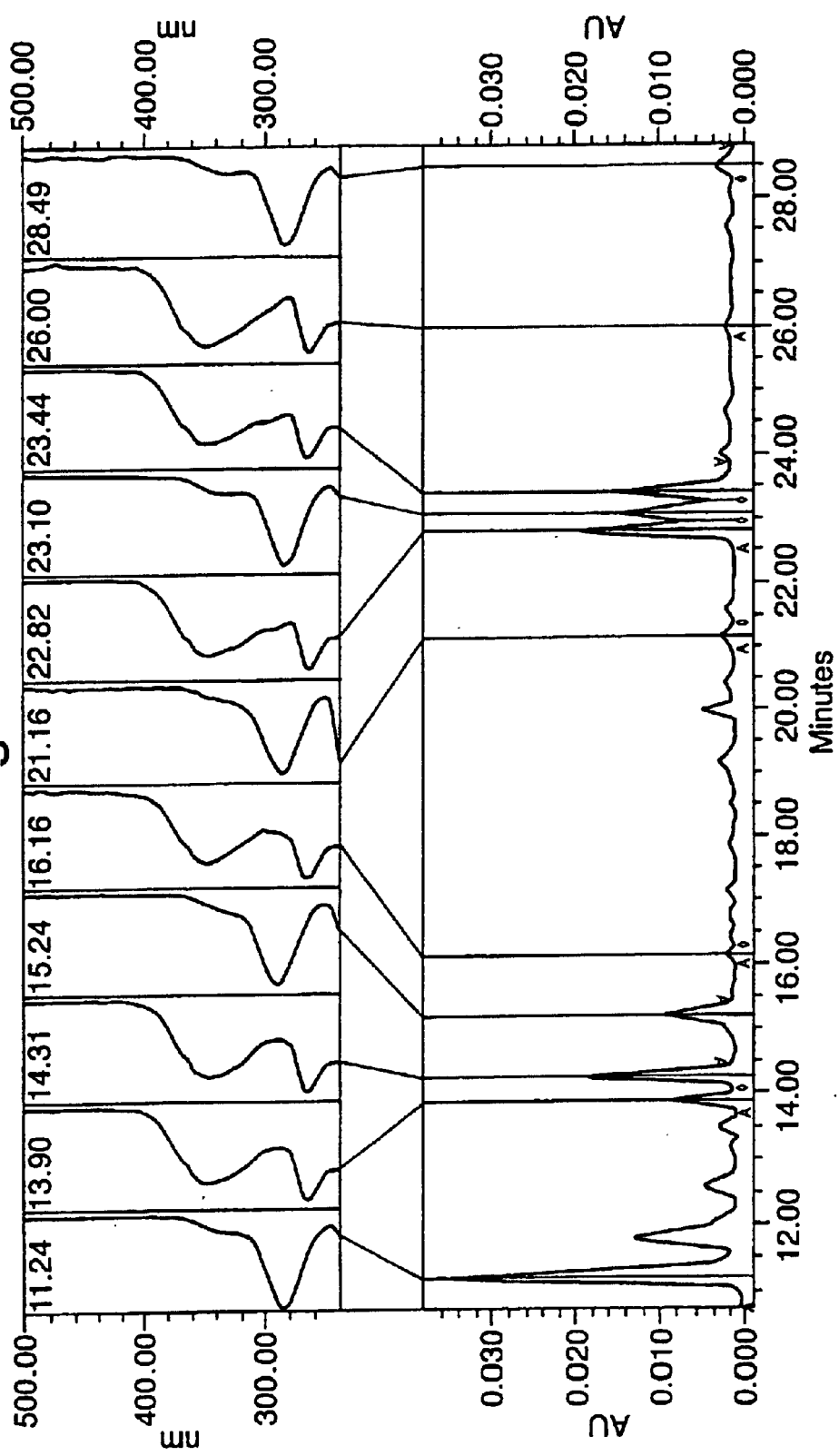

FIG. 25 shows a spectrum-index plot of a detail of a HPLC chromatogram, recorded at 280 nm, of non-hydrolysed extracts from whole red fruits of a pBBC300-transformed plant. The retention times and absorbance spectra of flavonoid species that were increased in the transformed plant are indicated in the upper panel.

FIG. 26 shows typical HPLC chromatograms, recorded at 360 nm, of non-hydrolysed extracts from whole red fruits of (A) an untransformed plant and (B) a plant transformed with pBBC300. Retention times and names of identified peaks are indicated.

FIG. 27 shows typical HPLC chromatograms, recorded at 280 nm, of non-hydrolysed extracts from whole red fruits of (A) an untransformed plant and (B) a plant transformed with pBBC300. Retention times and names of identified peaks are indicated.

Figure 28:
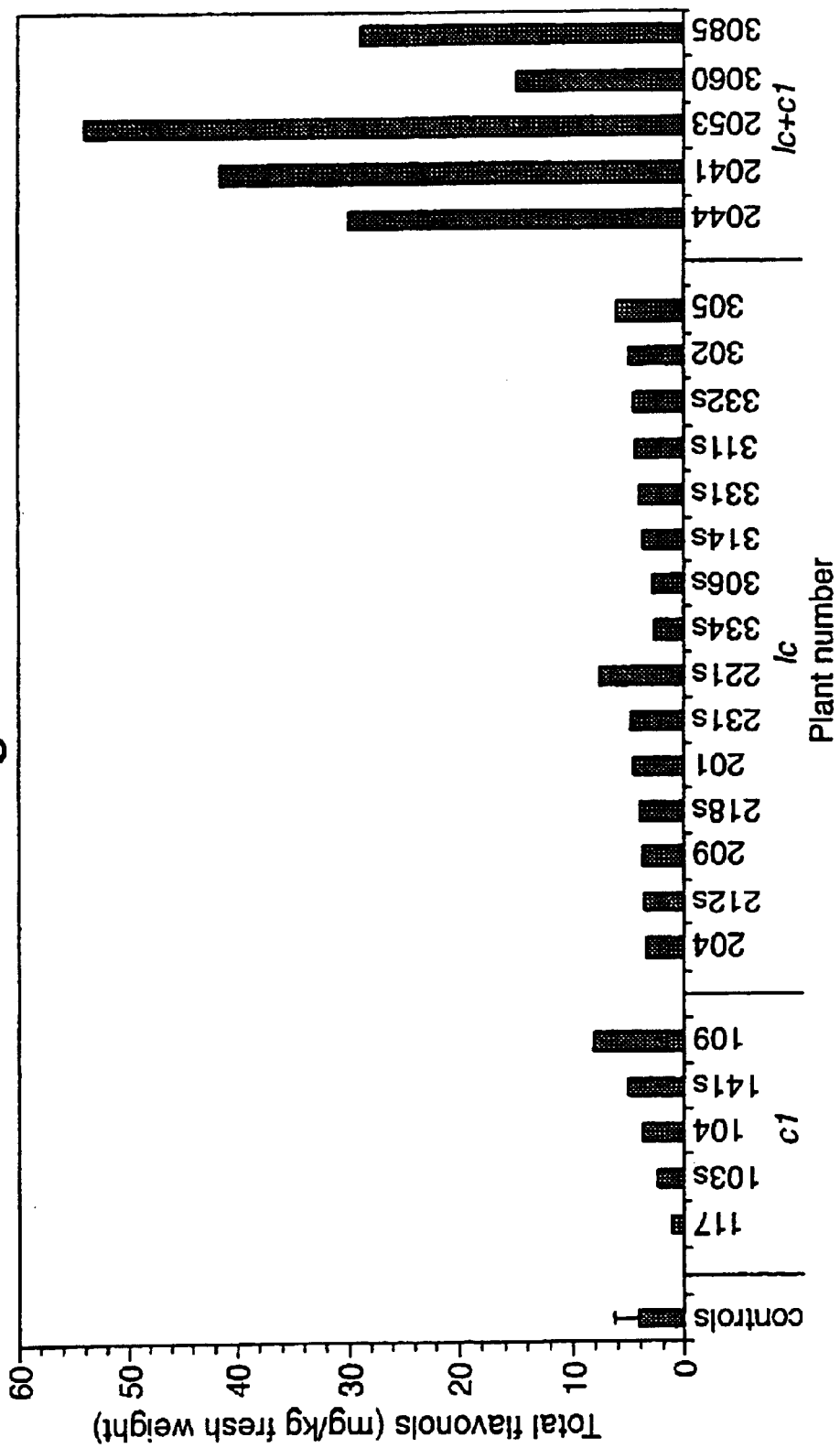

FIG. 28 shows the levels of total flavonols (quercetin plus kaempferol) in hydrolysed extracts of whole red fruits of untransformed control plants (left bar, mean±s.d., n=10), plants transformed with the single gene-constructs pBBC10 (numbered 100 onwards), pBBC20 (numbered 200 onwards) and pBBC30 (numbered 300 onwards), as well , as some plants transformed with the double gene-constructs pBBC200 (numbered 2000–2499) and pBBC300 (numbered 3000–3499).

Figure 29A:
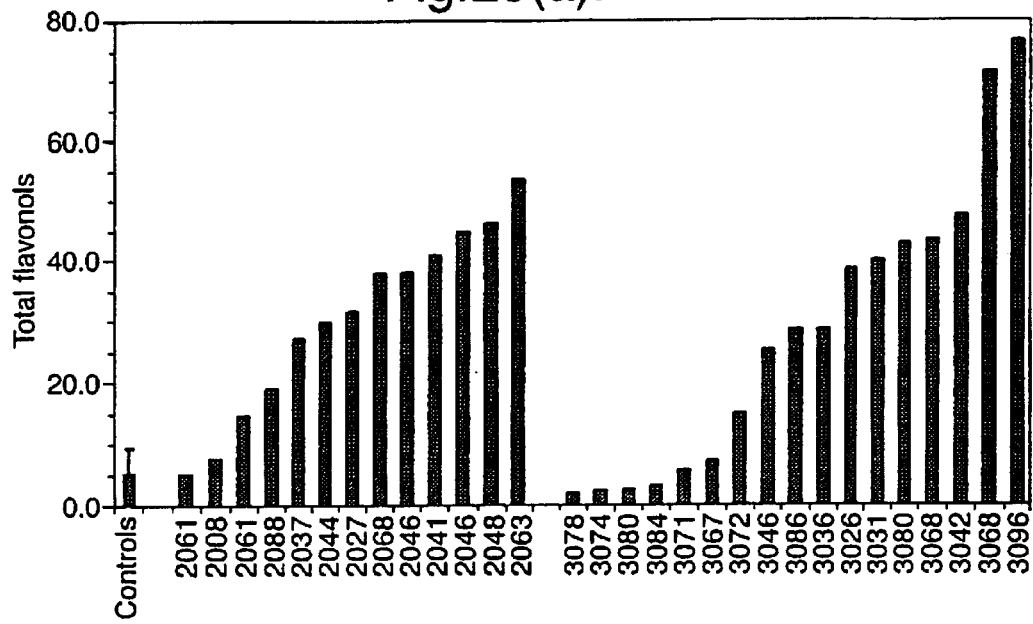
Figure 29B:
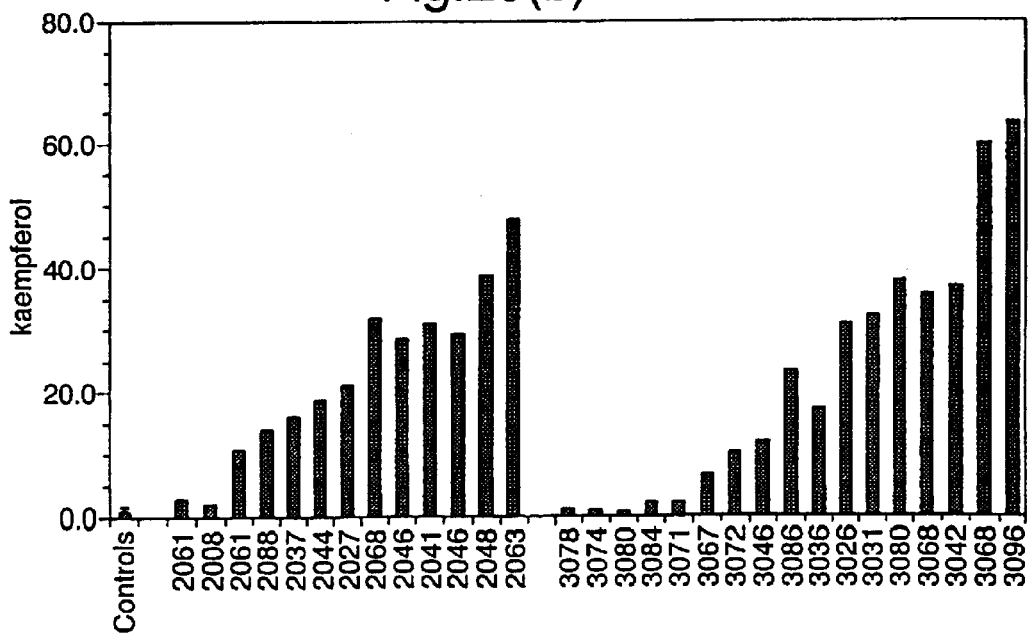
Figure 30A:
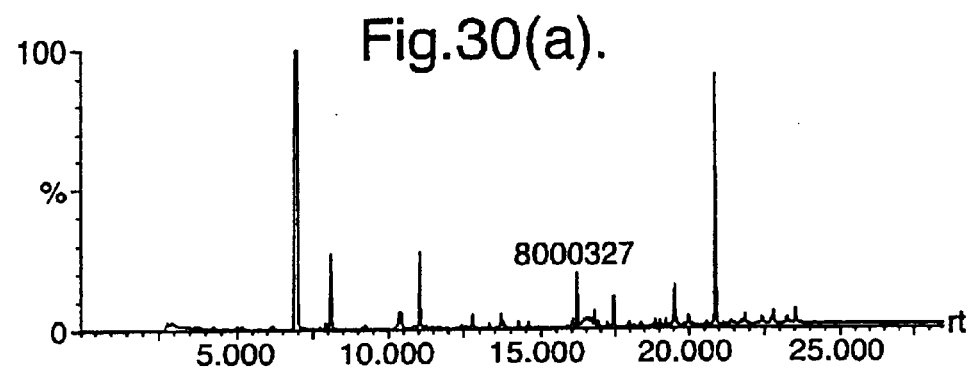
Figure 30B:
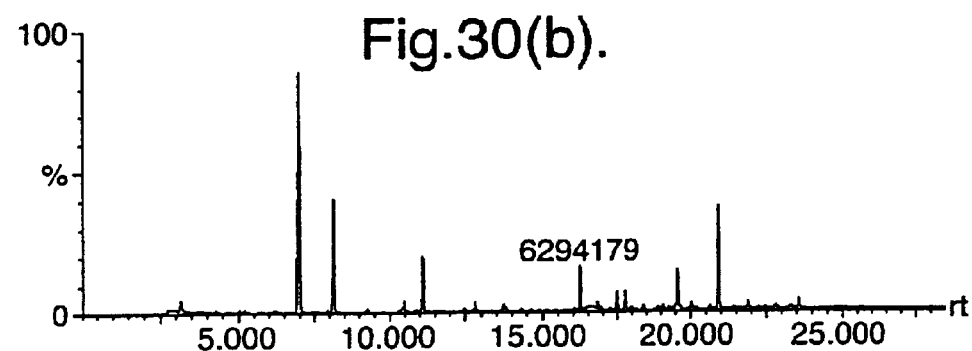
Figure 30C:
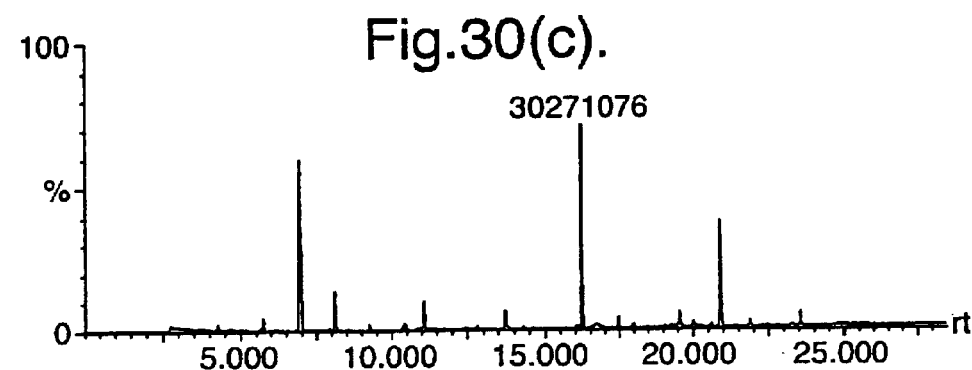
Figure 30D:
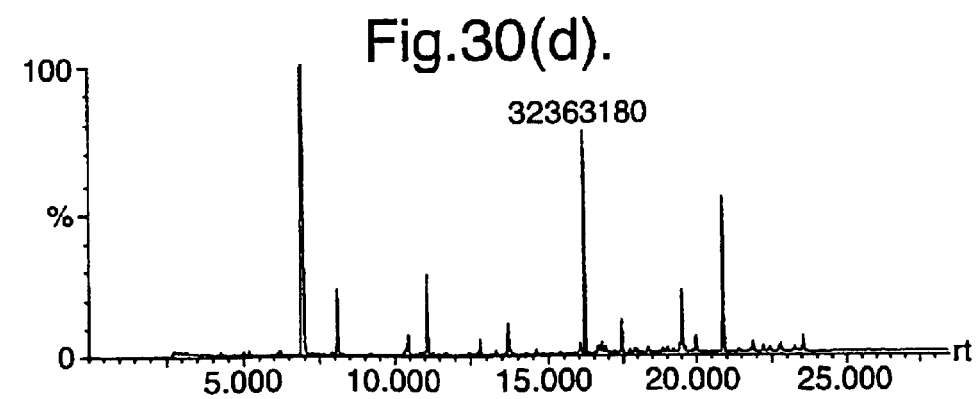

FIG. 29 shows levels of total flavonols (quercetin plus kaempferol), kaempferol, quercetin and naringenin measured by HPLC in whole fruits of control and transformed tomato plants. Flavonoid levels are expressed in mg/kg fresh weight and were calculated from hydrolysed extracts, i.e. naringenin is derived from hydrolysis of naringenin-glycosides (in transformants only) and from isomerization of narichalcone (both controls and transformants). First bar in each plot represents the levels of control plants (means±s.d., n=10).

FIG. 30 shows typical GC-MS chromatograms, total ion counts (TIC) recorded, of volatiles produced by red tomato fruits of (A) an untransformed control plant, (B) a plant transformed with pBBC20, (C) a plant transformed with pBBC10 and (D) a plant transformed with pBBC200. Arrow indicates the position (with integrated peak areas) of methylsalicylate. Y-axis: percentage TIC (100% 8×106); X-axis: retention time (minutes).

DETAILED DESCRIPTION OF THE INVENTION

As used herein, "plant" means a whole plant or part thereof, or a plant cell or group of plant cells. Preferably however the invention is particularly directed at transforming whole plants and the use of the whole plant or significant parts thereof, such as fruits, leaves or seeds.

A "flavonoid" or a "flavonol" may suitably be an aglycon or a glycoside.

A "gene" is a DNA sequence encoding a protein, including modified or synthetic DNA sequences or naturally occurring sequences encoding a protein, and excluding the 5' sequence which drives the initiation of transcription.

A "transcription factor" is a protein which can interact with a promoter and thereby influence the level of expression of a gene operably linked to that promoter. A sequence functionally equivalent thereto is any sequence which encodes a protein which has similar functional properties. It will be appreciated that functional equivalent sequences include but ar enot limited to gene fragments which still have similar functional properties and altered genes (e.g. mutated genes) which still have similar functional properties. Preferably there is a high degree of homology (eye-ball method) between the genes and their functional equivalents e.g. at least 60%, more preferred more than 80%, most preferred more than 95%.

"Operably linked to one or more promoters" means the gene, or DNA sequence, is positioned or connected to the promoter in such a way to ensure its functioning. The promoter is any sequence sufficient to allow the DNA to be transcribed. After the gene and promoter sequences are joined, upon activation of the promoter, the gene will be expressed.

A "construct" is a polynucleotide comprising nucleic acid sequences not normally associated in nature.

The present invention is based on the unexpected finding that levels of flavonoids other than- anthocyanins in plants, particularly edible plants such as tomato plants, can be manipulated by incorporating into the plant two or more genes encoding transcription factors for flavonoid biosynthesis.

Preferably the plants are stably transformed with the two genes encoding transcription factors e.g. by using genetic modification routes.

The method of the invention may be advantageously used for increasing flavonoid levels other than anthocyanins in a broad variety of plants. Preferably the invention its applied to edible plants, more in particular food plants which are normally used for food purposes. Examples of food plants are vegetables such as a tomato plant, spinach, a pea plant, broccoli, cauliflower, asparagus and potato plant, fruit-bearing plants such as a strawberry plant, oil producing plants such as sunflower, soybean and rape, or extractable plants such as tea plants.

Especially advantageously the present invention can be applied to oil producing plants and vegetables. Most preferably the method of the invention is applied to tomatoes.

Advantageously, by means of the invention, levels of flavonoids, more particularly flavonols, in plants, may be increased. Typically it is preferred that the increase of flavonoids other than anthocyanins is apparent in at least a part of the plants. For example for vegetables it is preferred that the flavonoids other than anthocyanins are increased in those parts of the vegetable that are normally eaten. For oil producing plants the flavonoids other than anthocyanins are preferably increased in the oil producing parts e.g. the sunflower seed or the soy-bean.

Preferably the increase of the levels of flavonoids other than anthocyanin and/or the increase in the level of flavonols in the plant as a whole or the desired, normally eaten, part thereof is increased by at least two-fold, more preferred at least five-fold, most preferred at least ten-fold as compared to similar plants which have not been transformed in accordance to the invention.

Moreover, it has been found that the level of flavonoids other than anthocyanins, in particular the level of flavonols, may be increased in specific parts of the plants. For example for plants of which the leaves are normally eaten or used in food products such as spinach and tea, it is advantageous that the level of flavonoids other than anthocyanins, in particular flavonols are increased in the leaves. For fruit-bearing plants such as tomato, strawberry etc it is advantageous that the level is increased in the fruit, for plants with edibe flowers e.g. broccoli and cauliflower it is advantageous that the level is increased in the flower, for plants with edible stems such as asparagus it is advantageous that the level is increased in the stem, for edible seeds, such as peas, sunflower seed or rapeseed it is advantageous that the level is increased in the seed etc. It has been found that typically the type and choice of one or more of the regulatory sequences for the genes encoding the transcription factors can provide the desired increase in specific parts of the plants.

Specifically it has been found that it is possible to increase the level of flavonoids other than anthocyanins, particularly flavonols in tomato fruit, and even more surprising in the in the flesh of tomato fruit, a tissue that does not normally contain flavonoids, thereby producing tomatoes with enhanced nutritional, preservative and flavour characteristics.

Preferably the level of flavonols in the flesh of the tomato is at least 2 mg/kg (fresh weight), more preferred at least 10 mg/kg (fresh weight), most preferably more than 30 mg/kg (fresh weight).

A further advantageous embodiment of the invention relates to the increase in the level of flavonoids other than anthocyanins in all or the desired parts of the plant, whereby the level of anthocyanins are not unduly increased such that the colour of the plant or the desired part thereof remains the same.

Preferably therefore the level of anthocyanins in the plant as a whole or in the desired part thereof (particularly the fruit) is similar to the level in the untranformed plant, for example the level in transformed plants or parts thereof is less than 2 times the level in untransformed plants, more preferably less than 1.5 times, more preferred about the same or less.

Some plants or parts thereof do normally not contain detectable levels of anthocyanins. For example in tomato-plants the peel and flesh of the fruit are normally substantially free from anthocyanins. In preferred embodiments of the invention the level of anthocyanins in such parts, for example the peel and/or the flesh of the tomato fruit, of transformed plants of the invention is therefore equally low e.g. less than 2 mg/kg fresh weight, more preferred less than 1 mg/kg fresh weight, most preferably substantially free from anthocyanins.

It will be appreciated that the invention extends to any plant which is amenable to transformation. Suitable plants include peas, spinach and tea. A particularly preferred plant for use according to the invention is the tomato plant.

Preferably, a combination of genes encoding transcription factors for flavonoid biosynthesis is employed. Suitably, the invention combines the use of a gene encoding a protein within the myb family of transcriptional regulators (see Martin et al, Trends in Genetics, (1997), 13, 67–73) together with a gene encoding a protein within the myc family of transcriptional regulators (see Ludwig et al, Cell, (1990), 62, 849–851). Examples of myb type transcription factors are myb305, myb308, myb340, P1 from maize and C1 from maize. Examples of myc type transcription factors are DEL, Lc, R from maize and B from maize. A particularly suitable combination of genes for use according to the invention comprises the gene encoding the maize C1 myb-type transcription factor together with the gene encoding the maize Lc myc-type transcription factor but it will be appreciated that the invention is not limited to this combination and extends to the use of any combination of genes encoding transcription factors for flavonoid biosynthesis, such as myb305, myb340, and Delila from *antirrhinum* (see Mooney et al, above and Moyano et al, Plant Cell, 8 (1996), 1519–1532).

It will be further appreciated that the sequence encoding a transcription factor for flavonoid biosynthesis may be a genomic or cDNA clone, or a sequence which in proper reading frame encodes an amino acid sequence which is functionally equivalent to the amino acid sequence of the transcription factor encoded by the genomic or cDNA clone. By "functionally equivalent" is meant any DNA sequence which is capable of similar biological activity. A functional derivative can be characterised by an insertion, deletion or a substitution of one or more bases of the DNA sequence, prepared by known mutagenic techniques such as site-directed mutagenesis. The functionality can be evaluated by routine screening assays, for example, by assaying the flavonoid content of the resulting transgenic plant.

Gene sequences encoding transcription factors for flavonoid biosynthesis for use according to the present invention may suitably be obtained from plants, in particular higher plants as these generally possess a flavonoid biosynthetic pathway. Myb and myc-type transcription factor genes involved in the control of flavonoid biosynthesis have been isolated from various plant species such as maize (see, for example, Lloyd et al, above), *antirrhinum* (see, for example, Goodrich et al, Cell, 68, (1992), 955–964) and *Petunia* (see Quattrocchio et al, Plant Cell, 5, (1993), 1497–1512). In the context of the present invention, the maize plant is a particularly preferred source. Alternatively, equivalent genes could be isolated from plant gene libraries, for example by hybridisation techniques with DNA probes based on known transcription factor genes.

The gene sequences of interest will be operably linked (that is, positioned to ensure the functioning of) to one or more suitable promoters which allow the DNA to be transcribed. Suitable promoters, which may be homologous or heterologous to the gene (that is, not naturally operably linked to a gene encoding a transcription factor for flavonoid biosynthesis), useful for expression in plants are well known in art, as described, for example, in Weising et al, (1988), Ann. Rev. Genetics, 22, 421–477). Promoters for use according to the invention may be inducible, constitutive, or tissue-specific or have various combinations of such characteristics.

Preferably at least one of the genes is linked to a promoter which is either non-constitutive and/or tissue specific. It is believed that the use of at least one constitutive promoter is advantageous in that it may prevent the formation of very high (lethal) doses of one or more ingredients in the flavonoid pathway. The use of tissue-specific promoters may equally be advantageous in that they may lead be used to introduce or enhance formation of flavonoids other than anthocyanin in specific desired parts of the plant, for example those parts that are intended to be eaten (e.g. leaf-specific for spinach and tea, seed-specific for oil producing plants and peas, flower specific for broccoli and cauliflower, stem specific for asparagus, fruit specific for tomato).

Useful promoters include, but are not limited to constitutive promoters such as carnation etched ring virus (CERV), cauliflower mosaic virus (CaMV) 35S promoter, or more particularly the double enhanced cauliflower mosaic virus promoter, comprising two CaMV 35S promoters in tandem (referred to as a "Double 35S" promoter).

It may be desirable to use a tissue-specific or developmentally regulated promoter instead of a constitutive promoter in certain circumstances. A tissue-specific promoter induces or increases expression of the transcription factor for flavonoid biosynthesis in certain desired tissues, preferably without unduly affecting expression in other tissues. By way of illustration, promoters used in overexpression of the maize Lc transcription factor in tomato plants will preferably be tissue specific, especially fruit-specific. Overexpression of Lc in vegetative tissues of tomato plants is known to be deleterious to the health of, the plant (see Goldsbrough et al, above). Suitable fruit-specific promoters include the tomato E8 promoter (Deikman et al, (1988), EMBO J, 7, 3315–3320), 2A11 (Van Haaren et al, Plant Mol Biol, 21, 625–640), E4 (Cordes et al, (1989), Plant Cell, 1, 1025–1034) and PG (Bird et al, (1988), Plant Mol. Biol., 11, 651–662,) Nicholass et. al. (1995), Plant Molecular Biology, 28, 423–435. Both transcription factors for use according to the method of the invention may conveniently operably be linked to the same or different fruit-specific promoters.

According to a preferred embodiment of the method of the invention, however, a gene encoding a first transcription factor for flavonoid biosynthesis is operably linked to a constitutive promoter whilst a gene encoding a second transcription factor for flavonoid biosynthesis is operably linked to a non-constitutive or tissue-specific promoter e.g. a fruit specific promoter. The combination of a constitutive and fruit-specific promoter helps to ensure that the desired flavonoids are produced mainly in the fruit. An additional advantage in the use of such a combination, is that possible inhibitory effects ("gene silencing") on the expression of the introduced genes arising from the use of the same promoter are avoided.

In a particularly preferred embodiment, a gene encoding the maize C1 transcription factor operably linked to the constitutive double 35S CaMV promoter is combined with a maize Lc transcription factor operably linked to the fruit-specific tomato E8 promoter.

It will be appreciated that overexpression of genes encoding transcription factors for flavonoid biosynthesis according to the method of the invention may result-in the accumulation of both anthocyanins and flavonoids other than anthocyanins, particularly if the transcription factors operate at a position along the flavonoid biosynthesis pathway before the respective flavonol and anthocyanin pathways diverge. This may sometimes undesirable as the formation of anthocyanins not only results in the production of aesthetically unpleasing purple coloured fruits, but may also limit the production of flavonols. In a preferred embodiment of the invention, therefore those genes for encoding transcription factors are chosen which on the one hand lead to an increase of the level of flavonoids other than anthocyanin in the whole plant or the desired tissues, but on the other hand do not substantially enhance the level of anthocyanins in said plant or the desired tissues thereof. In a further embodiment, this may be accomplished by blocking the route to expression of anthocyanins for example by an additional step comprising antisense suppression of dihydroflavonol reductase (DFR), the enzyme catalysing the final step in the production of anthocyanins. Alternatively, transcription factors may be overexpressed in a mutant line, such as a tomato line which is deficient in DFR activity, for example, the anthocyanin without (aw) mutant which is described by Goldsbrough et al, Plant Physiol, (1994), 105, 491–496.

Furthermore, accumulation of flavonoids may also be inhibited by the rate of production of the amino acid phenylalanine, the primary substrate in the synthesis of phenylpropanoids and subsequent flavonoids. In order to increase phenylsynthesis, genes encoding enzymes of the phenylalanine pathway that are insensitive to feed-back regulation may be introduced as an optional additional step.

Plants incorporating a combination of genes encoding transcription factors for flavonoid biosynthesis according to the invention may be produced by crossing one plant expressing one transcription factor of the pair with another plant expressing the other transcription factor using conventional cross-breeding techniques. The respective starting materials may be produced by conventional plant transformation techniques well known in the art.

Preferably, however, the desired gene sequences, operably linked to respective suitable promoters, are fused to appropriate expression sequences to provide an expression cassette functional in a plant cell which can be introduced into a plant cell by any conventional plant transformation method.

Accordingly, the invention provides in a further aspect an expression cassette comprising as operably linked components in the 5'-3' direction of transcription, two or more units each comprising a promoter functional in a plant cell, a gene encoding a transcription factor for flavonoid biosynthesis and a transcriptional and translational termination regulatory region functional in a plant cell.

The promoter and termination regulatory regions will be functional in the host plant cell and may be heterologous (that is, not naturally occurring) or homologous (derived from the plant host species) to the plant cell and the gene. Suitable promoters which may be used are described above.

The termination regulatory region may be derived from the 3' region of the gene from which the promoter was obtained or from another gene. Suitable termination regions which may be used are well known in the art and include *Agrobacterium tumefaciens* nopaline synthase terminator (Tnos), *Agrobacterium tumefaciens* mannopine synthase terminator (Tmas) and the CaMV 35S terminator (T35S). Particularly preferred termination regions for use according to the invention include the tobacco ribulose bisphosphate carboxylase small subunit termination region (TrbcS) or the Tnos termination region.

Such gene constructs may suitably be screened for activity by transformation into a host plant via *Agrobacterium* and screening for flavonoid levels.

Conveniently, the expression cassette according to the invention may be prepared by cloning the individual promoter/gene/terminator units into a suitable cloning vector. Suitable cloning vectors are well known in the art, including such vectors as pUC (Norrander et al, (1983, Gene 26, 101–106), pEMBL (Dente et al (1983), Nucleic Acids Research, 11, 1645–1699), pBLUESCRIPT (available from Stratagene), PGEM (available from Promega) and pBR322 (Bolivar et al, (1977), Gene, 2, 95–113). Particularly useful cloning vectors are those based on the pUC series. The cloning vector allows the DNA to be amplified or manipulated, for example by joining sequences. The cloning sites are preferably in the form of a polylinker, that is a sequence containing multiple adjacent restriction sites, so as to allow flexibility in cloning.

In a particularly preferred embodiment, the individual promoter/gene/terminator units are cloned into adjacent pairs of restriction sites in a suitable cloning vector. The individual promoter/gene/terminator units may conveniently be constructed using a cloning vector comprising the same restriction sites as are present in the cloning vector for the multiple unit construct but wherein the restriction sites are arranged in nested fashion rather than sequentially.

Suitably, the nucleotide sequences for the genes may be extracted from the Genbank nucleotide database and searched for restriction enzymes that do not cut. These restriction sites may be added to the genes by conventional methods such as incorporating these sites in PCR primers or by sub-cloning.

Preferably the DNA construct according to the invention is comprised within a vector, most suitably an expression vector adapted for expression in an appropriate host (plant) cell. It will be appreciated that any vector which is capable of producing a plant comprising the introduced DNA sequence will be sufficient.

Suitable vectors are well known to those skilled in the art and are described in general technical references such as Pouwels et al, cloning Vectors. A laboratory manual, Elsevier, Amsterdam (1986). Particularly suitable vectors include the Ti plasmid vectors.

Transformation techniques for introducing the DNA constructs according to the invention into host cells are well known in the art and include such methods as microinjection, using polyethylene glycol, electroporation, or high velocity ballistic penetration. A preferred method for use according to the present invention relies on *agrobacterium*—mediated transformation.

After transformation of the plant cells or plant, those plant cells or plants into which the desired DNA has been incorporated may be selected by such methods as antibiotic resistance, herbicide resistance, tolerance to amino-acid analogues or using phenotypic markers.

Various assays may be used to determine whether the plant cell shows an increase in gene expression, for example, Northern blotting or quantitative reverse transcriptase. PCR (RT-PCR). Whole transgenic plants may be regenerated from the transformed cell by conventional methods. Such transgenic plants having improved flavonoid levels may be propagated and crossed to produce homozygous lines. Such plants produce seeds containing the genes for the introduced trait and can be grown to produce plants that will produce the selected phenotype.

In accordance with a particular embodiment of the invention, the cloning vectors plasmid pUCM2 and pUCM3 were prepared by modifying the cloning vector pUCAP (Van Engelen et al, (1995), Transgenic Research, 4, 288–290). Multiple cloning sites in these plasmids were constructed by insertion of synthetic adapters containing the restriction sites needed. Each individual gene construct encoding a transcription factor for flavonoid biosynthesis is prepared in pUCM2. Generally, each promoter was cloned as a KpnI/BamHI fragment, each structural gene as a BamHI/SalI fragment and each terminator region as a SalI/ClaI fragment, such that each individual gene fusion was made as a KpnI/ClaI fragment. By using restriction sites outside of KpnI and ClaI the individual gene fusions can be cloned behind each other in plasmid pUCM3, which contains the restriction sites of pUCM2 but in a different order. Using the two unique restriction sites PaCI and AsCI, the desired multigene constructs were transformed to the plant transformation binary vector plasmid pBBC3, a derivative of plasmid pGPTV-KAN to which a synthetic adaptor containing a unique PaCI and AsCI restriction site had been added.

The invention also relates to the use of the plants according to the invention or desired parts thereof in the preparation of food products or skin or hair protective products.

For example for the preparation of food products the desired parts of the plant with the altered level of flavonoids other than anthocyanin may be harvested and further processes into an edible product.

For example leaves of spinach may be harvested and heated (e.g. by blanching) optionally comminuted and subsequently frozen to produce a frozen spinach product with altered levels of flavonoids other than anthocyanins. Similarly tea leaves can be processed into leaf tea or filled into tea-bags to provide tea with enhanced levels of flavonoids other than anthocyanins.

In another embodiment seeds, e.g. pea seed may be harvested and further processed e.g. blanching and freezing into pea products. Also comminuted products may be made e.g. pea-soup. Other seeds e.g oil seeds such as sunflower seed or soy-bean may be used for the extraction of oil, preferably the conditions of oil extraction and further processing (e.g refining, esterification etc) are chosen such that the final oil still possesses the enhanced levels of flavonoids other than anthocyanins.

In another embodiment flowers such as broccoli or cauliflower may be harvested and further processed e.g. to prepare frozen vegetables or soup. Also stems such as asparagus may be harvested and further processed e.g. to product asparagus soup.

A particulare preferred embodement of the invention relates to the use of fruits especially of tomatoes with increased levels of flavonoids other than anthocyanins, particularly flavanols. These tomatoes may be harvested and eaten as such. Alternatively the tomatoes may be used in the preparation of food products. For example parts of tomato may be added to salads. Also heat-treatment may be applied, for example tomatoes may be used to prepare tomato sauces with tomato as one of the main ingredients (e.g. at levels of 10% by weight or more, for example 80% by weight or more) such as tomato paste, tomato ketchup, pizza sauce, pasta sauce, dressings etc. Also the tomatoes may be used to prepare products like tomato juice, tomato soups etc.

Surprisingly it has been found that plants of the invention not only have altered levels of flavonoids other than anthocyanins but also have other advantages.

One particular advantage is that plant of the invention, in particular tomatoes may have enhanced levels of methyl-salicylate. This, is a well-known precursor in the flavour pathway and hence leads to a better flavour of the products of the invention.

A further embodiment of the invention is that plants of the invention, especially tomatoes may lead to improved rheological properties of the products produced therefrom. For example when tomato sauces such as tomato paste, tomato ketchup, pizza sauce, pasta sauce, dressings etc are made from tomatoes of the invention this may lead to an increase of the thickness of said sauces.

The following examples are provided by way of illustration only.

DNA manipulations were performed using standard procedures well known in the art, as described, for example, in Sambrook et al, Molecular Cloning, A Laboratory Manual, Second Edition, Cold Spring Harbour Laboratory Press, 1989 (hereinafter "Sambrook").

The following literature references are mentioned in the Examples:

Becker, D. et al. (1992) Plant Mol. Biol. 20: 1195–1197.
Bonierbale, M. W. et al. (1988) Genetics 120: 1095–1103.
Bovy, A. G. et al. (1995) Acta Hortic. 405: 179–189.
Damiani, R. et al. (1993) Proc. Natl. Acad. Sci. USA 90: 8244–8248.
Hanahan, D. (1983) J. Mol. Biol. 166: 557–580.
Hertog, M. G. L. et al. (1992) J. Agric. Food Chem. 40: 1591–1598.
Hoekema, A. et al. (1985) Plant Mol. Biol. 5: 85–89.
Jackson, D. et al. (1991) Plant Cell 3: 115–125.
Jefferson, R. et al. (1987) Embo J. 6: 3901–3907.
Lloyd, A. et al. (1992) Science 258: 1773–1775.
Miller, N. J. and Rice-Evans C. A. (1997) Free Rad. Res. 26: 195–199.
Murashige, T. and Skoog, F. (1962) Physiol. Plant. 15: 73–97.
Van Engelen, F. et al. (1995) Transgenic R. 4: 288–290.
Verhoeven, H. A. et al (1997) Chromatographia 46: 63–66.

EXAMPLES

Example 1: Plant Material

All experiments can be performed using normally available processing tomato lines as the starting material. FM6203 is such a line which is comparable to the commercially available lines such as var.Napoli and var.Roma VF which are available from Simpson's Seeds (Tomato Growers Club, Surrey, England, MAFF registration number 2620).

Tomato line FM6203 was grown in a greenhouse with a 16 h photoperiod and a 21/17° C. day/night temperature.

Example 2: Bacterial Strains

The *Escherichia coli* strain used was: DH5' supE44, D(lacZYA-ArgF)U169, f80lacZDM15, hsdR17 ($r_k$-, $m_k$+), recA1, encA1, gyrA96, thi-1, relA1, deoR (Hanahan, 1983).

The *Agrobacterium* strain used was LBA4404 (Hoekema, 1985).

Transformation of *E. coli* DH5' was performed using the method of Hanahan (1983).

Transformation of *Agrobacterium* LBA4404 was performed according to Gynheung et al (1988) in Plant Molecular Biology Manual, Eds. Gelvin and Schilperoort, Kluwer Academic Publishers (Dordrecht) pPMAN-A311–19.

Example 3: Gene Constructs

3.1 Strategy to Overexpress Flavonoid Biosynthesis Genes in Tomato Fruits

The production of flavonoids in tomato fruits is increased by over-expression of the maize transcription factor-genes C1 and Lc, whose gene-products are capable of inducing the expression of the endogenous tomato flavonoid biosynthesis genes. To increase the level of flavonoids predominantly in the fruit of tomato the Lc gene is expressed under control of the fruit specific tomato E8 promoter. The C1 gene is expressed under control of the constitutive CaMV 35s promoter with double enhancer.

A cassette approach was used to clone the different components of the gene constructs, so that all promoters were cloned with the same restriction enzymes, all structural genes with the same restriction enzymes and all terminators with the same restriction enzymes. To select such restriction enzymes the nucleotide sequences for all the above mentioned genes were extracted from the Genbank nucleotide database and were searched for restriction enzymes that do not cut. These restriction sites were added to the genes either by incorporating these sites in PCR primers, or by subcloning. The genes were then cloned step by step in specially designed pUC-derived vectors that contain the selected restriction enzyme sites in their multiple cloning site.

The inserts of the final constructs were transferred to a plant transformation vector and transformed into tomato.

3.2 Construction of Cloning Vectors pUC2 and pUCM3

Figure 1:
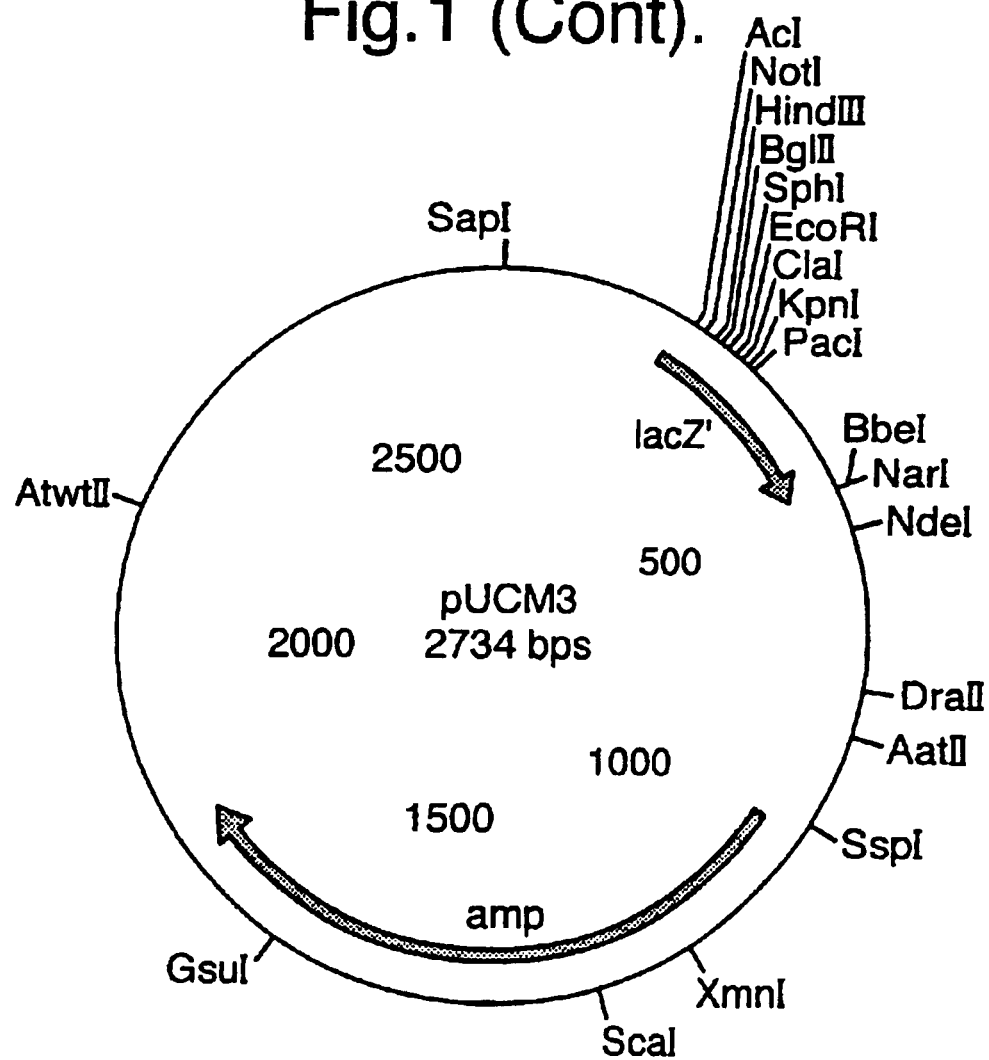
FIG. 1 shows restriction maps of plasmids pUCAP, PUCM2 and pUCM3.
Figure 3A:
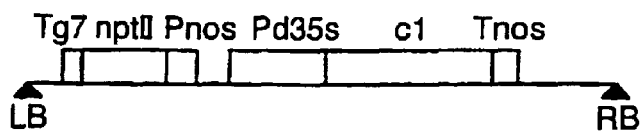
FIG. 3 shows the T-DNA region of chimeric gene constructs (a) pBBC10; (b) pBBC20; (c) pBBC30; (d) pBBC200; (e) pBBC300
Figure 3B:
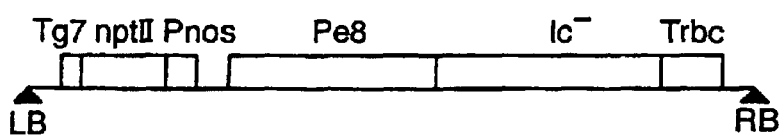
Figure 3C:
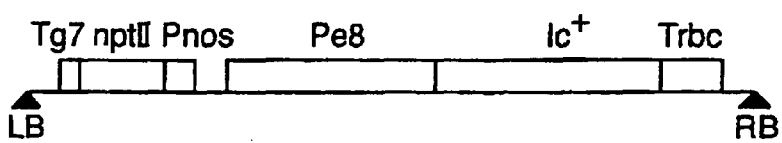
Figure 3D:
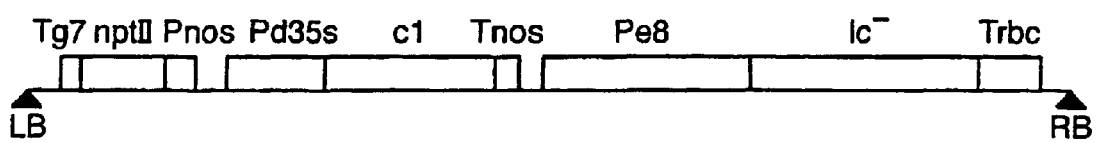
Figure 3E:
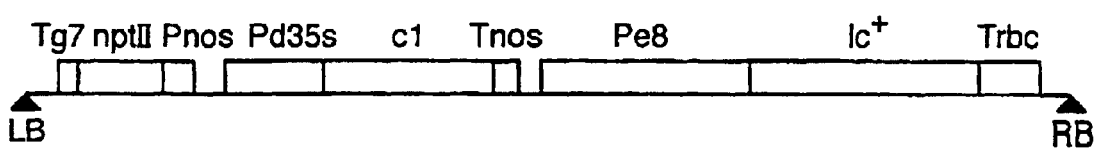

Plasmids pUCM2 and pUCM3 were derived from the cloning vector pUCAP (FIG. 1; Van Engelen et al. (1995)). The multiple cloning sites in these plasmids were constructed by insertion of synthetic adapters containing the restriction sites needed. First, each gene construct is made in pUCM2. All promoters are cloned as a KpnI/BamHI fragment, each structural gene as a BamHI/SalI fragment and each terminator as a SalI/ClaI fragment. So all gene fusions are made as a KpnI/ClaI fragment. By using the restriction sites outside of KpnI and ClaI, the gene fusions can be put behind-each other in plasmid pUCM3, which contains the restriction sites of pUCM2 in a different order. With these two gene cassettes up to four gene fusions can be cloned behind each other in one construct. With the two unique restriction sites PacI and AscI the multigene constructs can be transferred to binary vector pBBC3 (FIG. 2), a derivative of pGPTV-KAN (Becker et al. (1992)).

3.3 Construction of Lc and C1 Gene Fusions

Following the strategy described above, five binary constructs were made containing fusions of either the Lc or C1 gene alone, or both the Lc and C1 gene together. Two versions of the Lc gene were used: an Lc cDNA with its 5' untranslated leader (Lc$^+$) and an Lc cDNA lacking its 5' untranslated leader (Lc$^-$). The 5' leader contains a small open reading frame that represses Lc translation and hence the highest levels of Lc protein are obtained with the latter Lc gene (Damiani, 1993). An overview of the T-DNA region of these constructs is shown in FIG. 3. Constructs pBBC10, pBBC20 and pBBC30 are single-gene constructs. Constructs pBBC200 and pBBC300 are two-gene constructs containing both the C1 and Lc genes used to increase the amount of flavonols in tomato fruit (particularly in the flesh). In construct pBBC10 the maize C1 gene was fused with the double enhanced 35s promoter and the nos terminator. Constructs pBBC20 and pBBC30 are single-gene constructs in which both versions of the maize Lc gene (minus and plus 5' MRNA leader respectively) are fused with the tomato e8 promoter and the pea rbcS terminator. Construct pBBC200 is a two-gene construct consisting of the C1 gene fused to the d35s promoter and nos terminator, and the Lc gene (minus leader) fused to the e8 promoter and rbcS terminator. Construct pBBC300 is identical to pBBC200, except that this construct contains the Lc gene plus 5' leader. A detailed description of the construction of all plasmids used is given below.

Gene Constructs

The different components of the gene fusions and the different plasmid vectors used were obtained as follows. Plasmid vector pUCAP (Van Engelen et al. (1995)) was provided by CPRO-DLO. Binary vector pGPTV-KAN (Becker et al. 1992)) was provided by Unilever. The nos terminator (Tnos) was amplified from plasmid pBI121 (Jefferson et al. (1987)). The double enhanced CaMV 35s promoter (Pd35s) was isolated from plasmid pMOG18 (Symons et al, (1990), Biotechnology, 8, 217–221). The tomato e8 promoter (Pe8) was PCR amplified from tomato genomic DNA (variety Moneymaker) using Taq polymerase and primers E851 (5' GAATTCAAGCTTGACATC-CCTAAT 3') and E8A2 (5' CTTTTGCACTGTGAAT-GATTAGA 3'). E851 and E8A2 hybridise to the distal (5') and proximal (3') ends of the e8 promoter respectively. The resulting 2.2 kb PCR fragment was then cloned in the Eco RV site of pT7 Blue-T vector (available from Novagen). This resulted in a vector with the e8 promoter inserted in clockwise orientation (same as lac Z gene), which was called pT7E8 (FIG. 16). Constructs containing the C1 gene (pAL77), the Lc gene plus 5' leader (pAL69) and the Lc gene minus 5' leader (pAL144) were obtained from R. W. Davis (Stanford University, see also Lloyd et al (1992). The Lc genes in plasmids pAL69 and pAL144 were fused to the rbcS terminator (TrbcS) and could be used as such. All components were cloned step by step as described below.

A. Construction of Plasmids pUCM2 and pUCM3

To construct plasmid pUCM2 the multiple-cloning-site of plasmid pUCAP was modified by the insertion of two adapters. First, adapter F1F2, containing the restriction sites SalI/ClaI/SphI (Table 1), was cloned in the pUCAP plasmid digested with SalI/SphI. This resulted in plasmid pUCM1. Next, adapter F3F4, consisting of PacI/NotI/BglII/EcoRI restriction sites, was cloned in plasmid pUCM1 digested with PacI/EcoRI. This resulted in plasmid pUCM2 (FIG. 1).

To construct plasmid pUCM3, plasmid pUCAP was digested with PacI/AscI and the whole multiple-cloning-site was replaced by adapter F5F6 (Table 1). This resulted in plasmid pUCM3 (FIG. 1).

B. Construction of pBBC3

To construct plasmid pBBC3, adapter F38F39 was ligated in plasmid pGPTV-KAN digested with EcoRI/HinDIII. In this way the gusA-Tnos gene in pGPTV-KAN is replaced by a small multiple-cloning-site consisting of PacI/EcoRI/HinDIII/AscI restriction sites (FIG. 2).

C. Construetion of pBBC10

The C1 gene fusion was cloned in pUC derivative pUCM2 in three major steps.

Firstly, Tnos was amplified by PCR from pBI121 with primers F12 and AB13 (see Table 1). The resulting 250 bp product was cloned in pUCM2 as a SalI/ClaI fragment. This resulted in plasmid pFLAP1.

TABLE 1

Overview of PCR primers and adapters used

| primer(*) | sequence (5' to 3') |
|---|---|
| F1 | TCGACCATATCGATGCATG |
| F2 | CATCGATATGG |
| F3 | TAAGCGGCCGCAGATCTGG |
| F4 | AATTCCAGATCTGCGGCCGCTTAAT |
| F5 | TAAGGGTACCACCATCGATACCGAATTCTACATGCATGCATGGAGATCTCCCAAGCTTCTAAGATGCGGCCGCTAAACATGG |
| F6 | CGCGCCATGTTTAGCGGCCGCATCTTAGAAGCTTGGGAGATCTCCATGCATGCATGTAGAATTCGGTATCGATGGTGGTACCCCTTAAT |
| F7 | AATTGCACCGGTCG |
| F8 | GATCCGACCG |
| F9 | TAGCCATGGG |
| F10 | TCGACCCATGGCTAAT |
| F12 | CCCGTCGACTTTCCCCGATCGTTCAAACATTTGGC |
| AB13 | CCCATCGATGCGTCTAGTAACATAGATGAC |
| F38 | AATTGGGCGCGCCAAGCTTCCGAATTCTTAATTAAG |
| F39 | AGCTCTTAATTAAGAATTCGGAAGCTTGGCGCGCCC |
| F69 | ATGAGAGTGTGAGGAAGGAG |
| F72 | GCCATAATACTCGAACTCAG |
| F80 | TGGGCACAACAGACAATCGGCTGC |
| F81 | TGCGAATCGGGAGCGGCGATACCG |
| CYP1S | CTTCGCCGATACCACTCCCAAAAC |
| CYP2A | ACCGCAGTCAGCAATAACCACAGG |

(*)Adapters are made by combining two primers, heating to 95° C.

for 5' and anneal both primers by cooling slowly to room temperature.

Secondly, the C1 gene was cloned as a BamHI/SalI fragment upstream of Tnos in pFlap2 as follows. The C1 gene was transferred as a 2 kb EcoRI fragment from plasmid pAL77 to high-copy plasmid pBluescript SK-, resulting in a plasmid pBLC1. The C1 gene was isolated from pBLC1 as a 1.6 kb EcoRI/PacI fragment and adapters F7F8 and F9F10 (Table 1) were ligated to each end of the fragment in order to add unique BamHI and SalI restriction sites on both ends of the gene and to destroy the EcoRI and PacI sites. The resulting BamHI/SalI C1 fragment was cloned upstream of the nos terminator, resulting in plasmid pFLAP2.

Thirdly, Pd35s was cloned as a KpnI/BamHI fragment upstream of C1 in pFLAP2 as follows. To create a unique BamHI site at the 3' end of the d35s promoter plasmid pMOG18 was digested with EcoRV/BamHI, thus removing the 3' part of the d35s promoter and the gusA gene. The 3' part of the 35s promoter present in plasmid pAB80 (Bovy et al. (1995)) was ligated as a 0.2 kb EcoRV/BamHI fragment in the pMOG18 vector, resulting in plasmid pMOG18B. To create a unique KpnI site at the 5' end of the d35s promoter plasmid pMOG18B was digested with EcoRI, the ends were polished with Klenow polymerase, and subsequently digested with BamHI. The resulting 0.85 kb blunt/BamHI d35s promoter fragment was cloned into plasmid pBLC1 digested with XhoI/polished with Klenow polymerase/BamHI. This resulted in plasmid pBld35S. Finally the d35s promoter was transferred as a KpnI/BamHI fragment from pBld35s to plasmid pFLAP2. This resulted in plasmid PFLAP10 (FIG. 15).

The insert of plasmid pFLAP10 was transferred as a 2.8 kb PacI/AscI fragment to binary vector pBBC3, resulting in plasmid pBBC10 (FIGS. 3 and 17).

D. Construction of pBBC20

The construction of plasmid pBBC20 consists of three major steps: (i) cloning the Lc⁻ gene (minus leader) plus the rbcS terminator in the pUCM2 vector, (ii) cloning the fruit-specific tomato e8 promoter upstream of the Lc⁻ gene, and (iii) transfer of the Lc fusion to binary vector pBBC3. These steps will be outlined in the following paragraphs.

Firstly, the Lc⁻ gene and the rbcS terminator were isolated as a 2.8 kb BamHI/ClaI fragment from plasmid pAL144 and cloned into plasmid pUCM2 digested with the same enzymes. This resulted in plasmid pFLAP4.

Secondly, the tomato e8 promoter was cloned upstream of the Lc⁻ gene as follows. The e8 promoter was present as a 2.2 kb fragment on plasmid pT7E8. This e8 promoter fragment contained an unwanted PacI site at position 430 relative to the 5' end. To remove this PacI site, plasmid pT7E8 was digested with PacI, the ends were polished with T4 DNA polymerase, and the plasmid was self-ligated, resulting in plasmid pT7EB-Pac. The e8 promoter was subsequently amplified from this plasmid by PCR with primers F23 and F26, which contained unique KpnI and BamHI restriction sites respectively (Table 1). The PCR product was digested with these enzymes and cloned upstream of the Lc⁻ gene in plasmid pFLAP4. This resulted in plasmid pFLAP20 (FIG. 15).

Thirdly the insert of pFLAP20 was transferred as a 5.1 kb PacI/AscI fragment to binary vector pBBC3, resulting in plasmid pBBC20 (FIGS. 3 and 17).

E. Construction of pBBC30

Plasmid pBBC30 is identical to pBBC20, except for the presence of the Lc⁺ gene instead of the Lc⁻ gene. This plasmid was constructed as follows.

Firstly, the Lc⁺/TrbcS gene fusion was cloned as a EcoRI/ClaI fragment in the pEMBL-derivative pAB10. This resulted in plasmid pABLC⁺.

Secondly, the Lc⁺/TrbcS gene fusion was transferred as a BamHI/ClaI fragment from pABLC to plasmid pFLAP20, thus replacing Lc⁻/TrbcS with Lc⁺/TrbcS. This resulted in plasmid pFLAP30 (FIG. 15).

Thirdly the insert of pFLAP30 was transferred as a 5.3 kb PacI/AscI fragment to binary vector pBBC3, resulting in plasmid pBBC30 (FIGS. 3 and 17).

F. Construction of pBBC200

The single-gene constructs described above were used to construct plasmids pBBC200 and pBBC300 as follows.

Firstly, the Pd35s-C1-Tnos insert of plasmid pFLAP10 was transferred as a 2.8 kb KpnI/ClaI fragment to plasmid pUCM3, resulting in plasmid pFLAP100.

Secondly, the Pe8-Lc⁻-TrbcS insert of plasmid pFLAP20 was transferred as a 5.1 kb NotI/AscI fragment to plasmid pFLAP100, resulting in plasmid pFLAP200 (FIG. 16).

Thirdly, the insert of plasmid pFLAP200 is transferred as a 7.9 kb PacI/AscI fragment to binary vector pBBC3, resulting in plasmid pBBC200 (FIGS. 3 and 18).

G. Construction of pBBC300

To construct pBBC300, the Pe8-Lc⁺-TrbcS insert of plasmid pFLAP30 was transferred as a 5.3 kb NotI/AscI fragment to plasmid pFLAP100, resulting in plasmid pFLAP300 (FIG. 16).

The insert of plasmid pFLAP300 is transferred as a 8.1 kb PacI/AscI fragment to binary vector pBBC3, resulting in plasmid pBBC300 (FIGS. 3 and 18).

Example 4

Stable Transformation of Regulatory Gene Constructs in Tomato Line FM6203

4.1 A. *Tumefaciens* transformations

Binary plasmids pBBC10, pBBC20, pBBC30, pBBC200 and pBBC300 were introduced into *Agrobacterium* strain LBA4404 by adding 1 μg of plasmid DNA to 100 μl of competent *Agrobacterium* cells, prepared by inoculating a 50 ml culture in YEP medium (Sambrook, 1989) and growing at 28° C. until the culture reaches an $OD_{600}$ of 0.5–1.0. The cells were then pelleted, resuspended in 1 ml of $CaCl_2$ solution and dispensed into 100 μl aliquots. The DNA-*Agrobacterium* mixture was frozen in liquid nitrogen and thawed in a water bath at 37° C. After the addition of 1 ml YEP medium the bacteria were incubated at 28° C. for 4 hours with gentle shaking. Finally transformed bacteria were selected on YEP-agar plates containing 50 μg/ml kanamycin. The presence of the plasmids was tested by restriction enzyme analysis.

4.2 Tomato Transformations

Seeds from tomato line FM6203 were sterilised by a 2 h incubation in 1.5% hypochlorite, followed by three rinses of sterile water. The seeds were germinated and seedlings were grown for 8 days on a 1:1 mixture of vermacolite and MS medium (Murashige and Skoog, 1962; Duchefa) supplemented with 0.3% (w/v) sucrose, with a. photoperiod of 16 h (3000 lux) at 25° C.

Eight-day old cotyledons were cut into 25 mm² squares and preincubated for 24 h on tobacco suspension feeder layer plates at low light intensity (1000 lux). The tobacco leaf suspension culture was grown on plates containing MS medium including vitamins, supplemented with sucrose (3% w/v), agarose (6 g/l), 2,4-dichlorophenoxyacetic acid (2,4-D; 0.5 mg/l) and benzylaminopurine (BAP; 0.5 mg/l).

A single colony from the *Agrobacterium* LBA4404 cultures containing one of the binary vectors mentioned in Examples 3 and 4.1 was grown for 48 h in liquid Minimal A medium (Sambrook, 1989) supplemented with 50 μg/ml kanamycin to an $OD_{600}$ of 0.5–1.0. The bacteria were pelleted by centrifugation and resuspended in MS medium including vitamins (Duchefa) and 3% (w/v) sucrose at an $OD_{600}$ of 0.5. The cotyledon explants were incubated in the *Agrobacterium* suspension for 30', blotted dry on filter paper and co-cultivated for 48 h on tobacco feeder layer plates at 25° C. and low light intensity.

After co-cultivation, the explants were transferred to regeneration medium, consisting, of MS medium supplemented with Nitsch vitamins, sucrose (2% w/v), agargel (5 g/l), zeatin-riboside (2 mg/l), kanamycin (100 mg/l) and cefotaxime (500 mg/l). Regenerating explants were transferred to fresh medium every two weeks. Regenerating kanamycin resistant shoots were transferred to rooting medium, consisting of MS medium plus B5 vitamins, supplemented with sucrose (0.5% w/v), gelrite (2 g/l), kanamycin (50 mg/l) and cefotaxime (250 mg/l). During regeneration and rooting explants were incubated in a growth chamber at 25° C. with a 16 h photoperiod (3000 lux). After root formation, plantlets were transferred to soil and grown in the glasshouse.

Transgenic plants carrying the constructs pBBC200 and pBBC300 were numbered from 2001–2499 and 3001–3499 respectively.

Example 5: Southern Analysis of Transgenic Plants 5.0 Southern Analysis of Plants Transformed with Plasmids pBBC200 and pBBC300

The presence and the copy number of the transgenes was determined in transgenic plants by southern hybridisation. Genomic DNA was isolated from young leaves as described by Bonierbale et al. (1988). Aliquots of 5 μg genomic DNA were digested for 16 h with BglII and separated on a 0.7% TAE agarose gel. The DNA was then denatured in 0.4 M NaOH for 30' and transferred to a Hybond N+ membrane in 0.4M NaOH.

The blots were probed with a 700 bp $^{32}$P radiolabeled nptII-specific PCR fragment, amplified from plasmid pBBC3 with primers F80 and F81 (Table 1), under stringent conditions (65° C.). Prehybridisation was carried out for 2 h at 65° C. in a mix of 6.6×SSC, 10×Denhardt's solution, 0.1% SDS, and 0.1 mg/ml denatured herring sperm DNA. Hybridisation was performed by adding denatured probe DNA to the prehybridisation medium and continuing the incubation at 65° C. for 16 h. The hybridised blots were washed three times for 30 minutes at 65° C. in 0.2×SSC, 0.1% SDS and autoradiographed using a bio-imager (Fuji).

BglII cuts in the T-DNA immediately upstream of the nptII gene, 1.7 kb from the left border (LB). Hybridising nptII-specific fragments are flanked on one end by this internal BglII site and on the other end by a genomic BglII site in the region flanking the LB of the T-DNA. This will give rise to hybridising bands of different length, dependent on the place of integration, and can be used to determine the number of T-DNA insertions in each transgenic plant.

The result of the southern analysis is shown in FIG. 4. Plant number 3028 (lane 3) is a non-transgenic escape from the tissue culturing. All other plants are transgenic and hybridise with the nptII probe. The copy number in the transgenic plants varies from 1 to 4.

5.1 Southern Analysis of Plants Transformed with Plasmid pBBC10

The copy number and the quality of the T-DNA insertion in transgenic plants obtained after transformation with plasmid pBBC10 (100 numbers) was determined by southern hybridisation. Aliquots of 5 μg genomic DNA were digested for 16 h with both EcoRI and NcoI, separated on a 0.7% TAE agarose gel and transferred to a Hybond N+ membrane as described in 5.0.

The blot was probed with a 900 bp $^{32}$P radiolabeled C1-specific restriction fragment, obtained after digestion of plasmid PFLAP10 with NcoI/PstI. Hybridisation and washing conditions were as described in section 5.0.

EcoRI cuts in the T-DNA immediately upstream of the P35s-c1-Tnos gene-fusion, 2.8 kb from the right border (RB). Hybridising C1-specific fragments are flanked on one end by this internal EcoRI site and on the other end by a genomic EcoRI site in the region flanking the RB of the T-DNA. This will give rise to hybridising bands of different length, dependent on the place of integration, and can be used to determine the number of T-DNA insertions in each transgenic plant.

NcoI cuts twice in the T-DNA region of plasmid pBBC10, at position +92 relative to the c1 translation startsite and in the linker between the C1 gene and the nos terminator. Digestion of chromosomal DNA with NcoI therefore will give rise to a hybridising band of 1.5 kb.

The result of the southern analysis is shown in FIG. 5. Plant number 5002 is a transgenic plant containing a Pe8- gusA-Tnos insert and is used as a negative control. All other plants are transgenic and hybridise with the c1 probe. The copy number in these transgenic plants varies from 1 to 4 (panel A). After digestion with NcoI, all transgenic plants, except 5002, give a band of 1.5 kb, which runs at the same position as the NcoI-digested pBBC10 plasmid (panel B). This indicates that all tested pBBC10 transformants contain at least one intact copy of the C1 gene.

5.2 Southern Analysis of Plants Transformed With Plasmids pBBC20 and pBBC30

The copy number and the quality of the T-DNA insertion in transgenic plants obtained after transformation with plasmid pBBC20 (200 numbers) and pBBC30 (300 numbers) was determined by southern hybridisation. Aliquots of 5 pg genomic DNA were digested for 16 h with BglII/ClaI, separated on a 0.7% TAE agarose gel and transferred to a Hybond N+ membrane as described in section 5.0.

To determine the copy number, the blot was probed with a 700 bp $^{32}$P radiolabeled nptI-specific fragment (see section 5.0). To determine the quality of the T-DNA insertion the nptII-probe was stripped from the blot according to the manufacturer's protocol (Amersham) and reprobed with a 0.7 kb Lc-specific restriction fragment, obtained after digestion of plasmid pFLAP30 with PstI/NcoI. Hybridisation and washing conditions were as described in section 5.0.

BglII and ClaI in total cut four times in the T-DNA region of pBBC20 and pBBC30 transformants. Relative to the left border, BglII is the first restriction site within the T-DNA. It cuts immediately upstream of the nptII gene, 1.7 kb from the left border (LB). Hybridising nptII-specific fragments are flanked on one end by this internal BglII site and on the other end by a genomic BglII site in the region flanking the LB of the T-DNA. This will give rise to hybridising bands of different length, dependent on the place of integration, and can be used to determine the number of T-DNA insertions in each transgenic plant. BglII cuts once in the Pe8-lc-Trbc gene-fusion of plasmids pBBC20 and pBBC30, at position +202 relative to the lc translation startsite. ClaI cuts immediately downstream of, the rbcs terminator. Digestion of chromosomal DNA with BglII/ClaI therefore will give rise to a hybridising band of 2.6 kb with the lc-specific probe.

The results of the southern analyses are shown in FIG. 6 (nptII probe) and FIG. 7 (lc probe). Plant number 004 is a non-transgenic control plant, which does not hybridise with any of the probes used. Plant-numbers 5002, 104, 109 and 117 only hybridise with the nptII probe, and not with the lc probe. All other plants (200 and 300 numbers) are transgenic and hybridise with both the nptli and the lc probes. The copy number in these plants varies from 1 to 7 (FIG. 6). After hybridisation with the lc probe, all 200 and 300 numbered plants give a band of 1.5 kb, which runs at the same position as the BglII/ClaI-digested pBBC20 and pBBC30 plasmids (FIG. 7). This indicates that all tested pBBC20 and pBBC30 transformants contain at least one intact copy of the Lc gene.

Example 6

Measurement of Flavonoids in Tomato Fruits 6.1 Growth and Harvest of Tomato Fruits Tomato plants were grown in 10 l pots in a greenhouse at standard growth conditions. Fruits were harvested at fully red, ripe stage; and in the case of development studies (FIG. 14) also at earlier stages of development. For discrimination between flavonoids in peel and in flesh tissue, the outer layer of about 2 mm thick (i.e.cuticula, epidermal layer plus some sub-epidermal tissue) was separated from the fruit using a scalpel; the remainder of the fruit was classified as flesh tissue. After separation, tissues were quickly cut into pieces, frozen in liquid nitrogen and stored at −80° C. until use. For anal ysis of flavonoid levels in whole fruits, red fruits were cut into quarters, per fruit a quarter was taken, cut into pieces and quickly frozen.

6.2 Extraction of Flavonoids From Tomato Tissues

Flavonoids were determined as aglycons or as their glycosides by preparing hydrolysed and non-hydrolysed extracts, respectively.

Preparation of hydrolysed extracts was performed according to Hertog et al. (1992) as follows: Frozen tissues were grounded into a fine powder using either a pestle and mortar or a coffee grinder. Peel and flesh tissues were lyophilized for 24 h before flavonoid extraction. Forty mg of this freeze-dried material was weighed and transferred to a 10 ml Pyrex glass tube. To each tube 1.6 ml of 62.5% methanol (HPLC grade) in distilled water and 0.4 ml of 6M HCl were added. The tubes were closed with screw caps containing a teflon inlay and incubated for 60 min at 90° C. in a waterbath. After hydrolysis, the tubes were cooled on ice, the extracts were diluted with 2 ml of 100% methanol and sonicated for 5 min. For determination of aglycon levels in whole tomatoes, 1.2 g of grounded frozen tissue (not lyophilized) was weighed and hydrolysed with 2 ml of 100% methanol and 0.8 ml of 6M HCl, as described above. After hydrolysis, these whole tomato extracts were diluted with 4 ml of 100% methanol, and sonicated for 5 min.

Using flavonoid standards (obtained from Apin Chemicals Ltd, Abingdon, UK) it was established that during the hydrolysis step, aglycons were released from their respective glycosides for 100%, while narichalcone (=naringenin-chalcone) was chemically converted into naringenin for more than 95%. Recoveries of quercetin, kaempferol and naringenin standards added to peel or flesh extracts just before hydrolysis were more than 90%.

For determination of flavonoid-glycosides and naringenin-chalcone, 40 mg of freeze-dried tomato tissue was added to 4 ml of 75% aqueous methanol acidified with HCl to pH2. Extraction took place at room temperature (20–25° C.) by continuously mixing on a roller band for 2 hours.

6.3 HPLC Conditions for Flavonoid Analysis

After sonication, about 1 ml of each extract was taken using a disposable syringe and filtered through a 0.2 μm PTFE disposable filter (Inacom Instruments BV, The Netherlands) before injection into the HPLC system.

The HPLC system consisted of a Waters 600E Multisolvent Delivery System (Waters Chromatography), a Promis autoinjector (Separations Analytical Instruments BV) with a fixed 10 μl loop, and a Nova-Pak $C_{18}$ (3.9×150 mm, particle size 4 μm) analytical column (Waters Chromatography) protected by a Guard-Pak Nova-Pak C18 insert. Both columns were placed in a LKB 2155 HPLC column oven (Pharmacia Biotech) set at 30° C. A photodiode array detector (Waters 996) was used to record spectra of compounds eluting from the column on-line. The detector was set at recording absorbance spectra from 240 to 600 nm with a resolution of 4.8 nm,. at a time interval of 1 second. Millennium 2010 Chromatography Manager (Waters Chromatography BV) was used to control the solvent delivery system and the photodiode array detector.

HPLC separation of flavonoids present in hydrolysed extracts (flavonol aglycons and naringenin) was carried out under isocratic conditions of 25% acetonitril (for HPLC far UV) in 0.1% trifluoroacetic acid (TFA) at a flow rate of 0.9 ml/min. HPLC separation of flavonoids in non-hydrolysed extracts (flavonoid-glycosides and naringenin-chalcone) was performed using a gradient of acetonitril in 0.1% TFA, at a flow rate of 1.0 ml/min: 5–25% linear in 30 min, then 25–30% in 5 min and 30–50% in 2 min followed by a 3 min washing with 50% acetonitril in 0.1% TFA. After washing, the eluent composition was brought to the initial condition in 2 min, and the column was equilibrated for 6 min before next injection. Table 2 summarizes the retention times, obtained with the two different HPLC separation methods, of some flavonoid standards.

TABLE 2

Typical retention times of some flavonoid standards.

| flavonoid standard | detection wavelength (nm) | retention time (minutes) isocratic run | retention time (minutes) gradient run |
|---|---|---|---|
| rutin | 360 | — | 19.2 |
| quercetin-3-glucoside | 360 | — | 19.7 |
| kaempferol-3-rutinoside | 360 | — | 21.9 |
| myricitin | 370 | 3.0 | 23.0 |
| quercetin | 370 | 5.1 | 29.5 |
| naringenin | 280 | 8.3 | 33.5 |
| narichalcone | 360 | — | 34.8 |
| kaempferol | 370 | 9.8 | 35.5 |

Note: anthocyanins peaks would normally be visible in spectra at 520 or 280 nm. In the experiments however these peaks are not visible (see e.g. FIG. 25) meaning that no detectable levels of anthocyanins were formed in the tissues tested.

HPLC data were analyzed using the software of the Millennium 2010 Chromatography Manager. Absorbance spectra (corrected for baseline spectrum) and retention times of eluting peaks (with peak purity better than purity threshold value) were compared with those of commercially available flavonoid standards. Dose-response curves of quercetin, naringenin and kaempferol (0 to 20 µg/ml) were established to quantify these compounds in the hydrolysed tomato extracts. Quercetin and kaempferol aglycons were detected and calculated from their absorbance at 370 nm and naringenin at 280 nm. Flavonol-glycosides as well as naringenin-chalcone were detected at 360 nm (see also Table 2). Flavonoid levels in tomatoes were calculated either on a dry weight basis (for peel and flesh tissues) or on a fresh weight basis (for whole tomatoes). With the HPLC system and software used, the lowest detection limit for flavonoids in tomato extracts was about 0.1 µg/ml, corresponding with 10 mg/kg dry weight and 1 mg/kg fresh weight. Variation between replicate injections was less than 5%.

Example 7

Figure 8A:
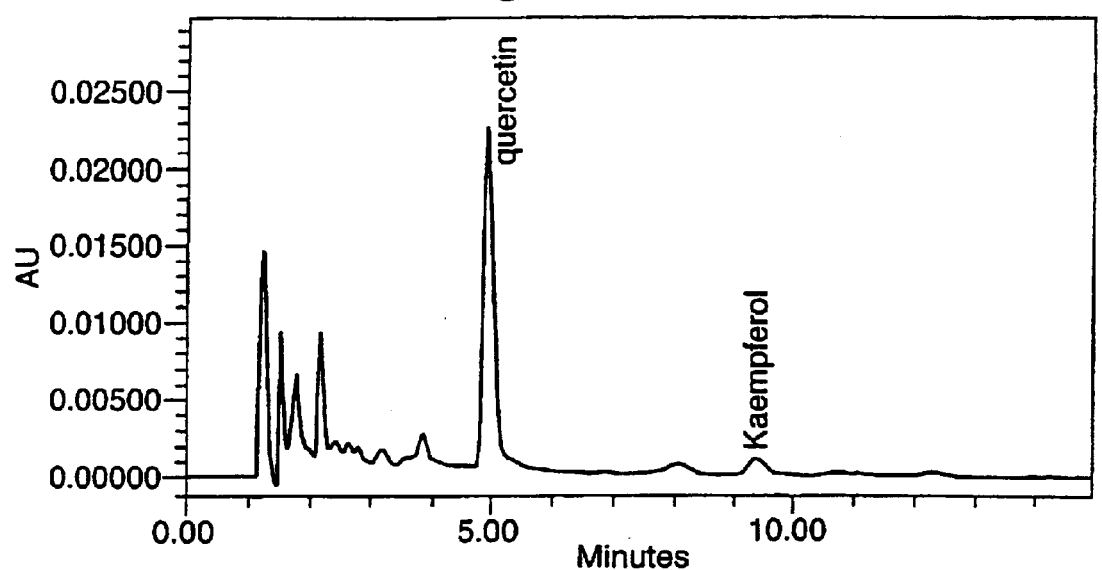
Figure 8B:
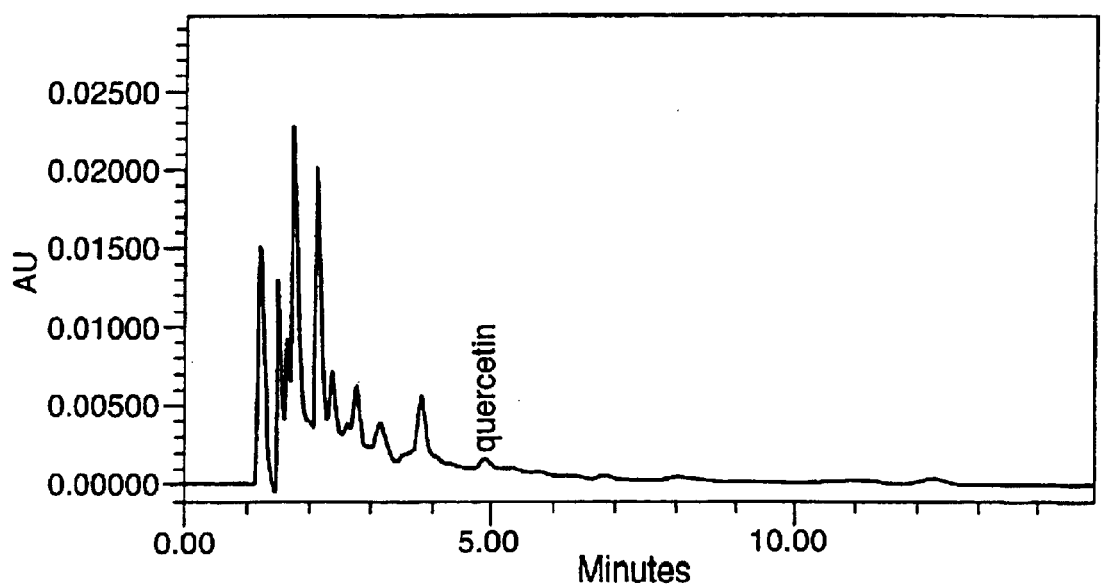

Characterisation of the Flavonoid Content in Transgenic Tomato Fruit 7.1 Flavonoids in Peel and Flesh of Control Tomatoes The HPLC data of hydrolysed extracts of red fruit of variety FM6203 are shown in FIG. 8. FIG. 8a shows that both quercetin and kaempferol were present in peel tissue. In contrast, FIG. 8b illustrates that hydrolysed extracts of the flesh tissue from this fruit contained only traces of quercetin with no detectable levels of kaempferol. Chromatograms obtained at 280 nm (not shown) of the same extracts revealed a large peak of naringenin in the peel, but not in the flesh.

FIG. 9 shows the HPLC spectrum of non-hydrolysed extracts of this fruit. It can be seen that only a small peak corresponding to rutin was present in the flesh (FIG. 9B). In contrast, at least 5 different flavonol-glycosides as well as narichalcone were detected in the peel (FIG. 9A). NMR-studies proved that the peak at RT=19.2 min was rutin while the peak at 17.6 min was a quercetin-3-trisaccharide: rutin with apiose linked to the glucose of the rutinoside. The retention time and absorbance spectrum of the minor peak at 19.7 min corresponded with those of quercetin-3-glucoside, while those of the peak at 21.9 min corresponded with kaempferol-3-rutinoside. The small peak at 25.6 min had an absorbance spectrum comparable to kaempferol-3-rutinoside, but its higher RT value indicates a yet unknown kaempferol-glycoside. The large peak at 34.8 min was narichalcone. Aglycons of quercetin and kaempferol, as well as naringenin (all present in hydrolysed peel extracts) were not detectable in any of the non-hydrolysed extracts.

By comparing the flavonoid species in hydrolysed extracts with those in non-hydrolysed extracts of the same tissue it can be concluded that the presence of quercetin and kaempferol aglycons in the hydrolysed extracts resulted from hydrolysis of their respective glycosides; the presence of naringenin in hydrolysed peel extracts resulted from isomerization of narichalcone during the hydrolysis step (cf. Example 6.2).

These HPLC-data of flavonoids indicate that the flavonoid biosynthetic pathway is active in the peel but not, or to a very limited level only, in the flesh of the tomato fruit. This conclusion was confirmed by mRNA analyses of peel and flesh tissues using probes for chs, chi and fls.

7.2 Flavonoida in Fruits of Transformed Tamato Plants

To determine whether the pBBC200 and pBBC300 constructs were able to induce the flavonoid biosynthetic pathway in tomato plants, transformants as well as control plants were analysed for the presence of flavonoids in the flesh of their fruits, a tissue that normally contains only traces of flavonoids (see 7.1). This screening was performed by HPLC using hydrolysed extracts. 17 plants that were successfully transformed with either the pBBC200 or the pBBC300 construct (i.e. nptII-positive plants) were analysed together with 10 untransformed control plants (escapes, i.e. plants that appeared nptII-negative after the transformation and kanamycin selection steps). All untransformed control plants tested contained only a small amount of quercetin in hydrolysed extracts of the tomato flesh and none had detectable levels of kaempferol or naringenin, as was the case with the original FM6203 plants. Out of the 17 transformants tested, 11 plants (65%) appeared to accumulate flavonoids, specifically of the kaempferol and naringenin-type,. at detectable levels in their tomato flesh. FIG. 10 shows an example of chromatograms (recorded at 370 nm) obtained with an untransformed control plant and plant number 3031 containing the pBBC300 gene construct. While the hydrolysed flesh extracts of the untransformed tomato contained only a small peak of quercetin (cf. Example 7.1, FIG. 8), the hydrolysed flesh extract of the transformed tomato contained a clear peak of kaempferol (FIG. 10), as well as of naringenin (detected at 280 nm, not shown). FIG. 11 summarises the levels (on a dry weight basis) of kaempferol, quercetin and naringenin, based on hydrolysed extracts, in the flesh of red fruits from some control plants and some plants transformed with either the pBBC200 or the pBBC300 gene construct. The main flavonoid present in the hydrolysed extracts of flesh of transformed plants was kaempferol, followed by naringenin; an exception was plant number 3035, whose hydrolysed flesh extract contained more naringenin than kaempferol. Quercetin was not or only slightly increased in these transformants. Also in hydrolysed extracts of peel tissue of the pBBC200 and pBBC300 transformed tomato plants an increase in kaempferol content was observed.

FIGS. 12 and 29 show the levels (on a fresh weight basis) of flavonoids in whole red fruits of control and transformed tomato plants. The level of total flavonols (quercetin plus kaempferol) in fruits of control plants (first bar) was 5.2±4.3 mg/kg fresh weight (mean± standard deviation, n=10), with values ranging between 1.3 and 12.0 depending on growing season. Quercetin was always the main flavonol in the fruits of control plants. Compared to the mean level in control plants, 11 out of 13 pBBC200-transformed plants (i.e. 85%) and 11 out of 17 pBBC300-transformed plants (65%) had significantly increased levels, up to 75 mg/kg i.e. 15 fold increase, of total flavonols in their fruits. The highest levels of kaempferol in transformants were about 75 mg/kg: a 75 fold increase compared to control levels. In contrast to kaempferol, quercetin was increased in only a few plants and to a much lower extent: up to 3 times the level in controls. The level of naringenin in control fruits, derived only from narichalcone present in the peel, was 24±14 mg/kg fresh weight (mean± standard deviation, n=10). The naringenin level in whole fruits of transformants, derived from both narichalcone and naringenin-glycosides (cf. FIGS. 27 and 25) was significantly increased in a few plants: up to 2.5 fold the level of control fruits.

Using non-hydrolysed extracts, the form in which the flavonoids accumulated in the tomato fruits of transformed plants was studied. By comparing HPLC chromatograms of non-hydrolysed extracts from whole red fruits of control and transformed tomatoes, recorded at 360 nm (FIG. 26), it appeared that the level of naringenin chalcone (peak at RT=35.9 min was decreased in transformed tomatoes. However, at least 6 other flavonoids detectable at 360 nm were increased in the transformed tomato fruits: peaks at RT=13.9, 14.3, 16.1, 22.8, 23.4 and 26.0 min,. Apart from these 6 compounds, the HPLC chromatograms recorded at 280 nm (FIG. 27) indicated an increase of at least another 5 flavonoid compounds in the transformed tomatoes: peaks at RT=11.2, 15.2, 21.2, 23.1 and 28.5 min. Other peaks that were increased in the chromatograms of transformed fruits (e.g. in FIG. 14: peaks at RT=5.1 and 11.9 min) appeared to be impure peaks resulting of co-elution of yet unknown compounds. Based on the chromatographic behaviour and absorbance spectra of pure peaks that were increased in the transgenic fruits (FIG. 25), it is concluded that the compound eluting at RT=22.8 min is kaempferol-3-O-rutinoside and that at 23.1 min is naringenin-7-O-rhamnoglucoside (=naringin). The absorbance spectra of the compounds eluting at 13.9, 14.3, 16.1, 23.4 and 26.0 min all match very well with kaempferol-3-rutinoside, but their different RT values indicate that they are different kaempferol-glycosides. Likewise, the compounds at RT=11.2, 15.2, 21.2 and 28.5 min have absorbance spectra similar to naringin, but their different RT values indicate that they are different naringenin-glycosides.

The patterns of chromatograms (recorded at 360 nm) obtained with non-hydrolysed tomato extracts were very similar within and between pBBC200 and pBBC300 transformants. This result indicates that all transformants accumulated the same flavonoid species at about similar ratios; transformants only differed in their level of accumulation.

FIG. 13 shows an example of chromatograms, recorded at 360 nm, of non-hydrolyzed extracts prepared from only the flesh tissue of the tomato fruits (peel removed). While only rutin was detectable in the flesh of control fruits, rutin as well as the kaempferol-glycosides described above (FIG. 26) were detectable in the flesh of transgenic fruits. RPLC analyses of the same flesh extracts at 280 nm (not shown) revealed that, apart from these kaempferol-glycosides, the naringenin-glycosides described above (FIG. 27) were exclusively produced in transgenic fruits. These results indicate that the flavonoids biosynthetic pathway in transgenic plants is not restricted to the peel, as it is in untransformed plants, but also active in the flesh of the fruits.

Out of the 11 flavonoid species that were increased in the whole fruits of transgenic plants (FIG. 26) only kaempferol-3-rutinoside was also found in the fruits of FM6203 control plants, though only in the peel. Thus, tomato plants transformed with pBBC200 or, pBBC300 exclusively produced (at least) 6 different kaempferol-glycosides and 5 naringenin-glycosides in the flesh of their fruits. Moreover, except for kaempferol-3-rutinoside, the flavonoid species induced by pBBC200 or pBBC300 are new products in the fruits of variety FM6203.

The accumulation of flavonoids in fruits of transformed plants was dependent upon ripening stage. FIG. 14 shows that the kaempferol peak was not detectable in hydrolysed extracts of flesh from full-grown tomato fruits at green stage, small at turning stage and highest at red stage. A similar ripening-dependent increase was observed for naringenin (chromatograms recorded at 280 nm; not shown). This timing of the flavonoid biosynthesis correlated with the pattern of activation of the e8 promotor, which is present in both the pBBC200 and the pBBC300 gene construct.

In some plants transformed with pBBC200 or pBBC300 a slight purple pigmentation due to anthocyanin accumulation was observed in the fruits, but only at green and breaker stage. Binocular analyses of cross sections of these purple-coloured fruits revealed that the anthocyanin accumulation was restricted to the peel tissue of the fruits. However, anthocyanins could not be detected, neither by eye nor by HPLC analyses of hydrolysed and non-hydrolysed extracts at 520 nm, in red fruits. In contrast to this pattern of anthocyanin production, the production of kaempferol- and naringenin-glycosides in the same transgenic fruits was not restricted to the fruit peel and increased during fruit ripening (see above). Therefore, the induced biosynthesis of flavonoids in tomato fruits, as claimed in the present invention, is not related to the production of anthocyanins.

7.3 Transformation with Both Lc and C1 is Essential for Increasing Flavonoid Levels in Tomato Fruits To check whether C1 or Lc alone might as well induce the flavonoid biosynthesis in tomato fruits, variety FM6203 was also transformed with the plasmids pBBC10, pBBC20 and pBBC30 containing the single regulatory gene constructs d35s-c1, e8-lc minus leader sequence and e8-lc plus leader sequence, respectively. Hydrolysed extracts were prepared from whole red fruits and analysed by HPLC as described in Example 6. FIG. 28 shows that fruits of plants transformed with only C1 (plants numbered 101 onwards) or only Lc (plants numbered 201 and 301 onwards for plants without and with leader sequence, respectively), had levels of total flavonols (quercetin plus kaempferol) ranging from 1.2 to 8 mg/kg fresh weight. i.e. within the range of control fruits (1.8 to 8.8 mg/kg fresh weight). These data indicate that transformation of tomato plants with either C1 or Lc (with or without leader sequence) did not result in increased flavonol levels in their fruits. In contrast, fruits of plants containing both regulatory genes after transformation with pBBC200 or pBBC300 (numbered 2000 and 3000 onwards, respectively) had significantly increased levels of flavonols in their fruits, as compared to both the control plants and the plants transformed with the single gene constructs. This increase in flavonols was mainly due to the accumulation of kaempferol (FIG. 29). Evidently, the presence of two transcription factor genes such as both C1 and Lc is essential for the increased production of flavonoids in tomato fruits.

Similarly the level of flavonols can be measured in the leaves of the transformed tomatoes. It was found that the the levels of flavonols in the leaves was increased up to six-fold as compared to the control and mostly were at a level lower than the flavonol level in the flesh of the fruit. In none of the cases lethal dosis of flavonols were encountered, this may be explained by the fact that a fruit-specific promoter was used, which although it apparently does not fully prevent formation of flavonols in leaves it limits the levels to non-lethal dosis.

Example 8

Analysis of Transgene Expression in Transgenic Plants

The expression of the introduced C1 and Lc genes in the obtained transgenic tomato plants was analysed by real-time quantitative RT-PCR, using the fluorogenic 5' nuclease assay performed with the Taqman PCR reagent kit on the ABI PRISM 7700 sequence detection system (Perkin-Elmer/ABI). The principle of this procedure is as follows: cDNA is made from total RNA, extracted from the source of interest, by reverse transcription. The expression of a target gene is monitored in a PCR reaction to which a fluorogenic probe, consisting of an oligonucleotide with both a reporter and a quencher dye attached, is added, that anneals specifically between the forward and reverse primers. When the probe is cleaved by the 5' nuclease activity of the DNA polymerase, the reporter dye is separated from the quencher dye and a sequence-specific signal is generated. With each cycle, additional reporter dye molecules are cleaved from their respective probes, and the fluorescence intensity is monitored during the PCR reaction. The PCR cycle at which the fluorescence reaches a certain threshold value is a measure for the starting copy number of the target RNA. This can be quantified by running a standard range with known amounts of the target gene.

The following plants were selected for Taqman analysis: plants transformed with plasmid pBBC10 (P35s-c1-Tnos), numbers 104, 109 and 117 plants transformed with plasmid pBBC20 (Pe8-lc$^-$-Trbc), numbers 201, 204 and 209 plants transformed with pBBC30 (Pe8-lc$^+$-Trbc), numbers 302 and 305; plants transformed with pBBC300 (P35s-c1-Tnos//Pe8-lc$^+$-Trbc), number 3031; and plants transformed with plasmid pBBC250 (Pe8-c1-Tnos//Pe8-lc$^-$-Trbc), numbers 2509, 2511 and 2519. In plasmid pBBC250 both the C1 and the Lc gene are expressed under control of the fruit-specific tomato e8 promoter. Plasmid pBBC250 is represented in FIG. 20 and can be prepared analogously to plasmids pBBC200 and pBBC300, transformants with plasmid pBBC250 are numbered 2500–2999.

Total RNA was isolated from red fruits of transgenic tomato plants. First strand cDNA was synthesised from 350 ng of total RNA by reverse transcription. Aliquots of 100 ng CDNA were used in three Taqman PCR reactions with a c1, lc and a cyp probe respectively. The tomato cyclophyllin gene (cyp) is constitutively expressed in tomato fruits, as observed by northern analysis, and can therefore be used as internal control. Known amounts of plasmid pFLAP300 and a 0.4 kb cyclophyllin PCR fragment, obtained after RT-PCR of tomato fruit RNA with primers CYP1S and CYP2A (Table 1), were used as standards. The sequence of the taqman primers and probes used is listed in Table 4.

For all three primer-probe combinations, the number of specific mRNA molecules present in each sample was determined and expressed relative to the amount of cyp mRNA. The absolute amount of cyp mRNA varied less than 2.5-fold between the different transgenic plants, indicating that this gene can indeed function as an internal control. As shown in FIG. 21, control plant 004 neither gave a signal with the c1 probe, nor with the lc probe. In contrast, all tested transgenic plants showed a clear expression of the introduced transgenes: the C1 single-gene plants (104, 109 and 117) showed only C1 gene expression, the Lc single-gene plants (201, 204, 209, 302 and 305) only showed Lc gene expression and all tested C1/Lc double-gene plants (2509, 2511, 2519 and 3031) showed expression of both C1 and Lc. Although the expression level of the C1 and Lc genes in some single-gene transgenic plants is higher than the levels found in some double-gene plants, yet there is no detectable increase in the level of kaempferol (FIG. 21). This indicates that expression of both C1 and Lc together is required to up-regulate the flavonoids pathway in tomato fruits, leading to an increased production of the flavonol kaempferol.

TABLE 4

Overview of Taqman primers and probes used

| Primer/probe(*) | gene | sequence (5' to 3') |
|---|---|---|
| C1F | C2 | GCCCTGGCGTCGTTTCT |
| C1R | C1 | TGGACATCTATACGTGTACTTGTTGTCTAC |
| C1T(*) | C1 | CTCCGCTGTCAGACGGCCGG |
| LCF | Lc | CGGGAGCAGCACAGGAAAT |
| LCR | Lc | GTCGCTTTCGCTCCGACAT |
| LCT(*) | Lc | TGGCACTGGCACCAAGAACCACG |
| CYPF | cyp | GAGTGGCTCAACGGAAAGCA |
| CYPR | cyp | CCAACAGCCTCTGCCTTCTTA |
| CYPT(*) | cyp | ACATCCATGCCTTCAACAACTTGTCCAA |

(*)Fluorescently labeled Taqman probes.

Example 9

Tomato Fruits with Increased Flavanoid Levels by Transformation with lc and c1 Exibit an Increased Antioxidant Activity Because the postulated beneficial effects of flavonoids in the human diet is, at least partly, ascribed to their antioxidant characteristics, it was tested whether tomato plants with increased levels of flavonoids in their fruits also have increased antioxidant activities.

From 3 control and 3 independent transformants [numbers 3031, 3059 and 3060 as described above], 0.6 g FW of whole fruits (grinded material from 3 red fruits pooled per plant) was weighed, extracted in 2 ml of 70% methanol by sonication for 30 min, and filtered (0.2 μm). Antioxidant activity was tested from the ability of extracts to react with the coloured radical cation of ABTS (2,2'-azinobis[3-ethylbenzothiazoline-6-sulphonic acid]), essentially as described in Miller and Rice-Evans (1997). The ABTS-radical stock solution, generated with potassium persulphate, was diluted in 5 mM potassium phosphate (pH 7.4) containing 150 mM NaCl just before use, obtaining a working solution with an absorbance value of 1.240 measured at 734 nm. The antioxidant activity of tomato extracts was assayed by adding 10 pl of extract to 990 μl of the ABTS-radical working solution, mixing for 30 sec and reading the absorbance at 734 nm exactly 1 min after the addition of extract. A calibration curve of trolox (0–20 nmol) was prepared to calculate the trolox-equivalent antioxidant capacity values (TEAC values) of the tomato extracts. Variation between replicates was always less than 7%.

The TEAC value of control tomato extracts was 2513±409 µmol/kg FW (mean ± standard deviation of 3 plants). Compared to this control value, the TEAC values of the transgenic plants were increased by 20% in 3031, 40% in 3059 and 64% in 3060. FIG. 22 shows that the TEAC values of the fruits were closely related to the levels of total flavonoids in these fruits, in both control and transgenic plants. This result suggests that the increased antioxidant activity observed in the fruits of lc/cl-transformed plants resulted from the increased flavonoid biosynthesis.

Example 10

Properties of Tomato Pastes Prepared from Transformed Tomatoes of the Invention

This example demonstrates that overexpression of transcription factors in tomato can improve commercially-important properties such as paste consistency, in particular by leading to thicker pastes at the same fruit usage level.

Data from five independent paste preparations are included in this example. Pastes 1 and 2 are from T1 generation plants (i.e. a population derived from seed of the selfed primary transgenic plant 2059). Pastes 3, 4 and 5 are derived from T2 homozygous plants.

10.1 Plant Material
10.1 Growing

Seed from the selfed single-insert 2059 primary transgenic tomato plants were sown in soil flats in a glasshouse under light conditions as in Example 1. Seedlings which had retained the pBBC300 transgene were selected by PCR, using the transgene specific primer pair F69/F72 (table 1). PCR positive transgenic plants were designated 2059±. PCR negative control plants having lost the pBBC300 transgene through segregation were designated 2059−. FM6203 (the parent line) was also planted as a control.

After selection by PCR, 16–20 day old seedlings were transferred to an automatic hydroponics feeding and watering system.

Seeds from homozygous selfed T1 plants were planted in soil flats in a glasshouse. 16–20 day old seedlings were transferred to an automatic hydroponics feeding and watering system.

Fruits were harvested between 18–21 days post breaker (breaker represents the stage were the first flush of orange colour appears on the developing fruit). Fruits were used for paste production within 2–4 hours of harvest.

10.2 Preparation of Tomato Paste

450–850 g of fruit was diced (15 mm) and microwaved in a Pyrex bowl for 4, 2 and 1 minutes (full power) stirring between each period of heating. The pulp was chilled to room temperature on melting ice and $H_2O$ added to bring the cooked tomato pulp upto the original wet weight. Chilled juice was sieved through meshes of 1400 and 710 µm whereby losses (seed+skin) of around 10–14% were typically incurred.

A weighed amount of hot break juice was centrifuged at 5,000 RPM for 5 min, the serum decanted and the serum and pellet weights determined (serum/pellet ratio). The serum pellet ratio is a measure of particle occupancy—the thicker the paste the lower the serum/pellet ratio. Paste prepared using tomatoes from the 2059+ line possessed consistently lower serum/pellet ratios than those prepared from either 2059− or parent FM6203 lines (FIG. 23).

Pastes were reconstituted by blending back a portion of the serum (typically to 75% of juice weight) to the pellet, allowing a minimum of 1 hour at room temperature for the particles to re-swell.

Bostwick represents the Industry standard way for measuring paste viscosity. Approx. 100 g of this 75% paste (prepared as above) was placed in the chamber of the levelled Bostwick, the shutter opened and the distance (in cm) over which the paste flows in 30 sec. was recorded. Pastes with a low Bostwick value have a high viscosity and vice versa.

Pastes prepared with tomatoes derived from the 2059+ line possessed consistently lower Bostwick values than those prepared from the 2059− or parent FM6203 line (FIG. 24).

These results show that tomato lines of the invention provide advantageous properties to tomato products, for example they can provide increase thickness of products such as tomato pastes.

Example 11

Transformation of Tomato Plants with Lc and C1 Increases the Production of Methylsalicylate in the Fruits The effects of the regulatory genes lc and c1 on the production of volatiles produced by the tomato fruits were tested, using solid phase microextraction (SPME) and gas chromatography coupled to mass spectrometry (GC-MS).

In a 4 ml glass vial, 0.5 g of frozen material (fresh weight basis) of grinded whole red fruits was weighed. After thawing, the fruit material was incubated at room temperature with gently stirring for 5 min, to allow enzymatic reactions. The reaction was stopped by adding 0.37 g of solid $CaCl_2$ and the vial was quickly closed with an open top crimp cap with teflon inlay. The vial was placed in a waterbath at 50° C. above a stirring device. After 10 minutes of preincubation while stirring, the volatiles in the headspace were sampled during 15 minutes, using SPME with a silica fiber coated with 100 µm polydimethylsiloxane (Supelco Inc., Bellefonte, Pa., USA). Volatiles trapped were identified by gas chromatography and mass spectrometry (GC-MS) according to Verhoeven et al. (1997).

FIG. 30 shows typical GC-MS chromatograms of volatiles produced by red tomatoes of both untransformed and transgenic FM6203 plants. Methylsalicylate production appeared significantly higher in fruit extracts of plants expressing both Lc and C1: its peak area, expressed as total ion counts x $10^6$, in control plants was 9.2±1.6 (mean±s.d.; n=2), while in plants independently transformed with both Lc and C1 it ranged from 17.2 to 32.2 (mean±s.d.: 29.6±11.4; n=3). In contrast, methylsalicylate production was not changed in fruits of plants expressing only lc (FIG. 30B): in these transgenic plants the mean±s.d. of the peak area was 10.8±2.1 (n=2). Of the two tested plants expressing only c1 in their fruits, one had a level comparable to that in the untransformed control plants, while the other (FIG. 30C) produced methylsalicylate similar to plants expressing both C1 and Lc. The applicants therefore speculate that the increase in the production of methylsalicylate in the fruits of plants transformed with the regulatory genes Lc and C1 is mainly due to the action of C1.

A significant increase in methylsalicylate level of tomatoes of the invention as compared to control fruits was found. Methylsalicylate is a key pathogen wound response volatile signalling molecule in plants. Its biosynthesis via the phenylpropanoid pathway probably involves benzoic acid as a precursor.

Surprisingly the combined insertion of Lc+C1 not only provide increased levels of flavonoids but also increased levels of Methylsalycilate and therewith offers possibilities for the selective tailoring of plants to produce altered levels of targeted aroma compunds and novel flavoured food materials.

What is claimed is:

1. A method for producing a tomato plant that exhibits increased levels of flavonols in the fruit of said plant comprising:

incorporating into said plant a DNA sequence encoding the maize C1 transcription factor in combination with a DNA sequence encoding the maize Lc transcription factor;

wherein the DNA sequence encoding the maize C1 transcription factor is operably linked to the constitutive double 35 s cauliflower mosaic virus promoter and wherein the DNA sequence encoding the maize Lc transcription factor is operably linked to the fruit-specific tomato E8 promoter; and, growing said plant under conditions wherein said genes encoding said transcription factors are expressed and said plant exhibits increased levels of flavonols.

2. The tomato plant prepared according to the method of claim 1.

3. Seeds, fruits, progeny and hybrids of the tomato plant of claim 2, wherein said seeds, fruits, progeny and hybrids comprise said DNA sequence encoding the maize C1 transcription factor in combination with a DNA sequence encoding the maize Lc transcription factor.

* * * * *